(12) United States Patent
Yoshikiyo et al.

(10) Patent No.: US 7,238,758 B2
(45) Date of Patent: Jul. 3, 2007

(54) CATALYSTS FOR POLYMERIZATION OR COPOLYMERIZATION OF α-OLEFINS, CATALYST COMPONENTS THEREOF, AND PROCESSES FOR POLYMERIZATION OF α-OLEFINS WITH THE CATALYSTS

(75) Inventors: Motozo Yoshikiyo, Ichihara (JP); Toshifumi Fukunaga, Ichihara (JP); Hiroshi Sato, Ichihara (JP); Toshikazu Machida, Ichihara (JP); Hiroyuki Ikeuchi, Ichihara (JP); Takefumi Yano, Ichihara (JP); Yasuhiro Tanaka, Ichihara (JP)

(73) Assignee: Ube Industries, Ltd. (JP)

( * ) Notice: Subject to any disclaimer, the term of this patent is extended or adjusted under 35 U.S.C. 154(b) by 0 days.

(21) Appl. No.: 10/503,414

(22) PCT Filed: Aug. 19, 2003

(86) PCT No.: PCT/JP03/10446

§ 371 (c)(1), (2), (4) Date: Apr. 12, 2005

(87) PCT Pub. No.: WO2004/016662

PCT Pub. Date: Feb. 26, 2004

(65) Prior Publication Data

US 2005/0202958 A1 Sep. 15, 2005

(30) Foreign Application Priority Data

| Aug. 19, 2002 | (JP) | 2002-238208 |
| Aug. 30, 2002 | (JP) | 2002-253059 |
| Feb. 4, 2003 | (JP) | 2003-026677 |
| Feb. 4, 2003 | (JP) | 2003-026678 |
| Apr. 4, 2003 | (JP) | 2003-101800 |
| Jun. 8, 2003 | (JP) | 2003-287355 |

(51) Int. Cl.
C08F 4/42 (2006.01)

(52) U.S. Cl. ............ 526/128; 526/351; 526/348; 526/904; 526/141; 526/125.6; 526/125.3; 526/126; 502/123; 502/103; 502/115; 502/116

(58) Field of Classification Search ........ 526/351, 526/348, 904, 141, 125.6, 125.3, 126, 128; 502/123, 103, 115, 116
See application file for complete search history.

(56) References Cited

FOREIGN PATENT DOCUMENTS

| EP | 0045975 | 2/1982 |
| EP | 0 273 456 A2 | 7/1988 |
| JP | 54094590 | 7/1979 |
| JP | 56045909 | 4/1981 |
| JP | 56055405 | 5/1981 |
| JP | 56163102 | 12/1981 |
| JP | 57115408 | 7/1982 |
| JP | 58083006 | 5/1983 |
| JP | 58083016 | 5/1983 |
| JP | 58138707 | 8/1983 |
| JP | 59058010 | 4/1984 |
| JP | 59149905 | 8/1984 |
| JP | 60023404 | 2/1985 |
| JP | 60032805 | 2/1985 |
| JP | 60044507 | 3/1985 |
| JP | 61018330 | 1/1986 |
| JP | 61055104 | 3/1986 |
| JP | 61-183304 | 8/1986 |
| JP | 62011705 | 1/1987 |
| JP | 63003010 | 1/1988 |
| JP | 63223008 | 9/1988 |
| JP | 63259807 | 10/1988 |
| JP | 01315406 | 12/1989 |
| JP | 02077413 | 3/1990 |
| JP | 02084404 | 3/1990 |
| JP | 02117905 | 5/1990 |
| JP | 03000706 | 1/1991 |
| JP | 03062805 | 3/1991 |
| JP | 03074393 | 3/1991 |
| JP | 04202505 | 7/1992 |
| JP | 04270705 | 9/1992 |
| JP | 04361019 | 12/1992 |
| JP | 04370103 | 12/1992 |
| JP | 05310751 | 11/1993 |
| JP | 06025332 | 2/1994 |
| JP | 06025336 | 2/1994 |
| JP | 07090012 | 4/1995 |
| JP | 07097411 | 4/1995 |
| JP | 07173212 | 7/1995 |
| JP | 08-003215 | * 1/1996 |

(Continued)

Primary Examiner—Ling-Sui Choi
(74) Attorney, Agent, or Firm—Trexler, Bushnell, Giangiorgi, Blackstone & Marr, ltd

(57) ABSTRACT

The invention has an object to provide a catalyst for polymerizing or copolymerizing an α-olefin, catalyst constituent thereof, and method of polymerizing α-olefins with the catalyst, for production of α-olefin polymers or copolymers with high hydrogen response, high polymarization reaction rate, high stereoregularity and excellent melt fluidity. The invention discloses a catalyst constituent of the catalyst for polymerizing or copolymerizing an α-olefin, represented by Formula 37 or 38:

$$Si(OR^1)_3(NR^2R^3) \qquad \text{Formula 37}$$

(where in Formula 37, $R^1$ is a hydrocarbon group with 1 to 6 carbon atoms; $R^2$ is a hydrocarbon group with 1 to 12 carbon atoms or hydrogen; and $R^3$ is a hydrocarbon group with 1 to 12 carbon atoms)

$$RNSi(OR^1)_3 \qquad \text{Formula 38}$$

(where in Formula 38, $R^1$ is a hydrocarbon group with 1 to 6 carbon atoms; and RN is a cyclicl amino group).

11 Claims, 12 Drawing Sheets

FOREIGN PATENT DOCUMENTS

| | | |
|---|---|---|
| JP | 08003215 | 1/1996 |
| JP | 08100019 | 4/1996 |
| JP | 08120021 | 5/1996 |
| JP | 08143620 | 6/1996 |
| JP | 08143621 | 6/1996 |
| JP | 08157519 | 6/1996 |
| JP | 08217841 | 8/1996 |
| JP | 08231663 | 9/1996 |
| JP | 09025316 | 1/1997 |
| JP | 09-040714 * | 2/1997 |
| JP | 09040714 | 2/1997 |
| JP | 09059312 | 3/1997 |
| JP | 11-060582 | 3/1999 |
| JP | 2000-063417 * | 2/2000 |
| JP | 2000063417 | 2/2000 |
| JP | 2000204111 | 7/2000 |
| WO | WO 0039171 | 7/2000 |

* cited by examiner

Fw=295.45

Constituent [A]: Solid Catalyst Consisting Essentially of Magnesium, Titanium, Halogen and Electron Donor Constituent [B]: Organoaluminum Compound Constituent [C]: Organosilicon Compound $Si(OR^1)_3(NR^2R^3)$ R1: Hydrocarbon Group with 1 to 4 Carbon Atoms
R2: Hydrocarbon Group with 1 to 12 Carbon Atoms or Hydrogen
R3: Hydrocarbon Group with 1 to 12 Carbon Atoms α-Olefin

CATALYSTS FOR POLYMERIZATION OR COPOLYMERIZATION OF α-OLEFINS, CATALYST COMPONENTS THEREOF, AND PROCESSES FOR POLYMERIZATION OF α-OLEFINS WITH THE CATALYSTS

TECHNICAL FIELD

The present invention relates to a catalyst for polymerizing or copolymerizing an α-olefin, catalyst component thereof, and method of polymerizing α-olefins with the catalyst for use in polymerization or copolymerization of α-olefins.

BACKGROUND ART

In recent years, in JP-A-57-63310, JP-A-58-83016, JP-A-59-58010, JP-A-60-44507 and others, there have been proposed, for polymerization of alpha-olefin, a number of highly active carrier-supported type catalyst systems comprising solid constituents containing indispensably magnesium, titanium, a halogen element and an electron donor, an organometal compound of a metal of I-III groups in Periodic Table, and an electron donor. Further, in JP-A-62-11705, JP-A-63-259807, JP-A-2-84404, JP-A-4-202505 and JP-A-4-370103, there have been disclosed other polymerization catalysts characterized by containing a specific organosilicon compound as an electron donor. For example, JP-A 2-84404 discloses a method that employs a cyclopentyl (alkyl)dimethoxy silane or di(cyclopentyl)dimethoxy silane as an electron donor. The catalyst systems using such the silicon compounds, however, are not always excellent in hydrogen response. JP-A 63-223008 discloses a catalyst system that employs a di(n-propyl)dimethoxy silane as an electron donor excellent in hydrogen response, which is though not particularly satisfactory at stereoregularity and causes a problem because an α-olefin polymer can not has an increased solidity.

JP-A 9-40714 proposes an alkoxy silane compound having an aliphatic amino substituent. JP-A 8-3215, 8-100019 and 8-157519 propose methods of manufacturing α-olefins using an alkoxy silane having an aliphatic amino substituent as a catalyst component, which are though not always satisfactory at hydrogen response. JP-A 8-143620 proposes a method of manufacturing α-olefin using a dialkoxy silane having two aliphatic amino substituents as an electron donor, which is though not always satisfactory at polymerization activity and stereoregularity in performance.

JP-A 8-100019 and 8-157519 propose methods of manufacturing α-olefin polymers having a small molecular weight (or large MFR) using a dialkoxy silane having a hydrocarbon group-containing amino substituent and a hydrocarbon group as a catalyst component. They describe examples of polymers with MFR of 60 g/10 min at most, which are not always satisfactory at hydrogen response in performance.

JP-A 8-120021, 8-143621 and 8-2316663 disclose methodes using cyclic amino silane compounds. When these specifically described compounds are employed as catalyst components, they exhibit high stereoregularity but are not always adequately satisfactory at hydrogen response. In addition, a problem occurs because a molecular weight distribution is not always wide.

JP-A 6-25336, 7-90012 and 7-97411 disclose methodes using a nitrogen atom-containing heterocyclic substitutional organosilicon compound that includes a silicon atom directly bonded to any carbon atom in a heterocycle, but they fail to describe any molecular weight distribution. JP-A 3-74393 and 7-173212 disclose methodes using a monocyclic amino group-containing organosilicon compound but fail to describe any molecular weight distribution.

A propylene polymer with a wide molecular weight distribution and high stereoregularity can be produced in such a method that can be considered as comprising: producing a high stereoregularity and low molecular weight propylene polymer and a high crystallinity and high molecular weight propylene polymer previously using a conventional method; and then melting and blending them in a desirable ratio. In this case, production of the propylene polymer with a relatively low molecular weight and wide molecular weight distribution makes it extremely difficult to melt and blend the low molecular weight propylene polymer and the high molecular weight propylene polymer uniformly, resulting in problems associated with gel generation, for example.

JP-A 2000-63417 discloses a method that provides an α-olefin polymer with high activity, high hydrogen response, high stereoregularity and wide molecular weight distribution. This system, however, worsens hydrogen response and greatly sacrifices stereoregularity when the molecular weight distribution is extended to an aimed value. Thus, an improvement is required.

A high hydrogen response is also important. Namely, when hydrogen coexists in a polymerization system to adjust the molecular weight, a low hydrogen response requires a large amount of hydrogen. Therefore, as described above, the use of an excessive chain transfer agent such as hydrogen is required to produce a low molecular weight polymer. Consequently, it is required to lower a polymerization temperature during bulk polymerization in a polymerization device having a pressure-proof limit and reduce a monomer partial pressure during gas-phase polymerization, resulting in an ill effect exerted on the productivity rate disadvantageously.

JP-A8-143620 according to the applicant proposes a method of manufacturing an α-olefin using a dialkoxy silane having two aliphatic amino substitutions as an electron donor. This method, however, may lower stereoregularity (H. I.) and polymerization activity on production of polymers with MFR of 200 or more and is not always satisfactory at performance.

JP-A 8-3215 and 9-40714 also according to the applicant propose an alkoxy silane compound having an aliphatic amino substitution and methods of manufacturing stereoregularity and melt fluidity (that is, high MFR) using the same. The silane compound described therein, however, is only a dialkoxy silane having both of one amino group containing hydrocarbon group and one hydrocarbon group, that is, a dialkoxy silane represented by $R^1Si(OR^2)_2(NR^3R^4)$. In addition, specifically exemplified compounds are only dimethoxy silanes, for example, a methyl(diethylamino)dimethoxy silane. As for a trialkoxy silane represented by $Si(OR^2)_3(NR^3R^4)$, no specific compound is exemplified. The obtained polymerization result is not always satisfactory because a larger MFR results in a lower stereoregularity.

JP-A 2000-63417 and 2000-204111 disclose methods using organosilicon compounds and polycyclic amino organosilicon compounds. When the compounds described therein are employed as catalysts, they exhibit high stereoregularity but are not always satisfactory at hydrogen response.

The carrier catalyst system using the electron donor described earlier is not always satisfactory at balanced polymerization activity, stereoregularity and hydrogen response in performance, and accordingly a further improvement is required.

In recent years, in the field of injection molding mainly for automobile materials and household electrical materials, for the purpose of thinning and light-weighting of products, α-olefin polymers with high melt fluidity, high solidity and high heat resistance are increasingly needed. It is important to use a catalyst with a high hydrogen response during polymerization to produce such α-olefin polymers. Specifically, it is general to allow hydrogen to coexist as a chain transfer agent in the polymerization system to adjust the molecular weight of the α-olefin polymer. In particular, to increase the melt fluidity of the α-olefin polymer, hydrogen is required to lower the molecular weight. Melt flow rate is employed as an index of the melt fluidity of the α-olefin polymer. The lower the molecular weight of the α-olefin polymer is related with the higher the melt flow rate. A lower hydrogen response requires a large amount of hydrogen in the polymerization system to increase the melt flow rate of the α-olefin polymer. A higher hydrogen response does not require such the amount of hydrogen as is required in the case of the lower hydrogen response to produce the α-olefin polymer with the same melt flow rate. Accordingly, the low hydrogen response requires introduction of an excessive amount of hydrogen into the polymerization system to elevate the melt flow rate of the α-olefin polymer. Consequently, for safety in a production method, the polymerization temperature in the polymerization device having the pressure-proof limit should be lowered in relation to an increased hydrogen partial pressure. This exerts ill effects on the production speed and the quality disadvantageously.

On the other hand, ethylene propylene block copolymers are widely employed for household electrical and automobile materials and required to reduce their production costs. Methodes of manufacturing ethylene propylene block copolymers include a method with the conventional catalyst system, which comprises producing an ethylene propylene block copolymer in a polymerization reactor; and then mixing and kneading a rubber component mechanically, though it has a problem because of its high cost. Therefore, in a method using multistage polymerization devices, a propylene homopolymer is produced at the first stage polymerization device, and a sufficient amount of copolymer is produced during ethylene propylene copolymerization in the following polymerization stages. In this case, such a catalyst system is strongly desired that can produce the so-called linearly polymerized block copolymer of ethylene and propylene so that the produced block polymer has sufficient fluidity.

As for the block copolymer from the conventional catalyst system, if an amount of the polymer in the following stages reaches 10% or more of the polymer in the first state, molding is substantially impossible. This is because the melt fluidity is extremely small unless the rubber component in the block copolymer (a room temperature p-xylene soluble component) has an extremely small value of [η].

As a method of manufacturing ethylene propylene block copolymers, JP-A 8-217841 also filed by the applicant discloses one, which employs a silane compound or bis (dialkylamino)silane as a component of a polymerization catalyst. JP-A8-231663 also filed by the applicant discloses another method, which employs a silane compound or bis(dicyclicamino)silane as a component of a polymerization catalyst. These methodes, however, have a subject associated with insufficient hydrogen response.

To solve the above problems associated with the prior arts, the present invention has an object to provide a catalyst for polymerizing or copolymerizing an α-olefin, catalyst component thereof, and method of polymerizing α-olefins with the catalyst, for production of α-olefin polymers or copolymers with high hydrogen response, high polymerization activity, high stereoregularity and excellent melt fluidity.

SUMMARY OF THE INVENTION

The present invention is described below. In the invention, α-olefin includes ethylene, propylene, 1-butene, 1-hexene, 4-methylpentene-1,3-methylbutene-1,1-octene and others.

Catalyst Components

For achievement of the above object, the present invention is directed to a catalyst constituent of catalyst for polymerizing or copolymerizing an α-olefin, represented by Formula 14.

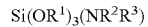  Formula 14

In Formula 14, $R^1$ is a hydrocarbon group with 1 to 6 carbon atoms, such as an unsaturated or saturated aliphatic hydrocarbon group with 1 to 6 carbon atoms, and more preferably a hydrocarbon group with 2 to 6 carbon atoms. Specifically, it includes methyl group, ethyl group, n-propyl group, iso-propyl group, n-butyl group, iso-butyl group, ter-butyl group, sec-butyl group, n-pentyl group, iso-pentyl group, cyclopentyl group, n-hexyl group, cyclohexyl group and others. Ethyl group is particularly preferred.

In Formula 14, $R^2$ is a hydrocarbon group with 1 to 12 carbon atoms or hydrogen, such as an unsaturated or saturated aliphatic hydrocarbon group with 1 to 12 carbon atoms or hydrogen. Specifically, it includes hydrogen, and methyl group, ethyl group, n-propyl group, iso-propyl group, n-butyl group, iso-butyl group, ter-butyl group, sec-butyl group, n-pentyl group, iso-pentyl group, cyclopentyl group, n-hexyl grou, cyclohexyl group and others. Ethyl group is particularly preferred.

In Formula 14, $R^3$ is a hydrocarbon group with 1-12 carbon atoms, such as an unsaturated or saturated aliphatic hydrocarbon group with 1-12 carbon atoms. Specifically, it includes methyl, ethyl, n-propyl, iso-propyl, n-butyl, iso-butyl, ter-butyl, sec-butyl, n-pentyl, iso-pentyl, cyclopentyl, n-hexyl and cyclohexyl groups. Ethyl group is particularly preferred.

The compound of Formula 14 preferably comprises one or more of dimethylaminotriethoxysilane; diethylaminotriethoxysilane; diethylaminotrimethoxysilane; diethylaminotri-n-propoxysilane; di-n-propylaminotriethoxysilane; methyl-n-propylaminotriethoxysilane; t-butylaminotriethoxysilane; ethyl-n-propylaminotriethoxysilane; ethylisopropylaminotriethoxysilane; and methylethylaminotriethoxysilane. These organosilicon compounds may be employed solely or in combination of two or more.

The compound of Formula 14 can be synthesized by reacting an alkyl amine equivalently with a Grignard reagent to produce a magnesium salt of an alkyl amine through Grignard exchange reaction; and then reacting tetraethoxysilane with equivalent amount of the magnesium salt of alkyl amine. A lithium salt may be employed instead of the magnesium salt. In addition to synthesis using the Grignard reagent, the compound of Formula 14 may also be synthesized by reacting an alkoxy silane halide with a dialkyl amine as described later.

Diethylaminotriethoxysilane, or the compound of Formula 14 for use in the invention, can be synthesized by reacting diethylamine with equivalent amount of a Grignard reagent to produce a magnesium salt of diethylamine through Grignard exchange reaction; and then reacting tetraethoxysilane with equivalent amount of the magnesium salt of diethylamine. A lithium salt of diethyl amine may be employed instead of the magnesium salt of diethyl amine.

Methyl-n-propylaminotriethoxysilane, or the compound of Formula 14 for use in the invention, can be synthesized by reacting a methyl-n-propyl amine with equivalent amount of a Grignard reagent to produce a magnesium salt of methyl-n-propylamine through Grignard exchange reaction; and then reacting tetraethoxysilane with equivalent amount of the magnesium salt of methyl-n-propyl amine. A lithium salt of methyl-n-propylamine may be employed instead of the magnesium salt of methyl-n-propyl amine.

T-butylaminotriethoxysilane, or the compound of Formula 14 for use in the invention, can be synthesized by reacting a t-butyl amine with equivalent amount of a Grignard reagent to produce a magnesium salt of t-butyl amine through Grignard exchange reaction; and then reacting tetraethoxysilane with equivalent amount of the magnesium salt of t-butyl amine. A lithium salt of t-butylamine may be employed instead of the magnesium salt of t-butyl amine.

Ethyl-n-propylaminotriethoxysilane, or the compound of Formula 14 for use in the invention, can be synthesized by reacting ethyl-n-propylamine with equivalent amount of a Grignard reagent to produce a magnesium salt of ethyl-n-propylamine through Grignard exchange reaction; and then reacting tetraethoxysilane with equivalent amount of the magnesium salt of ethyl-n-propylamine. A lithium salt of ethyl-n-propylamine may be employed instead of the magnesium salt of ethyl-n-propylamine.

Methylethylaminotriethoxysilane, or the compound of Formula 14 for use in the invention, can be synthesized by reacting methylethylamine with equivalent amount of a Grignard reagent to produce a magnesium salt of methylethylamine through Grignard exchange reaction; and then reacting tetraethoxysilane with equivalent amount of the magnesium salt of methylethylamine. A lithium salt of methylethylamine may be employed instead of the magnesium salt of methylethylamine.

For achievement of the above object, the present invention is directed to a catalyst constituent of catalyst for polymerizing or copolymerizing an α-olefin, represented by Formula 15.

$$RNSi(OR^1)_3 \qquad \text{Formula 15}$$

In Formula 15, $R^1$ is a hydrocarbon group with 1 to 6 carbon atoms, such as an unsaturated or saturated aliphatic hydrocarbon group with 1 to 6 carbon atoms, and more preferably a hydrocarbon group with 2 to 6 carbon atoms. Specifically, it includes methyl group, ethyl group, n-propyl group, iso-propyl group, n-butyl group, iso-butyl group, ter-butyl group, sec-butyl group, n-pentyl group, iso-pentyl group, cyclopentyl group, n-hexyl group, cyclohexyl group and others. An ethyl group is particularly preferred.

In Formula 15, RN is a cyclic amino group, such as perhydroquinolino group; perhydroisoquinolino group; 1,2,3,4-tetrahydroquinolino group; 1,2,3,4-tetrahydroisoquinolino group; and octamethyleneimino group.

The compound of Formula 15 specifically includes (perhydroquinolino)triethoxysilane, (perhydroisoquinolino)triethoxysilane, (1,2,3,4-tetrahydroquinolino)triethoxysilane, (1,2,3,4-tetrahydroisoquinolino)triethoxysilane, and octamethyleneiminotriethoxysilane.

The compound of Formula 15 can be synthesized by reacting polycyclic amine such as perhydroquinoline with equivalent amount of a Grignard reagent to produce a magnesium salt of polycyclic amine through Grignard exchange reaction; and then reacting tetraethoxysilane with equivalent amount of the magnesium salt of polycyclic amine. A lithium salt of polycyclic amine produced with butyl lithium or the like may be employed instead of the magnesium salt of polycyclic amine. In addition to synthesis using the Grignard reagent, the compound of Formula 15 may also be synthesized by reacting an alkoxy silane halide with a dialkyl amine as described later.

Method of Manufacturing Catalyst Components

In addition to the above synthesis using the Grignard reagent, the catalyst component of Formula 14 may also be synthesized by reacting an alkoxy silane halide represented by Formula 16 with a dialkyl amine represented by Formula 17.

$$X_nSi(OR^1)_{4-n} \qquad \text{Formula 16}$$

$$NHR^2R^3 \qquad \text{Formula 17}$$

In the alkoxy silane halide represented by Formula 16, X denotes halogen group, such as fluoro group, chloro group and bromo group, and more preferably chloro group. In the alkoxy silane halide represented by Formula 16, $R^1$ is a hydrocarbon group with 1 to 4 carbon atoms, for example, methyl group; ethyl group; propyl group such as n-propyl group and iso-propyl group; and butyl group such as n-butyl group, iso-butyl group and tert-butyl group. Ethyl group is particularly preferred. In the alkoxy silane halide represented by Formula 16, n=1, 2, 3. The alkoxy silane halide represented by Formula 16 specifically includes fluorotriethoxysilane, chlorotriethoxysilane, chlorotrimethoxysilane, chlorotri-n-propoxysilane, and bromotriethoxysilane. Chlorotriethoxysilane is particularly preferred.

In the dialkyl amine represented by Formula 17, $R^2$ is a hydrocarbon group with 1 to 12 carbon atoms or hydrogen, such as an unsaturated or saturated aliphatic hydrocarbon group with 1 to 12 carbon atoms or hydrogen. Specifically, it includes hydrogen, and methyl group, ethyl group, n-propyl group, iso-propyl group, n-butyl group, iso-butyl group, ter-butyl group, sec-butyl group, n-pentyl group, iso-pentyl group, cyclopentyl group, n-hexyl group, cyclohexyl group, octyl group and others. Ethyl group is particularly preferred.

In the dialkyl amine represented by Formula 17, $R^3$ is a hydrocarbon group with 1 to 12 carbon atoms, such as an unsaturated or saturated aliphatic hydrocarbon group with 1-12 carbon atoms. Specifically, it includes methyl group, ethyl group, n-propyl group, iso-propyl group, n-butyl group, iso-butyl group, ter-butyl group, sec-butyl group, n-pentyl group, iso-pentyl group, cyclopentyl group, n-hexyl group, cyclohexyl group, octyl group and others. Ethyl group is particularly preferred.

The dialkyl amine represented by Formula 17 includes dimethylamine, diethylamine, di-n-propylamine, methyl-n-propylamine, t-butylamine, ethyl-n-propylamine, ethylisopropylamine, methylethylamine and others.

In addition to the above synthesis using the Grignard reagent, the catalyst component represented by Formula 15 may also be synthesized by reacting the alkoxy silane halide represented by Formula 16 with a cyclic amine represented by Formula 18.

$$RNH \qquad \text{Formula 18}$$

In the cyclic amine represented by Formula 18, RN is a cyclic amino group, such as perhydroquinolino group, perhydroisoquinolino group, 1,2,3,4-tetrahydroquinolino group, 1,2,3,4-tetrahydroisoquinolino group, and octamethyleneimino group.

Specific examples of the cyclic amine represented by Formula 18 include perhydroquinoline, perhydroisoquinoline, 1,2,3,4-tetrahydroquinoline, 1,2,3,4-tetrahydroisoquinoline, octamethyleneimine and others.

The compound represented by Formula 16 can be produced in a novel method invented by the Inventors et al., which comprises reacting a tetrahalo silane represented by Formula 19 with an orthoformate ester represented by Formula 20.

  Formula 19

  Formula 20

In the tetrahalo silane represented by Formula 19, X is a halogen group, such as fluoro group, chloro group and bromo group, and more preferably chloro group. The tetrahalo silane represented by Formula 19 specifically includes tetrafluorosilane, tetrachlorosilane, and tetrabromosilane. Tetrachloro silane is particularly preferred.

In the orthoformate ester represented by Formula 20, $R^1$ is a hydrocarbon group with 1-4 carbon atoms, for example, methyl group; ethyl group; propyl group such as n-propyl group and iso-propyl group; and butyl group such as n-butyl group, iso-butyl group and tert-butyl group. Ethyl group is particularly preferred. The orthoformate ester represented by Formula 20 specifically includes methyl orthoformate and ethylorthoformate. Among those, Ethyl orthoformate is particularly preferred.

The reaction between the tetrahalo silane represented by Formula 19 and the orthoformate ester represented by Formula 20 may proceed without the use of any solvent though such a solvent may be employed that can not react with a material and with a reacted product. If a solvent is employed, it may be n-heptane, toluene, or diethylether. Among them, n-heptane is preferable.

A reaction temperature ranges preferably between −20 and 200° C., and more preferably between 0 and 120° C. A reaction time normally ranges between 0.25 and 120 hours and varies based on types and amounts of the tetrahalo silane and orthoformate ester and the catalyst and solvent, and on the reaction temperatures. In another case, preferably, a reaction is performed at between −20 and 15° C. for between 0.25 and 24 hours, and then another reaction is performed at room temperature for between 0.25 and 120 hours.

An additional ratio between the tetrahalo silane represented by Formula 19 and the orthoformate ester represented by Formula 20 can control the number of X and OR bonded to Si, that is n in $X_nSi(OR)_{4-n}$. As for a trialkoxyhalo silane represented by $X_1Si(OR)_3$ in the case of n=1, preferably $SiX_4$: $HC(OR)_3$=1:2.6 to 3.5 (molar ratio).

A reaction can proceed with no catalyst though the use of an acidic catalyst is desirable because it can reduce the reaction time effectively. The acidic catalyst may be either a Lewis acid or a Bronsted acid. The Lewis acid includes aluminum chloride, titanium chloride, and boron fluoride. Preferably, from the viewpoint of suppressing the generation of hydrogen halide gases, the Bronsted acid includes an acid in such a form that does not contain an extra water content. For example, it includes carboxylic acid (such as a trifluoroacetic acid), sulfonic acid (such as p-toluene sulfonic acid), and polyphosphoric acid. Among those, p-toluene sulfonic acid is preferable. The p-toluene sulfonic acid may be employed as a hydrate unless generation of a small amount of hydrogen halides causes any problem.

An additional amount of the p-toluene sulfonic acid to $SiX_4$ ranges preferably between $10^{-5}$ and 10 mole %, more preferably between $10^{-2}$ and 5 mole %.

Preferably, the reaction is performed by dropping the orthoformate ester represented by Formula 20 into the tetrahalo silane represented by Formula 19. In this case, both or either of them may be formed in solution.

The alkoxy silane halide represented by Formula 16, produced through the reaction between the tetrahalosilane represented by Formula 19 and the orthoformate ester represented by Formula 20, is not isolated and is reacted with the dialkyl amine represented by Formula 17 to produce the catalyst component of Formula 14.

The alkoxy silane halide represented by Formula 16, produced through the reaction between the tetrahalosilane represented by Formula 19 and the orthoformate ester represented by Formula 20, is not isolated and is reacted with the cyclic amine represented by Formula 18 to produce the catalyst component of Formula 15.

In addition to the use of the Grignard reagent, a (dialkylamino)alkoxy silane may be produced from an alkoxy silane halide employed as a material in a known method.

Alkoxy silane halides are not only semiconductor method materials but also suitable precursors on chemical synthesis for various low-molecular and high-molecular silicon compounds. Namely, through the use of differences in reactivity between a halogeno group and an alkoxy group and variations in the substituted number of the substituents, various high value-added silicon compounds can be derived.

Methods of manufacturing the above alkoxy silane halides are disclosed, for example, in J. Am. Chem. Soc., vol. 68, p. 70 (1946) and Khimiya i Industriya, No. 6, p. 248 (1983), which produce chloroethoxysilane by reacting tetrachlorosilane with ethanol. These methods, however, generate hydrogen chloride gas in the reaction system. Therefore, it is required to remove the gas and make it harmless. In addition, a restriction occurs on the reactor due to the gas being corrosive. Measures applied for those are unsatisfactory not only at method steps but also at costs. Thus, a further improvement is desired.

On the other hand, a patent publication (JP-A 5-310751) proposes a method of manufacturing through a reaction of tetrachlorosilane with tetraalkoxysilane. This method can prevent generation of the hydrogen chloride gas though yields in examples are 60 to 75% at most, and a much higher yield is desired.

As disclosed in Zhurnal Obshchei Khimii, vol. 65, p. 1142 (1995), trichloroethoxysilane can be produced at a maximum yield of 90% through a reaction of tetrachlorosilane with tetraalkoxysilane in the presence of ethanol. In this reaction system, however, it is obvious that hydrogen chloride gas is generated.

The above method of manufacturing the catalyst can provide alkoxy silane halides and diethylamino trialkoxy silanes at a high yield without generation of corrosive gases such as hydrogen chloride gas.

α-Olefin Polymerization or Copolymerization Catalysts

For achievement of the above object, the present invention is directed to a catalyst for polymerizing or copolymerizing an α-olefin, which includes the catalyst constituent of Formula 14 or Formula 15. For example, it includes [A] a solid catalyst constituent consisting essentially of magnesium, titanium, a halogen element and an electron donor; [B] an organoaluminum compound constituent; and [C] the catalyst constituent of Formula 14 or Formula 15.

In the present invention, a solid constituent of the catalyst, containing magnesium, titanium, a halogen element and an electron donor indispensably, is used as the constituent (A). Since there is no particular restriction as to the method for preparation of the solid constituent of the catalyst, it can be prepared by using methods for example those proposed in JP-A-54-94590, JP-A-56-55405, JP-A-56-45909, JP-A-56-163102, JP-A-57-63310, JP-A-57-115408, JP-A-58-83006, JP-A-58-83016, JP-A-58-138707, JP-A-59-149905, JP-A-60-23404, JP-A-60-32805, JP61-183304, JP-A-61-55104, JP-A-2-77413, JP-A-2-117905 and others.

As to the representative method for preparing the solid catalyst constituent (A), there can be exemplified (i) a method which comprises co-grinding a magnesium compound, an electron donor and a titanium halide compound, or dispersing and dissolving them in a solvent to allow them to contact with each other for preparation of the catalyst constituent, (ii) A method which comprises dissolving a magnesium compound and an electron donor in a solvent and adding a titanium halide compound to the resulting solution to precipitate a solid catalyst and others.

The magnesium compound available for preparation of the solid catalyst constituent [A] includes a magnesium halide and a di(alkoxy)magnesium. The magnesium halide specifically includes magnesium chloride, magnesium bromide, magnesium iodide, and magnesium fluoride. The magnesium chloride is particularly preferable. Specifically, the di(alkoxy)magnesium includes di(methoxy)magnesium, di(ethoxy)magnesium, di(n-propoxy)magnesium, di(n-butoxy)magnesium, ethoxy(methoxy)magnesium, ethoxy(n-propoxy)magnesium, butoxy(ethoxy)magnesium and others. The di(ethoxy)magnesium and di(n-butoxy)magnesium are particularly preferable. These di(alkoxy)magnesium may be prepared by reacting a metal magnesium with an alcohol in the presence of a halogen or a halogen-containing metal compound. The dialkoxy magnesium may be employed solely or in combination of two or more.

The dialkoxy magnesium for use in preparation of the solid catalyst constituent [A] may be shaped in a granulated, powdery, indeterminate or spherical form. For example, the use of spherical dialkoxy magnesium can produce an α-olefin homopolymer excellent in morphology and having a narrow particle diameter distribution, or a copolymer powder with another α-olefin to achieve good powder fluidity. This is effective to solve the problem associated with clogging of hoppers and lines during production, for example.

Specific examples of the titanium halide compounds available for preparation of the solid catalyst constituent [A] include tetrahalide titanium such as tetrachloro titanium and tetrabromo titanium; trihalide(alkoxy)titanium such as trichloro(methoxy)titanium, trichloro(ethoxy)titanium, trichloro(propoxy)titanium, trichloro(butoxy)titanium, tribromo(methoxy)titanium, tribromo(ethoxy)titanium, tribromo(propoxy)titanium, and tribromo(butoxy)titanium; dihalide(dialkoxy)titanium such as dichloro(dimethoxy) titanium, dichloro(diethoxy)titanium, dichloro(dipropoxy) titanium, and dichloro(dibutoxy)titanium; and halide(trialkoxy)titanium such as chloro(trimethoxy)titanium, chloro(triethoxy)titanium, chloro(tripropoxy)titanium, and chloro(tributoxy)titanium. Particularly, the tetrachlorotitanium is preferable. These titanium halides may be employed solely or in combination of two or more.

The electron donor for use in preparation of the solid catalyst constituent [A] includes a Lewis basic compound, preferably an aromatic diester, more preferably an orthophthalic diester. The orthophthalic diester specifically includes dimethyl orthophthalate, (ethyl)methyl orthophthalate, diethyl orthophthalate, (ethyl)n-propyl orthophthalate, di-n-propyl orthophthalate, (n-butyl)n-propyl orthophthalate, (n-butyl)ethyl orthophthalate, (iso-butyl)ethyl orthophthalate, di-n-butyl orthophthalate, diiso-butyl orthophthalate, n-pentyl orthophthalate, diiso-pentyl orthophthalate, di-n-hexyl orthophthalate, bis(2-ethylhexyl) orthophthalate, di-n-heptyl orthophthalate, di-n-octyl orthophthalate and others. Particularly, diethyl orthophthalate, di-n-propyl orthophthalate, di-n-butyl orthophthalate, diiso-butyl orthophthalate, di-n-heptyl orthophthalate, bis(2-ethylhexyl)orthophthalate, and di-n-octyl orthophthalate are preferable. These orthophthalic diesters may be employed solely or in combination of two or more.

Compounds having two or more ether groups shown in JP-A 3-706, 3-62805, 4-270705 and 6-25332 may preferably be employed as the electron donor. Further, maleic diesters having a linear or branched alkyl group with 2-8 carbon atoms shown in the republished WO 00/39171 may be employed as the electron donor. Among these maleic diesters, di n-butyl maleate is particularly preferable.

Organoaluminum compounds as to the constituent [B] used in the present invention includes an alkyl aluminum halide such as an alkyl aluminum and a diethyl aluminum chloride, preferably an alkyl aluminum, and specifically a tri(alkyl)aluminum. Specific examples include tri(methyl) aluminum, tri(ethyl)aluminum, tri(n-propyl)aluminum, tri (n-butyl)aluminum, tri(isobutyl)aluminum, tri(n-hexyl)aluminum, and tri(n-octyl)aluminum. Among those, tri(ethyl) aluminum is preferable particularly. These organoaluminum compounds may be employed solely or in combination of two or more. Polyaluminoxan, produced through reaction of alkyl aluminum with water, may be employed similarly.

An amount of the organoaluminum compound constituent [B] used as the α-olefin polymerization catalyst ranges between 0.1 and 1500, preferably between 50 and 1000, in molar ratio relative to titanium in the solid catalyst constituent [A].

An amount of the constituent [C] ranges between 0.001 and 10, preferably between 0.005 and 5, in molar ratio (Si/Al) relative to aluminum in the constituent [B].

For achievement of the above object, the present invention is directed to a catalyst for polymerizing or copolymerizing an α-olefin, which, in addition to the constituents [A], [B] and [C], further includes [D] an organosilicon compound constituent represented by Formula 21 or Formula 22.

Formula 21

Formula 22

In Formula 21 or Formula 22 of the invention, $R^1$ represents a hydrocarbon group having 1 to 8 carbon atoms including an unsaturated or saturated aliphatic hydrocarbon group having 1 to 8 carbon atoms. Specific examples of $R^1$ include methyl group, ethyl group, n-propyl group, iso-propyl group, n-butyl group, iso-butyl group, ter-butyl group, sec-butyl group, n-pentyl group, iso-pentyl group, cyclopentyl group, n-hexyl group and cyclohexyl group. Among these, methyl group is particularly preferred.

$R^2$ represents a hydrocarbon group having 2 to 24 carbon atoms, preferably 2 to 8 carbon atoms, a hydrocarbylamino group having 2 to 24 carbon atoms, preferably 2 to 8 carbon atoms, or a hydrocarbylalkoxy group having 2 to 24 carbon atoms, preferably 2 to 8 carbon atoms. Among these, a hydrocarbon group having 2 to 24 carbon atoms or a hydrocarbylamino group having 2 to 24 carbon atoms is preferred.

Specific examples of the hydrocarbon group having 2 to 24 carbon atoms include ethyl group, n-propyl group, iso-propyl group, n-butyl group, iso-butyl group, sec-butyl group, ter-butyl group, n-pentyl group, iso-pentyl group, n-hexyl group, n-heptyl group, n-octyl group, cyclopentyl group, cyclohexyl group, texyl group, phenyl group benzyl group, tolyl group and the like. The other example is a hydrocarbon group containing silicon atom such as trimethylsilylmethyl group and bis trimethylsilylmethyl group.

Specific examples of the hydrocarbylamino group having 2 to 24 carbon atoms include, dimethylamino group, methylethylamino group, diethylamino group, ethyl-n-propyl-amino group, di-n-propyl-amino group, ethylisopropyl-amino group, diisopropyl-amino group, pyrrolidino group, piperidino group, and hexamethyleneimino group.

Specific examples of the hydrocarbylalkoxy group having 2 to 24 carbon atoms include methoxy group, iso-propoxy group, and ter-butoxy group.

Among them, propyl group such as n-propyl group and isopropyl group, butyl group such as iso-butyl group and ter-butyl group, cyclopentyl group, diethylamino group, ter-butoxy group, and the like are preferably used.

$R^3N$ represents a polycyclic amino group having 7 to 40 carbon atoms, wherein the carbon atoms and the nitrogen atom form a cyclic skeleton. The polycyclic amino group may be a saturated polycyclic amino group, or may be a partially or entirely unsaturated polycyclic amino group. The nitrogen atom of the polycyclic amino group is bonded directly to the silicon atom of the organosilicon compound to form Si—N bond. Thus, the polycyclic amino group can be defined as a substituent formed by chemically bonding the N atom to Si atom by removing the hydrogen atom from the secondary amine $R^3NH$. In the general formula 21, each one of two $R^3N$ groups may be the same or different.

Specific examples of the polycyclic amino group include amine compounds as mentioned by the following chemical structural formulas 23; perhydroindole, perhydroisoindole, perhydroquinoline, perhydroisoquinoline, perhydrocarbazole, perhydroacrydine, perhydrophenanthoridine, perhydrobenzo(g)quinoline, perhydrobenzo(h)quinoline, perhydrobenzo(f)quinoline, perhydrobenzo(g)isoquinoline, perhydrobenzo(h)isoquinoline, perhydrobenzo(f)isoquinoline, perhydroacequinoline, perhydroaceisoquinoline, perhydroiminostilbene, and amine compounds in which some of the hydrogen atoms other than the nitrogen atom are substituted with alkyl group, phenyl group or cycloalkyl group.

Formula 23

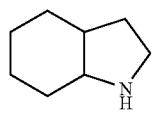
Perhydroindole

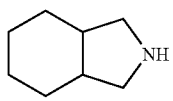
Perhydroisoindole

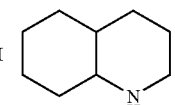
Perhydroquinoline

-continued

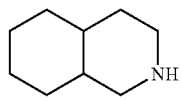
Perhydroisoquinoline

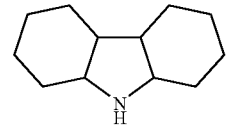
Perhydrocarbazole

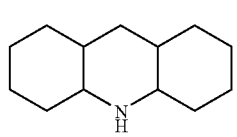
Perhydroacridine

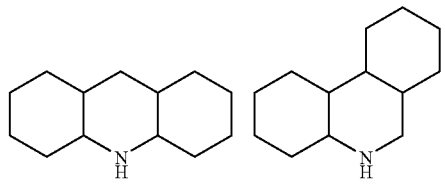
Perhydrophenanthridine

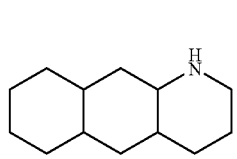
Perhydrobenzo(g)quinoline

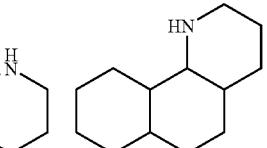
Perhydrobenzo(h)quinoline

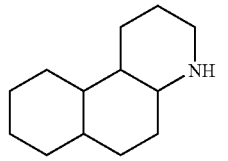
Perhydrobenzo(f)quinoline

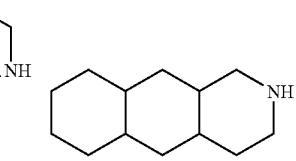
Perhydrobenzo(g)isoquinoline

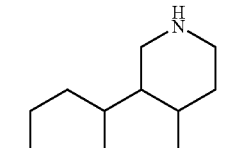
Perhydrobenzo(h)isoquinoline

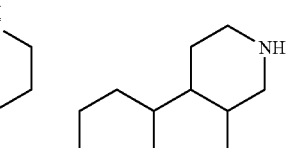
Perhydrobenzo(f)isoquinoline

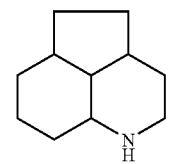
Perhydroacequinoline

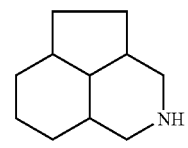
Perhydroaceisoquinoline

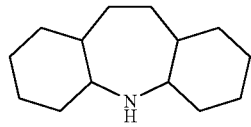
Perhydroiminostilbene

Further, $R^3NH$ represents amine compounds such as 1,2,3,4-tetrahydroquinoline and 1,2,3,4-tetrahydroisoquinoline as mentioned by the following chemical structural formulas 24, which is a partially unsaturated polycyclic amino compound, or in which some of the hydrogen atoms other than the nitrogen atom are substituted with alkyl group, phenyl group or cycloalkyl group.

Formula 24

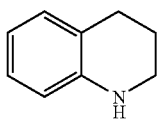  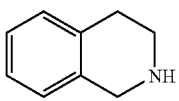

1,2,3,4-tetrahydroquinoline   1,2,3,4-tetrahydroisoquinoline

Specifically preferable examples of the amine compounds represented by $R^3NH$ include perhydroquinoline, perhydroisoquinoline, 1,2,3,4-tetrahydroquinoline, 1,2,3,4-tetrahydroisoquinoline, and their derivatives.

As to the organosilicon compounds represented by the formula 21, there can be exemplified a bisperhydroquinolino compound represented by the formula 25, a bisperhydroisoquinolino compound represented by the formula 26, a (perhydroquinolino)perhydroisoquinolino compound represented by the formula 27, bis(1,2,3,4-tetrahydroquinolino) compound represented by the formula 28, a bis(1,2,3,4-tetrahydroisoquinolino) compound represented by the formula 29, a (1,2,3,4-tetrahydroquinolino)(1,2,3,4-tetrahydroisoquinolino) compound represented by the formula 30. In the present invention, the bisperhydroquinolino compound represented by Formula 25 is particularly preferable.

Formula 25

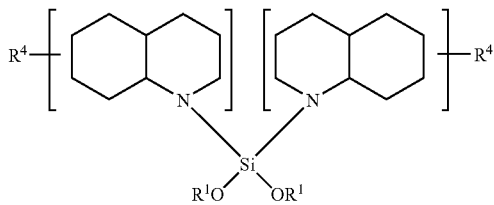

Formula 26

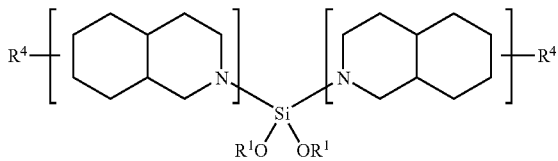

Formula 27

Formula 28

Formula 29

Formula 30

In the above formulas, $R^4$ represents a substituted group on the saturated cyclic skeleton of the general formula $R^3N$ and is hydrogen atom, or a saturated or unsaturated aliphatic hydrocarbon group having 1 to 24 carbon atoms. The preferable examples of $R^4$ includes hydrogen atom, methyl group, ethyl group, n-propyl group, iso-propyl group, n-butyl group, iso-butyl group, ter-butyl group, sec-butyl group, and the like. The number of hydrocarbon groups substituted on the saturated cyclic structure of $R^3N$ may be 1 or more.

As to the compound represented by the formula 23, bis(perhydroquinolino)dimethoxysilane is exemplified. This compound is most preferable for the constituent [D] of the present invention. Specific examples of the bis(methyl-substituted-perhydroquinolino)dimethoxysilane compounds include,
bis(2-methylperhydroquinolino)dimethoxysilane,
bis(3-methylperhydroquinolino)dimethoxysilane,
bis(4-methylperhydroquinolino)dimethoxysilane,
bis(5-methylperhydroquinolino)dimethoxysilane,
bis(6-methylperhydroquinolino)dimethoxysilane,
bis(7-methylperhydroquinolino)dimethoxysilane,
bis(8-methylperhydroquinolino)dimethoxysilane,
bis(9-methylperhydroquinolino)dimethoxysilane,
bis(10-methylperhydroquinolino)dimethoxysilane and the like.

Specific examples of bis(dimethyl-substituted-perhydroquinolino)dimethoxysilane compounds include,
bis(2,3-dimethylperhydroquinolino)dimethoxysilane,
bis(2,4-dimethylperhydroquinolino)dimethoxysilane,
bis(2,5-dimethylperhydroquinolino)dimethoxysilane,
bis(2,6-dimethylperhydroquinolino)dimethoxysilane,
bis(2,7-dimethylperhydroquinolino)dimethoxysilane,
bis(2,8-dimethylperhydroquinolino)dimethoxysilane,
bis(2,9-dimethylperhydroquinolino)dimethoxysilane,
bis(2,10-dimethylperhydroquinolino)dimethoxysilane,
bis(3,4-dimethylperhydroquinolino)dimethoxysilane,
bis(3,5-dimethylperhydroquinolino)dimethoxysilane,
bis(3,6-dimethylperhydroquinolino)dimethoxysilane,
bis(3,7-dimethylperhydroquinolino)dimethoxysilane,
bis(3,8-dimethylperhydroquinolino)dimethoxysilane,
bis(3,9-dimethylperhydroquinolino)dimethoxysilane,
bis(3,10-dimethylperhydroquinolino)dimethoxysilane,
bis(4,5-dimethylperhydroquinolino)dimethoxysilane,
bis(4,6-dimethylperhydroquinolino)dimethoxysilane,
bis(4,7-dimethylperhydroquinolino)dimethoxysilane,
bis(4,8-dimethylperhydroquinolino)dimethoxysilane,
bis(4,9-dimethylperhydroquinolino)dimethoxysilane,
bis(4,10-dimethylperhydroquinolino)dimethoxysilane,
bis(5,6-dimethylperhydroquinolino)dimethoxysilane,
bis(5,7-dimethylperhydroquinolino)dimethoxysilane,
bis(5,8-dimethylperhydroquinolino)dimethoxysilane,
bis(5,9-dimethylperhydroquinolino)dimethoxysilane,
bis(5,10-dimethylperhydroquinolino)dimethoxysilane,
bis(6,7-dimethylperhydroquinolino)dimethoxysilane,
bis(6,8-dimethylperhydroquinolino)dimethoxysilane,
bis(6,9-dimethylperhydroquinolino)dimethoxysilane,
bis(6,10-dimethylperhydroquinolino)dimethoxysilane,
bis(7,8-dimethylperhydroquinolino)dimethoxysilane,
bis(7,9-dimethylperhydroquinolino)dimethoxysilane,
bis(7,10-dimethylperhydroquinolino)dimethoxysilane,
bis(8,9-dimethylperhydroquinolino)dimethoxysilane,
bis(9,10-dimethylperhydroquinolino)dimethoxysilane and the like.

Specific examples of bis(trimethyl-substituted-perhydroquinolino)dimethoxysilane compounds include,
bis(2,3,4-trimethylperhydroquinolino)dimethoxysilane, bis(3,4,5-trimethylperhydroquinolino)dimethoxysilane,
bis(4,5,6-trimethylperhydroquinolino)dimethoxysilane,
bis(5,6,7-dimethylperhydroquinolino)dimethoxysilane,
bis(6,7,8-trimethylperhydroquinolino)dimethoxysilane,
bis(7,8,9-trimethylperhydroquinolino)dimethoxysilane,
bis(8,9,10-trimethylperhydroquinolino)dimethoxysilane
  and the like.
Further, there can be exemplified compounds of
(perhydroquinolino)(2-methylperhydroquinolino)dimethoxysilane,
(perhydroquinolino)(3-methylperhydroquinolino)dimethoxysilane,
(perhydroquinolino)(4-methylperhydroquinolino) dimethoxylsilane,
(perhydroquinolino)(5-methylperhydroquinolino)dimethoxysilane,
(perhydroquinolino)(6-methylperhydroquinolino)dimethoxysilane,
(perhydroquinolino)(7-methylperhydroquinolino)dimethoxysilane,
(perhydroquinolino)(8-methylperhydroquinolino)dimethoxysilane,
(perhydroquinolino)(9-methylperhydroquinolino)dimethoxysilane,
(perhydroquinolino)(10-methylperhydroquinolino) dimethoxysilane and the like.
Among these compounds,
bis(perhydroquinolino)dimethoxysilane is preferred.
Examples of the compound represented by the general formula 24, there can be mentioned
bis(perhydroisoquinolino)dimethoxysilane and the like.
Examples of the compounds of
bis(methyl-substituted-perhydroisoquinolino)dimethoxysilanes include, bis(1-methylperhydroisoquinolino) dimethoxysilane,
bis(3-methylperhydroisoquinolino)dimethoxysilane,
bis(4-methylperhydroisoquinolino)dimethoxysilane,
bis(5-methylperhydroisoquinolino)dimethoxysilane,
bis(6-methylperhydroisoquinolino)dimethoxysilane,
bis(7-methylperhydroisoquinolino)dimethoxysilane,
bis(8-methylperhydroisoquinolino)dimethoxysilane,
bis(9-methylperhydroisoquinolino)dimethoxysilane,
bis(10-methylperhydroisoquinolino)dimethoxysilane and the like.
Examples of the compounds of
bis(dimethyl-substituted-perhydroisoquinolino)dimethoxysilane include,
bis(1,3-dimethylperhydroisoquinolino)dimethoxysilane,
bis(1,4-dimethylperhydroisoquinolino)dimethoxysilane,
bis(1,5-dimethylperhydroisoquinolino)dimethoxysilane,
bis(1,6-dimethylperhydroisoquinolino)dimethoxysilane,
bis(1,7-dimethylperhydroisoquinolino)dimethoxysilane,
bis(1,8-dimethylperhydroisoquinolino)dimethoxysilane,
bis(1,9-dimethylperhydroisoquinolino)dimethoxysilane,
bis(1,10-dimethylperhydroisoquinolino)dimethoxysilane,
bis(3,4-dimethylperhydroisoquinolino)dimethoxysilane,
bis(3,5-dimethylperhydroisoquinolino)dimethoxysilane,
bis(3,6-dimethylperhydroisoquinolino)dimethoxysilane,
bis(3,7-dimethylperhydroisoquinolino)dimethoxysilane,
bis(3,8-dimethylperhydroisoquinolino)dimethoxysilane,
bis(3,9-dimethylperhydroisoquinolino)dimethoxysilane,
bis(3,10-dimethylperhydroisoquinolino)dimethoxysilane,
bis(4,5-dimethylperhydroisoquinolino)dimethoxysilane,
bis(4,6-dimethylperhydroisoquinolino)dimethoxysilane,
bis(4,7-dimethylperhydroisoquinolino)dimethoxysilane,
bis(4,8-dimethylperhydroisoquinolino)dimethoxysilane,
bis(4,9-dimethylperhydroisoquinolino)dimethoxysilane,
bis(4,10-dimethylperhydroisoquinolino)dimethoxysilane,
bis(5,6-dimethylperhydroisoquinolino)dimethoxysilane,
bis(5,7-dimethylperhydroisoquinolino)dimethoxysilane,
bis(5,8-dimethylperhydroisoquinolino)dimethoxysilane,
bis(5,9-dimethylperhydroisoquinolino)dimethoxysilane,
bis(5,10-dimethylperhydroisoquinolino)dimethoxysilane,
bis(6,7-dimethylperhydroisoquinolino)dimethoxysilane,
bis(6,8-dimethylperhydroisoquinolino)dimethoxysilane,
bis(6,9-dimethylperhydroisoquinolino)dimethoxysilane,
bis(6,10-dimethylperhydroisoquinolino)dimethoxysilane,
bis(7,8-dimethylperhydroisoquinolino)dimethoxysilane,
bis(7,9-dimethylperhydroisoquinolino)dimethoxysilane,
bis(7,10-dimethylperhydroisoquinolino)dimethoxysilane,
bis(8,9-dimethylperhydroisoquinolino)dimethoxysilane,
bis(8,10-dimethylperhydroisoquinolino)dimethoxysilane,
bis(9,10-dimethylperhydroisoquinolino)dimethoxysilane
  and the like.
Examples of the compounds of
bis(trimethyl-substituted-perhydroisoquinolino)dimethoxysilane include,
bis(1,3,4-trimethylperhydroisoquinolino)dimethoxysilane,
bis(3,4,5-trimethylperhydroisoquinolino)dimethoxysilane,
bis(4,5,6-trimethylperhydroisoquinolino)dimethoxysilane,
bis(5,6,7-trimethylperhydroisoquinolino)dimethoxysilane,
bis(6,7,8-trimethylperhydroisoquinolino)dimethoxysilane,
bis(7,8,9-trimethylperhydroisoquinolino)dimethoxysilane,
bis(8,9,10-trimethylperhydroisoquinolino)dimethoxysilane
  and the like.
Further, examples of the compounds of
(perhydroisoquinolino)(monomethyl-substituted perhydroisoquinolino)-dimethoxysilane include,
(perhydroisoquinolino)(2-methyl-perhydroisoquinolino) dimethoxysilane,
(perhydroisoquinolino)(3-methylperhydroisoquinolino) dimethoxysilane,
(perhydroisoquinolino)(4-methylperhydroisoquinolino) dimethoxysilane,
(perhydroisoquinolino)(5-methylperhydroisoquinolino) dimethoxysilane,
(perhydroisoquinolino)(6-methylperhydroisoquinolino) dimethoxysilane,
(perhydroisoquinolino)(7-methylperhydroisoquinolino) dimethoxysilane,
(perhydr-oisoquinolino)(8-methylperhydrosoquinolino) dimethoxysilane,
(perhydroisoquinolino)(9-methylperhydroisoquinolino) dimethoxysilane,
(perhydroisoquinolino)(10-methylperhydroisoquinolino) dimethoxysilane and the like.
Among these compounds,
bis(perhydroisoquinolino)dimethoxysilane is preferable.
Examples of the compounds represented by the general formula 25 include,
(perhydroquinolino)(perhydroisoquinolino)dimethoxysilane,
(perhydroquinolino)(1-methylperhydroisoquinolino) dimethoxysilane,
(perhydroquinolino)(3-methylperhydroisoquinolino) dimethoxysilane,
(perhydroquinolino)(4-methylperhydroisoquinolino) dimethoxysilane,
(perhydroquinolino)(5-methylperhydroisoquinolino) dimethoxysilane,
(perhydroquinolino)(6-methylperhydroisoquinolino) dimethoxysilane,
(perhydroquinolino)(7-methylperhydroisoquinolino) dimethoxysilane, (perhydroquinolino)(8-methylperhydroisoquinolino)dimethoxysilane,
(perhydroquinolino)(9-methylperhydroisoquinolino)dimethoxysilane,
(perhydroquinolino)(10-methylperhydroisoquinolino)dimethoxy silane,
(2-methylperhydroquinolino)(perhydroisoquinolino)dimethoxysilane,
(3-methylperhydroquinolino)(perhydroisoquinolino)dimethoxysilane,
(4-methylperhydroquinolino)(perhydroisoquinolino)dimethoxysilane,
(5-methylperhydroquinolino)(perhydroisoquinolino)dimethoxysilane,
(6-methylperhydroquinolino)(perhydroisoquinolino)dimethoxysilane,
(7-methylperhydroquinolino)(perhydroisoquinolino)dimethoxysilane,
(8-methylperhydroquinolino)(perhydroisoquinolino)dimethoxysilane,
(9-methylperhydroquinolino)(perhydroisoquinolino)dimethoxysilane,
(10-methylperhydroquinolino)(perhydroisoquinolino)dimethoxysilane,
(2-methylperhydroquinolino)(1-methylperhydroisoquinolino)dimethoxysilane,
(3-methylperhydroquinolino)(3-methylperhydroisoquinolino)dimethoxysilane,
(4-methylperhydroquinolino)(4-methylperhydroisoquinolino)dimethoxysilane,
(5-methylperhydroquinolino)(5-methylperhydroisoquinolino)dimethoxysilane,
(6-methylperhydroquinolino)(6-methylperhydroisoquinolino)dimethoxysilane,
(7-methylperhydroquinolino)(7-methylperhydroisoquinolino)dimethoxysilane,
(8-methylhydroquinolino)(8-methylhydroisoquinolino)dimethoxysilane,
(9-methylhydroquinolino)(9-methylhydroisoquinolino)dimethoxysilane,
(10-methylhydroquinolino)(10-methylhydroisoquinolino)dimethoxysilane and the like.

Among these compounds, (perhydroquinolino)(perhydroisoquinolino)dimethoxysilane is preferable.

Examples of the compounds represented by the general formula 26 include,
bis(1,2,3,4-tetrahydroquinolino)dimethoxysilane and the like.

Examples of the compounds of bis(methyl-substituted-1,2,3,4-tetrahydroquinolino)dimethoxysilane include,
bis(2-methyl-1,2,3,4-tetrahydroquinolino)dimethoxysilane,
bis(3-methyl-1,2,3,4-tetrahydroquinolino)dimethoxysilane,
bis(4-methyl-1,2,3,4-tetrahydroquinolino)dimethoxysilane.
bis(6-methyl-1,2,3,4-tetrahydroquinolino)dimethoxysilane,
bis(7-methyl-1,2,3,4-tetrahydroquinolino)dimethoxysilane,
bis(8-methyl-1,2,3,4-tetrahydroquinolino)dimethoxysilane,
bis(9-methyl-1,2,3,4-tetrahydroquinolino)dimethoxysilane and the like.

Examples of the compounds of bis(dimethyl-substituted-1,2,3,4-tetrahydroquinolino)dimethoxysilane include,
bis(2,3-dimethyl-1,2,3,4-tetrahydroquinolino)dimethoxysilane,
bis(2,4-dimethyl-1,2,3,4-tetrahydroquinolino)dimethoxysilane,
bis(2,6-dimethyl-1,2,3,4-tetrahydroquinolino)dimethoxysilane,
bis(2,7-dimethyl-1,2,3,4-tetrahydroquinolino)dimethoxysilane,
bis(2,8-dimethyl-1,2,3,4-tetrahydroquinolino)dimethoxysilane,
bis(2,9-dimethyl-1,2,3,4-tetrahydroquinolino)dimethoxysilane,
bis(3,4-dimethyl-1,2,3,4-tetrahydroquinolino)dimethoxysilane,
bis(3,6-dimethyl-1,2,3,4-tetrahydroquinolino)dimethoxysilane,
bis(3,7-dimethyl-1,2,3,4-tetrahydroquinolino)dimethoxysilane,
bis(3,8-dimethyl-1,2,3,4-tetrahydroquinolino)dimethoxysilane,
bis(3,9-dimethyl-1,2,3,4-tetrahydroquinolino)dimethoxysilane,
bis(4,6-dimethyl-1,2,3,4-tetrahydroquinolino)dimethoxysilane,
bis(4,7-dimethyl-1,2,3,4-tetrahydroquinolino)dimethoxysilane,
bis(4,8-dimethyl-1,2,3,4-tetrahydroquinolino)dimethoxysilane,
bis(4,9-dimethyl-1,2,3,4-tetrahydroquinolino)dimethoxysilane,
bis(6,7-dimethyl-1,2,3,4-tetrahydroquinolino)dimethoxysilane,
bis(6,8-dimethyl-1,2,3,4-tetrahydroquinolino)dimethoxysilane,
bis(6,9-dimethyl-1,2,3,4-tetrahydroquinolino)dimethoxysilane,
bis(7,8-dimethyl-1,2,3,4-tetrahydroquinolino)dimethoxysilane,
bis(7,9-dimethyl-1,2,3,4-tetrahydroquinolino)dimethoxysilane,
bis(8,9-dimethyl-1,2,3,4-tetrahydroquinolino)dimethoxysilane and the like.

Examples of the compounds of bis(trimethyl-substituted-1,2,3,4-tetrahydroquinolino)dimethoxysilane include,
bis(2,3,4-trimethyl-1,2,3,4-tetrahydroquinolino)dimethoxysilane,
bis(2,3,6-trimethyl-1,2,3,4-tetrahydroquinolino)dimethoxysilane,
bis(2,3,7-trimethyl-1,2,3,4-tetrahydroquinolino)dimethoxysilane,
bis(2,3,8-trimethyl, 2,3,4-tetrahydroquinolino)dimethoxysilane,
bis(2,3,9-trimethyl-1,2,3,41-tetrahydroquinolino)dimethoxysilane,
bis(3,4,6-trimethyl-1,2,3,4-tetrahydroquinolino)dimethoxysilane,
bis(3,4,7-trimethyl-1,2,3,4-tetrahydroquinolino)dimethoxysilane,
bis(3,4,8-trimethyl-1,2,3,4-tetrahydroquinolino)dimethoxysilane,
bis(3,4,9,-trimethyl-1,2,3,4-tetrahydroquinolino)dimethoxysilane,
bis(4,6,7-trimethyl-1,2,3,4-tetrahydroquinolino)dimethoxysilane,
bis(4,6,8-trimethyl-1,2,3,4-tetrahydroquinolino)dimethoxysilane,
bis(4,6,9-trimethyl-1,2,3,4-tetrahydroquinolino)dimethoxysilane,
bis(6,7,8-trimethyl-1,2,3,4-tetrahydroquinolino)dimethoxysilane, bis(6,7,9-trimethyl-1,2,3,4-tetrahydroquinolino)dimethoxysilane,
bis(7,8,9-trimethyl-1,2,3,4-tetrahydroquinolino)dimethoxysilane and the like.

Examples of the compounds of bis(tetramethyl-substituted-1,2,3,4-tetrahydroquinolino) dimethoxysilane include,
bis(2,3,4,6-tetramethyl-1,2,3,4-tetrahydroquinolino) dimethoxysilane,
bis(2,3,4,7-tetramethyl-1,2,3,4-tetrahydroquinolino) dimethoxysilane,
bis(2,3,4,8-tetramethyl-1,2,3,4-tetrahydroquinolino) dimethoxysilane,
bis(2,3,4,9-tetramethyl-1,2,3,4-tetrahydroquinolino) dimethoxysilane,
bis(3,4,6,7-tetramethyl-1,2,3,4-tetrahydroquinolino) dimethoxysilane,
bis(3,4,6,8,-tetramethyl-1,2,3,4-tetrahydroquinolino) dimethoxysilane,
bis(3,4,6,9,-tetramethyl-1,2,3,4-tetrahydroquinolino) dimethoxysilane,
bis(4,6,7,8,-tetramethyl-1,2,3,4-tetrahydroquinolino) dimethoxysilane,
bis(4,6,7,9,-tetramethyl-1,2,3,4-tetrahydroquinolino) dimethoxysilane,
bis(6,7,8,9-tetramethyl-1,2,3,4-tetrahydroquinolino) dimethoxysilane and the like.

Among these compounds, bis(1,2,3,4-tetrahydroquinolino)dimethoxysilane is preferred.

Examples of the organosilicon compounds represented by the general formula 21 include, the compounds represented by the general formula 31 or 32.

Formula 31

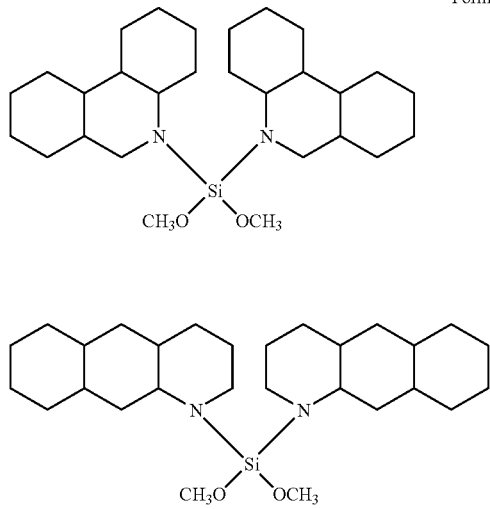

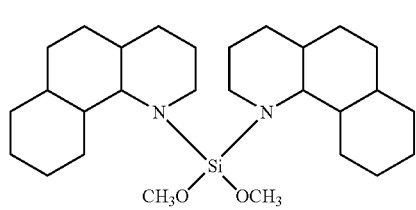

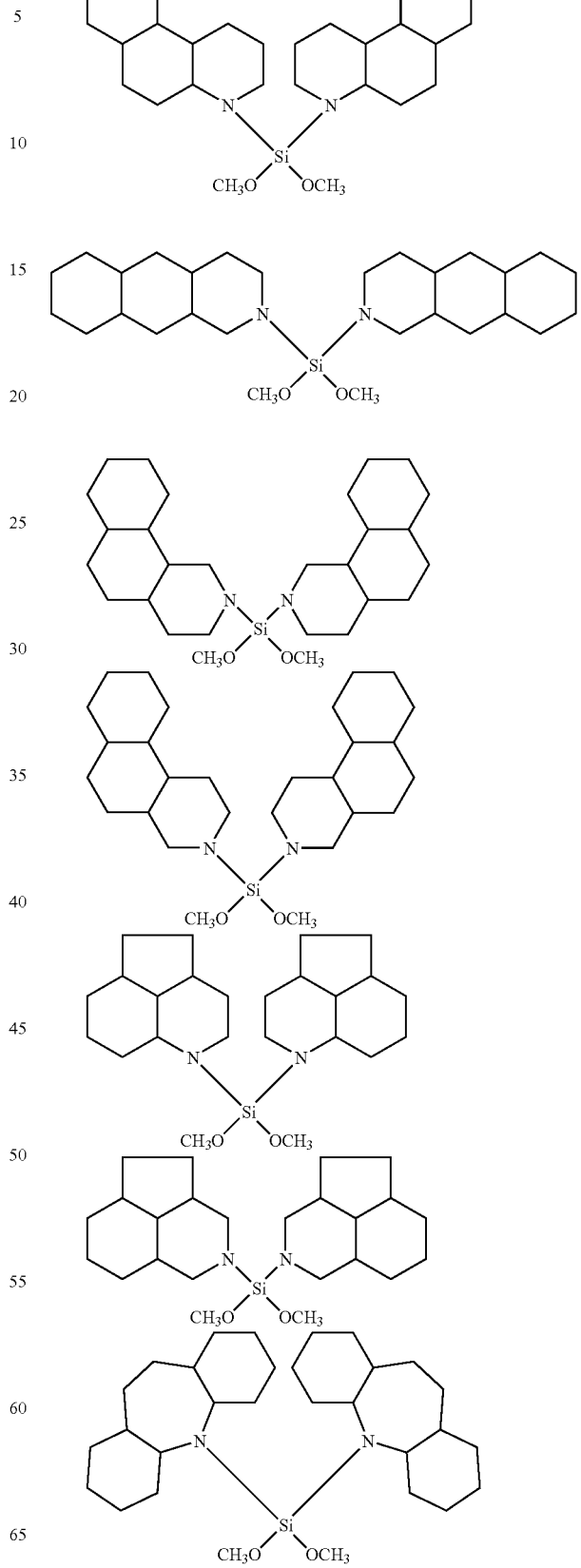

-continued

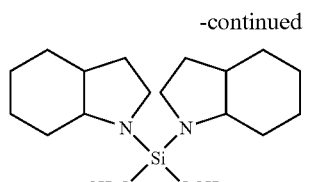
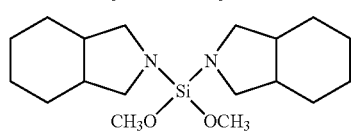
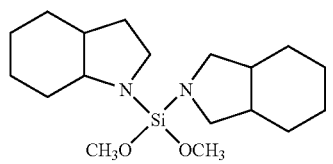
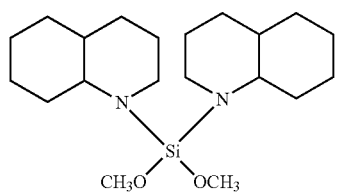
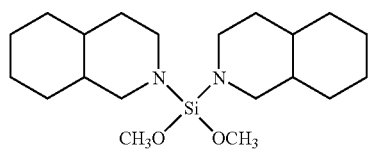
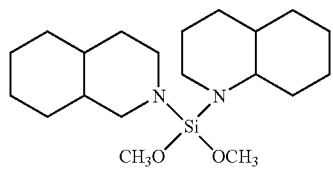
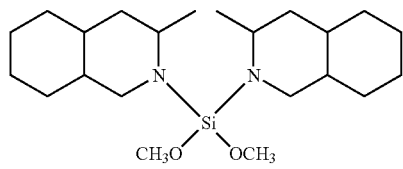
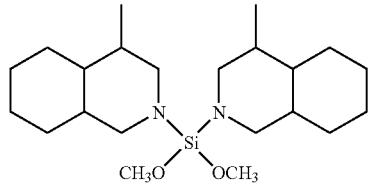
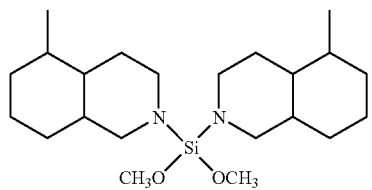

Formula 32

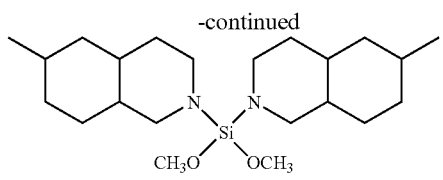
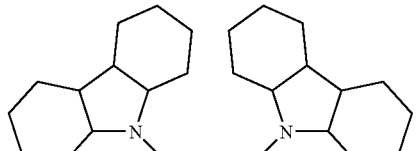
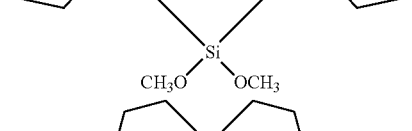
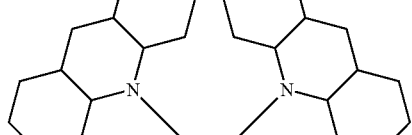
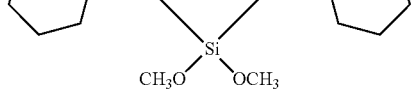

Examples of the organosilicon compounds represented by the general formula 22 include, the perhydroquinolino compounds represented by the general formula 33, the perhydroisoquinolino compounds represented by the general formula 34 and the like.

Formula 33

Formula 34

In the above formulas, $R^4$ represents a substituted group on the saturated, cyclic skeleton of the general formula R.sup.3N and is hydrogen atom, or a saturated or unsaturated aliphatic hydrocarbon group having 1 to 24 carbon atoms. The preferable examples includes hydrogen atom, methyl group, ethyl group, n-propyl group, iso-propyl group, n-butyl group, iso-butyl group, ter-butyl group, sec-butyl group, and the like. The number of hydrocarbon groups substituted on the saturated cyclic structure of R.sup.3 N may be 1 or more.

Examples of the perhydroquinolinosilane compounds represented by the general formula 33 include,
ethyl(perhydroquinolino)dimethoxysilane,
n-propyl(perhydroquinolino)dimethoxysilane,
iso-propyl(perhydroquinolino)dimethoxysilane,
n-butyl(perhydroquinolino)dimethoxysilane,
iso-butyl(perhydroquinolino)dimethoxysilane,
ter-butyl(perhydroquinolino)dimethoxysilane,
sec-butyl(perhydroquinolino)dimethoxysilane,
n-pentyl(perhydroquinolino)dimethoxysilane,
iso-pentyl(perhydroquinolino)dimethoxysilane, cyclopentyl(perhydroquinolino)dimethoxysilane,
n-hextyl(perhydroquinolino)dimethoxysilane,
cyclohextyl(perhydroquinolino)dimethoxysilane,
thextyl(perhydroquinolino)dimethoxysilane,
n-octyl(perhydroquinolino)dimethoxysilane,
phenyl(perhydroquinolino)dimethoxysilane,
piperidino(perhydroquinolino)dimethoxysilane,
dimethylamino(perhydroquinolino)dimethoxysilane,
iso-propoxy(perhydroquinolino)dimethoxysilane,
ter-butoxy(perhydroquinolino)dimethoxysilane and the like.

Examples of the methyperhydroquinolinosilane compounds include, ethyl(2-methylperhydroquinolino)dimethoxysilane,
n-propyl(2-methylperhydroquinolino)dimethoxysilane,
iso-propyl(2-methylperhydroquinolino)dimethoxysilane,
n-butyl(2-methylperhydroquinolino)dimethoxysilane,
iso-butyl(2-methylperhydroquinolino)dimethoxysilane,
ter-butyl(2-methylperhydroquinolino)dimethoxysilane,
sec-butyl(2-methylperhydroquinolino)dimethoxysilane,
n-pentyl(2-methylperhydroquinolino)dimethoxysilane,
iso-pentyl(2-methylperhydroquinolino)dimethoxysilane,
cyclopentyl(2-methylperhydroquinolino)dimethoxysilane,
n-hextyl(2-methylperhydroquinolino)dimethoxysilane,
cyclohextyl(2-methylperhydroquinolino)dimethoxysilane,
thextyl(2-methylperhydroquinolino)dimethoxysilane,
n-octyl(2-methylperhydroquinolino)dimethoxysilane,
n-detyl(2-methylperhydroquinolino)dimethoxysilane,
2-decalino(2-methylperhydroquinolino)dimethoxysilane,
phenyl(2-methylperhydroquinolino)dimethoxysilane,
iso-propyl(3-methylperhydroquinolino)dimethoxysilane,
iso-propyl(4-methylperhydroquinolino)dimethoxysilane,
iso-propyl(5-methylperhydroquinolino)dimethoxysilane,
iso-propyl(6-methylperhydroquinolino)dimethoxysilane,
iso-propyl(7-methylperhydroquinolino)dimethoxysilane,
iso-propyl(8-methylperhydroquinolino)dimethoxysilane,
iso-propyl(9-methylperhydroquinolino)dimethoxysilane,
iso-propyl(10-methylperhydroquinolino)dimethoxysilane and the like.

Among the above-mentioned compounds, ethyl(perhydroquinolino)dimethoxysilane,
n-propyl(perhydroquinolino)dimethoxysilane,
iso-propyl(perhydroquinolino)dimethoxysilane,
n-butyl(perhydroquinolino)dimethoxysilane,
iso-butyl(perhydroquinolino)dimethoxysilane,
ter-butyl(perhydroquinolino)dimethoxysilane,
sec-butyl(perhydroquinolino)dimethoxysilane,
cyclopentyl(perhydroquinolino)dimethoxysilane,
n-hextyl(perhydroquinolino)dimethoxysilane,
piperidino(perhydroquinolino)dimethoxysilane,
ter-butoxy(perhydroquinolino)dimethoxysilane,
diethylamino(perhydroquinolino)dimethoxysilane and the like are preferred.

Examples of the perhydroisoquinolinosilane compounds represented by the general formula 34 include,
ethyl(perhydroisoquinolino)dimethoxysilane,
n-propyl(perhydroisoquinolino)dimethoxysilane,
iso-propyl(perhydroisoquinolino)dimethoxysilane,
n-butyl(perhydroisoquinolino)dimethoxysilane,
iso-butyl(perhydroisoquinolino)dimethoxysilane,
ter-butyl(perhydroisoquinolino)dimethoxysilane,
sec-butyl(perhydroisoquinolino)dimethoxysilane,
n-pentyl(perhydroisoquinolino)dimethoxysilane,
iso-pentyl(perhydroisoquinolino)dimethoxysilane,
cyclopentyl(perhydroisoquinolino)dimethoxysilane,
n-hextyl(perhydroisoquinolino)dimethoxysilane,
cyclohextyl(perhydroisoquinolino)dimethoxysilane,
thextyl(perhydroisoquinolino)dimethoxysilane,
n-octyl(perhydroisoquinolino)dimethoxysilane,
n-detyl(perhydroisoquinolino)dimethoxysilane,
2-decalino(perhydroisoquinolino)dimethoxysilane,
phenyl(perhydroisoquinolino)dimethoxysilane,
piperidino(perhydroisoquinolino)dimethoxysilane,
dimethylamino(perhydroisoquinolino)dimethoxysilane,
iso-propoxy(perhydroisoquinolino)dimethoxysilane,
ter-butoxy(perhydroisoquinolino)dimethoxysilane and the like.

Examples of the methyperhydroisoquinolinosilane compounds include,
ethyl(2-methylperhydroisoquinolino)dimethoxysilane,
n-propyl(2-methylperhydroisoquinolino)dimethoxysilane,
iso-propyl(2-methylperhydroisoquinolino)dimethoxysilane,
n-butyl(2-methylperhydroisoquinolino)dimethoxysilane,
iso-butyl(2-methylperhydroisoquinolino)dimethoxysilane,
ter-butyl(2-methylperhydroisoquinolino)dimethoxysilane,
sec-butyl(2-methylperhydroisoquinolino)dimethoxysilane,
n-pentyl(2-methylperhydroisoquinolino)dimethoxysilane,
iso-pentyl(2-methylperhydroisoquinolino)dimethoxysilane,
cyclopentyl(2-methylperhydroisoquinolino)dimethoxysilane,
n-hextyl(2-methylperhydroisoquinolino)dimethoxysilane,
cyclohextyl(2-methylperhydroisoquinolino)dimethoxysilane,
thextyl(2-methylperhydroisoquinolino)dimethoxysilane,
n-octyl(2-methylperhydroisoquinolino)dimethoxysilane,
n-detyl(2-methylperhydroisoquinolino)dimethoxysilane,
2-decalino(2-methylperhydroisoquinolino)dimethoxysilane,
phenyl(2-methylperhydroisoquinolino)dimethoxysilane,
piperidino(2-methylperhydroisoquinolino)dimethoxysilane,
dimethylamino(2-methylperhydroisoquinolino)dimethoxysilane,
iso-propoxy(2-methylperhydroisoquinolino)dimethoxysilane,
ter-butoxy(2-methylperhydroisoquinolino)dimethoxysilane,
iso-propyl(3-methylperhydroisoquinolino)dimethoxysilane,
iso-propyl(4-methylperhydroisoquinolino)dimethoxysilane,
iso-propyl(5-methylperhydroisoquinolino)dimethoxysilane,
iso-propyl(6-methylperhydroisoquinolino)dimethoxysilane,
iso-propyl(7-methylperhydroisoquinolino)dimethoxysilane,
iso-propyl(8-methylperhydroisoquinolino)dimethoxysilane,
iso-propyl(9-methylperhydroisoquinolino)dimethoxysilane,
iso-propyl(10-methylperhydroisoquinolino)dimethoxysilane and the like.

Among the above-mentioned compounds,
ethyl(perhydroisoquinolino)dimethoxysilane,
n-propyl(perhydroisoquinolino)dimethoxysilane,
iso-propyl(perhydroisoquinolino)dimethoxysilane,
n-butyl(perhydroisoquinolino)dimethoxysilane,
iso-butyl(perhydroisoquinolino)dimethoxysilane,
ter-butyl(perhydroisoquinolino)dimethoxysilane,
sec-butyl(perhydroisoquinolino)dimethoxysilane,
cyclopentyl(perhydroisoquinolino)dimethoxysilane,
n-hextyl(perhydroisoquinolino)dimethoxysilane,
piperidino(perhydroisoquinolino)dimethoxysilane,
ter-butoxy(perhydroisoquinolino)dimethoxysilane,
diethylamino(perhydroisoquinolino)dimethoxysilane and the like are preferred.

Specific examples of the organosilicon compounds represent by the general formula 22 include a compound represented by the chemical structural formula 35 or 36.

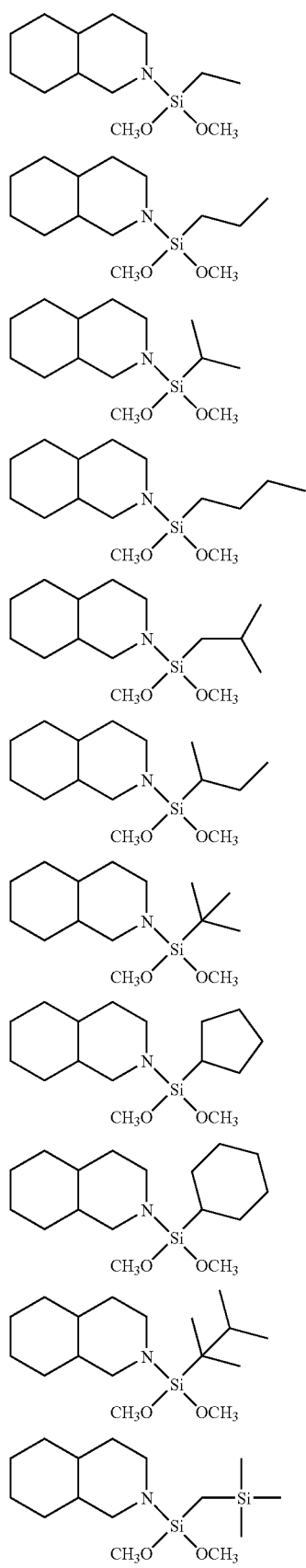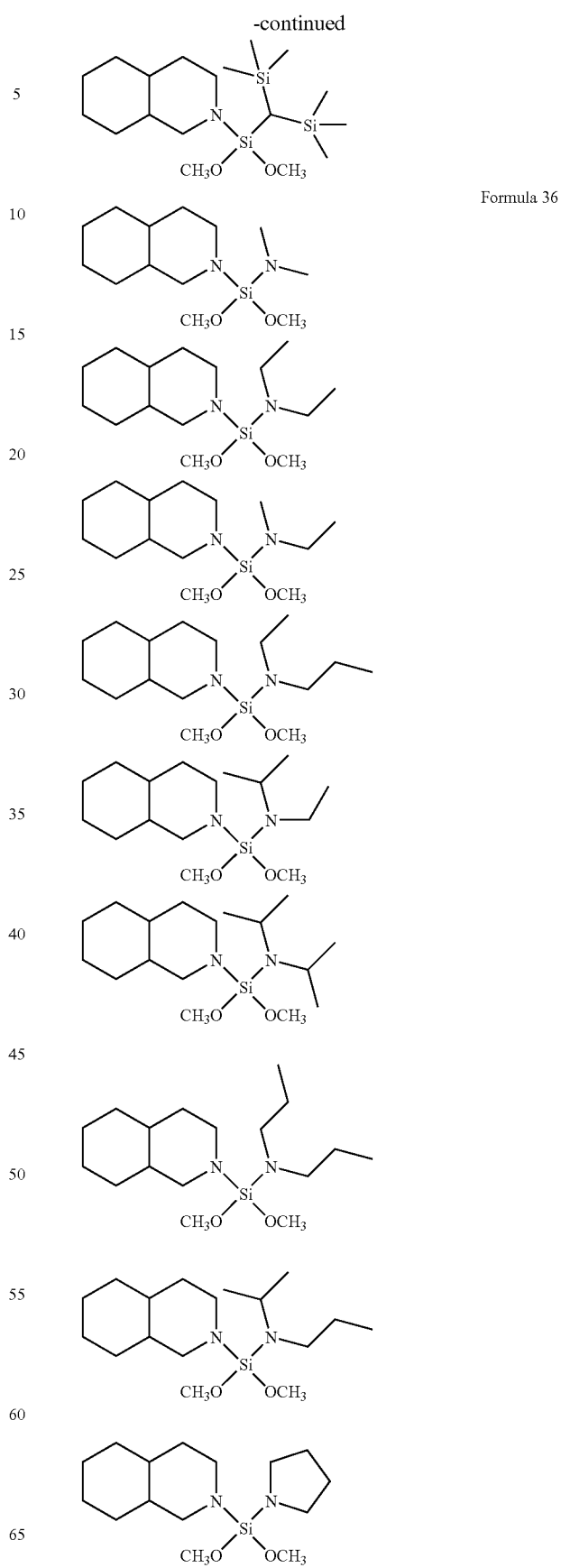
Formula 36

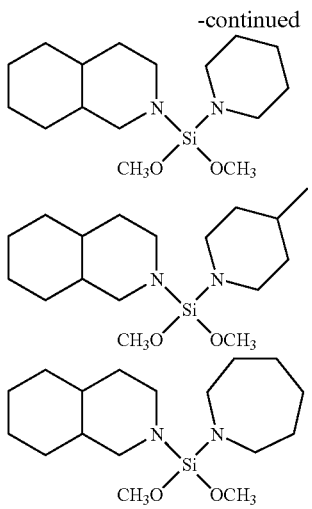

Examples of the above-mentioned organosilicon compounds having two saturated polycyclic amino groups have geometrical isomers since the polycyclic amino group may have a cis- or trans-isomer. That is, there exist isomers such as (trans-polycyclic amino)(trans-polycyclic amino)dialkoxysilane, (cis-polycyclic amino)(cis-polycyclic amino)dialkoxysilane, (trans-polycyclic amino) (cis-polycyclic amino)dialkoxysilane. Specific examples thereof include, bis(trans-perhydroquinolino)dimethoxysilane, bis(cis-perhydroquinolino)dimethoxysilane, bis(trans-perhydroisoquinolino)dimethoxysilane, bis(cis-perhydroisoquinolino)dimethoxysilane. Any of those isomers may be used as the constituent (D) in the present invention, singly or in the form of a mixture. Other organosilicon compounds, for example, existing organosilicon compounds, such as cyclohexylmethyldimethoxysilane;

dicyclopentyldimethoxysilane; di-isopropyldimethoxysilane; di-n-butyldimethoxysilane; and methyl-n-butyldimethoxysilane may be also employed as the constituent [D] of the present invention.

An organosilicon compound which is the catalyst constituent (D) represented by the formula 21 can be synthesized by reacting tetramethoxysilane or dichlorodimethoxysilane with 2 equivalent amounts of a magnesium salt or lithium salt of the secondary amine represented by the formula HNR. Further, the catalyst constituent (D) represented by the general formula 22 can be synthesized by reacting an alkyl trimethoxysilane or alkyl chlorodimethoxysilane with a magnesium salt or lithium salt of the secondary amine represented by the formula HNR.

When the constituents [C] and [D] are employed, they may be mixed previously or solely added in the polymerization system. A mixed molar ratio ([C]/[D]) is between 0.01 and 3, preferably between 0.02 and 2, and more preferably between 0.05 and 1.

The catalyst system consisting of the catalyst constituents [A], [B], [C] and [D] exhibits high catalyst activity and high hydrogen response. In addition, a produced α-olefin polymer has high stereoregularity and a wide molecular weight distribution. The molecular weight distribution has a ratio Mw/Mn derived from a weight-averaged molecular weight, Mw, and a number-averaged molecular weight, Mn, on a polystyrene basis in a GPC measurement. A value of the ratio is equal to or more than 10, preferably equal to or more than 12, and more preferably equal to or more than 15.

As the α-olefin polymer produced using the catalyst has a wide molecular weight distribution, it has a high melt viscoelasticity. Particularly, it is excellent in formation of films and the like as well as excellent in solidity of injected moldings, heat resistance, and mechanical physical properties such as tensile strength without any problem associated with appearance deficits of moldings typified with flow marks. The α-olefin polymer produced by the invention may be employed solely. In addition, it may be employed, as a compound material, in blend with other plastics or elastomers, and in combination with reinforcements for inorganic and organic fillers such as glass fibers and talc, and other crystal nucleus agents. It can provide excellent performance, not particularly limited, to automobile and household electric structural materials.

A conventional method of manufacturing α-olefin polymers with a high hydrogen response, high stereoregularity and wide molecular weight distribution is disclosed, for example, in JP-A 2000-63417. In propylene bulk polymerization, however, the conventional combination is difficult to achieve a molecular weight distribution of Mw/Mn=12 under the condition of total pressure of 3.8 MPa or below while maintaining a MFR of 120 and a stereoregularity of 98.5%. The use of the catalyst of the invention can achieve this target value. Copolymerization with ethylene or other α-olefins can produce a copolymer with good randomness and a high melt viscoelasticity.

The α-olefin polymer produced using the catalyst has a molecular weight distribution almost similar to that of an α-olefin polymer produced with a conventional titanium trichloride catalyst called the second generation catalyst with low polymerization reaction rate. Therefore, it has good moldability and no problem associated with appearance deficits of moldings typified with flow marks. The catalyst system for use in the invention can be employed as an alternative of the titanium trichloride catalyst. As it has a much higher polymerization reaction rate than that of the titanium trichloride catalyst, it can omit the step of removing catalytic residues from inside the polymer, or the step of deashing using a large amount of organic solvent, which is essentially required in the art. This is effective to simplify polymerization methodes and reduce production costs.

Method of Polymerizing α-Olefins

For achievement of the above object, the present invention is directed to an α-olefin polymerization method of polymerizing or copolymerizing α-olefins in the presence of the α-olefin polymerization or copolymerization catalyst. The polymerization in the method for polymerizing α-olefin according to the invention includes homopolymerization of α-olefins as well as copolymerization such as α-olefin propylene block copolymerization and α-olefin propylene random copolymerization.

The method of polymerizing α-olefins according to the present invention includes a slurry polymerization method, in which a nonpolar solvent such as propane, n-butane, n-pentane, n-hexane, n-heptane and n-octane is employed. It also includes a gas-phase polymerization method, in which a monomer in gas state is contact with a catalyst for polymerization; and a bulk polymerization method, in which a monomer in liquid state is employed as a solvent for polymerization therein. These polymerization methods may be performed by continuous polymerization or batch polymerization, and polymerization reaction may be performed in a single stage or a plurality of stages with combination of the above polymerization methods.

In the above polymerization methods, a polymerization pressure is 0.1 to 20 MPa, preferably 0.5 to 6 MPa, a polymerization temperature is 10 to 150° C., preferably 30 to 100° C., and more preferably 60 to 90° C., and a polymerization time is 0.1 to 10 hours, preferably 0.5 to 7 hours.

Through the use of the α-olefin polymerization or copolymerization catalyst according to the invention, in bulk polymerization under a reaction pressure of 3.8 MPa, propylene bulk polymerization under a hydrogen partial pressure equal to or less than 0.7 MPa is performed. In this case, it is possible to produce an α-olefin polymer having a MFR equal to or more than 400 measured at 230° C. with a weight of 2.16 kg in compliant with ASTM D1238 and having a meso-pentad fraction (mmmm) equal to or more than 98.5%.

The polymer may be employed in blend with other plastics or elastomers, and in easily mixture of reinforcements for inorganic and organic fillers such as glass fibers and talc, and other crystal nucleus agents. As the polymer has a small molecular weight, when it is melted and kneaded with an ethylene/propylene copolymer, an operation at a lower temperature is allowed with a high viscosity of the copolymer, which disperses the copolymer finely and uniformly more than it is kneaded at a higher temperature. In addition, it is possible to prevent a bleed-out phenomenon that can be often observed during melting and kneading. Thus, the present material is considered as an excellent compound material that can be employed for producing, not particularly limited to, automobile and household electric structural materials. When it is employed in the so-called linear polymerization to subsequently produce an ethylene/propylene copolymer after the production of the present polymer, an excellent effect can be shown.

Preferably, in the present invention the main polymerization of α-olefins is performed after prepolymerization of an ethylene or α-olefin in accordance with the above various polymerization methods. The prepolymerization is effective to improve the polymerization reaction rate, improve the stereoregularity of the polymer, and stabilize the morphology of the polymer.

In the method of prepolymerization, the solid catalyst constituent [A] is previously contacted with the organoaluminum compound constituent [B] and the organosilicon compound constituent [C] or with the organoaluminum compound constituent [B], the organosilicon compound constituent [C] and the organosilicon compound constituent [D] to polymerize a limited amount of ethylene or α-olefin to prepare a prepolymerized solid. In another case, without polymerization of ethylene or α-olefin, the solid catalyst constituent [A] is contacted with the organoaluminum compound constituent [B] and the organosilicon compound constituent [C] or with the organoaluminum compound constituent [B], the organosilicon compound constituent [C] and the organosilicon compound constituent [D] to prepare a preliminarily methoded solid.

In the present invention, the prepolymerized solid or the preliminarily methoded solid may be employed as the solid catalyst constituent in the main polymerization. In this case, during the main polymerization, the organosilicon compound constituent [C], or the organosilicon compound constituent [C] and the organosilicon compound constituent [D] can be omitted, and only the organosilicon compound constituent [D]can be omitted.

After prepolymerization in the presence of the catalyst consisting of the solid catalyst constituent [A], the organoaluminum compound constituent [B] and the organosilicon compound constituent [D], subsequent polymerization or copolymerization of an α-olefin may be performed with addition of the organosilicon compound constituent [C]. As the relatively expensive organosilicon compound constituent [D] is employed only during such the prepolymerization, even a small amount shows a sufficient effect thereof, resulting in reduced polymerization costs of α-olefins. Also in this case, the α-olefin polymer with a high stereoregularity, high melt fluidity and wide molecular weight distribution exhibits good moldability and excellent property against appearance deficits of moldings such as flow marks.

In the contact methoding of the invention, the constituents [A], [B] and [C]; the constituents [A], [B], [C] and [D]; or the constituents [A],[B] and[D] are mixed for reaction at 0-100° C. for 0.1-10 hours usually. Mixing order of the constituents is not limited particularly but a preferable one is found in order of the constituent [A], the constituent [B] and the constituent [C]; or in order of the constituent [A], the constituent [B], the constituent [C] and the constituent [D]. After the contact methoding, the solid is cleansed, filtered and separated in an inactive hydrocarbon solvent such as n-heptane, then it is employed as the solid catalyst constituent in the prepolymerization or the main polymerization.

The prepolymerization in the invention is achieved in the gas-phase polymerization method, the slurry polymerization method, and the bulk polymerization method. The solid produced through the prepolymerization is separated and then employed for the main polymerization, or it is successively subjected, without separation, to the main polymerization.

A prepolymerization time is usually 0.1 to 10 hours. Preferably, prepolymerization is continued until a prepolymer is produced by 0.1 to 100 g per 1 g of the catalyst solid constituent. If less than 0.1 g per 1 g of the catalyst solid constituent, the main polymerization reaction rate is not sufficient, resulting in much catalytic residues, and insufficient stereoregularity of the α-olefin polymer. If more than 100 g, the polymerization reaction rate and the crystallinity of the α-olefin polymer may be lowered possibly. A prepolymerization temperature is 0 to 100° C., preferably 10-70° C. in the presence of each catalyst constituent. When prepolymerization is performed at a high temperature over 50° C., it is preferable to reduce an ethylene or α-olefin concentration or shorten the polymerization time. Otherwise, it is difficult to control the production of the prepolymer by 0.1 to 100 g per 1 g of the catalyst solid constituent. In addition, the polymerization reaction rate may lower in the main polymerization, or the crystallinity of the α-olefin polymer produced may lower.

An amount of the organoaluminum compound constituent [B] during the prepolymerization is usually 0.5 to 1000 in Al/Ti molar ratio relative to titanium in the solid catalyst constituent [A], preferably 1 to 100. An amount of the organosilicon compound constituent [C] is usually 0.01 to 5 in Si/Al molar ratio relative to aluminum in the constituent [B], preferably 0.05 to 1. An amount of a mixed constituent of the organosilicon compound constituent [C] and the organosilicon compound constituent [D] is usually 0.01 to 1 in Si/Al molar ratio relative to an aluminum atom in the constituent [B], preferably 0.08 to 0.5. Hydrogen may be allowed to coexist during the prepolymerization, if required.

In the present invention, if the organoaluminum compound constituent [B] is employed during the main polymerization, an amount of the constituent [B] is usually 0.1 to 1500 in Al/Ti molar ratio relative to a titanium atom in the solid catalyst constituent [A], preferably 30 to 1000.

In the method of polymerizing α-olefins according to the invention, the organosilicon compound constituents [C] and [D] are added, during the main polymerization of the α-olefin, in addition to the organoaluminum compound constituent [B], to further improve the polymarization reaction rate and improve the stereoregularity of the polymer.

In the present invention, a chain transfer agent such as hydrogen may be employed. An amount of hydrogen to produce an α-olefin polymer with a desired stereoregularity, melting point and molecular weight can be determined appropriately based on a polymerization method and a polymerization condition. Usually, a hydrogen partial pressure is in a range equal to or below 3 PMa. In the present invention, to lower a heat seal temperature at a film, for the purpose of lowering a melting point and increasing transparency of the film, during polymerization of the α-olefin, a small amount of another α-olefin may be copolymerized.

α-Olefin Propylene Block Copolymerization

In order to improve the low-temperature impact strength of moldings from the α-olefin polymer, the so-called block copolymer can be produced by copolymerizing two or more kinds of α-olefins after homopolymerization of the α-olefin or copolymerization of the α-olefin with another α-olefin.

In production of an α-olefin propylene block copolymer, a specific method includes a first step of homopolymerizing propylene, and a second step of block copolymerizing a combined monomer of propylene with an α-olefin other than propylene. The first and second steps may include multi-stage polymerization. The propylene produced in the first step has a melt flow rate ranging 0.1 to 2000, preferably 30 to 1000, and more preferably 100 to 700.

The propylene produced in the first step has a stereoregularity in meso-pentad fraction (mmmm) of 97.5% or more, preferably 98.0% or more, and more preferably 98.2% or more. The melting point (Tm) is 161° C. or more, preferably 162° C. or more, and more preferably 162.5° C. or more. The copolymer of propylene with the α-olefin other than propylene produced in the second step has a proportion (or block ratio=(Yield of the copolymer of propylene with the α-olefin other than propylene/Total polymer amount)×100). The proportion has a range within 1 to 50 wt. %, preferably 5 to 35 wt. %, and more preferably 20 to 30 wt. %.

The catalyst system of the invention provides good hydrogen response, high polymarization reaction rate, high stereoregularity of the produced α-olefin polymer, and high melt fluidity. Particularly, in production of an ethylene-propylene copolymer, a constituent of propylene homopolymer is employed 80 to 70 wt. %, and a constituent of random copolymer of propylene with the α-olefin other than propylene is employed 20 to 30 wt. %. In this case, after melting and kneading, the constituent of random copolymer of propylene with the α-olefin other than propylene does not bleed out of the surface of the α-olefin propylene copolymer in structure. Thus, it is possible to provide an α-olefin propylene copolymer having a sea-island structure. The present material with less bleed-out can be provided as a composition with less stickiness and improved handling ability, and as a commodity product with a further increased commercial value.

In the first step, hydrogen may be added as a chain transfer agent to adjust a molecular weight of the produced polymer, if required. An amount of hydrogen for production of the polymer having a desired stereoregularity (mmmm) and melt fluidity (MFR) can be determined appropriately based on a polymerization method and a polymerization condition. Generally, at a polymerization temperature, it corresponds to 0.005 to 1 MPa, preferably 0.01 to 0.7 MPa in gauge pressure.

In the present invention, contacting order of each catalyst constituent is not limited particularly. Though it is not much preferable to allow the organosilicon compound of the constituent [C] to directly contact with the solid catalyst of the constituent [A] only.

After the production of a crystalline polymer through propylene homopolymerization at the first step, propylene and an α-olefin other than propylene are subsequently copolymerized in gas-phase at the second step to produce a propylene block copolymer while the above catalyst system is not inactivated.

The rubber-like copolymer of propylene and the α-olefin other than propylene produced at the second step has a proportion of 3 to 50 wt. % generally, and more preferably 5 to 40 wt. % on the basis of the amount of the entire block copolymer. Preferably, the α-olefin other than propylene in the rubber-like copolymer has a proportion of 10 to 50 wt. %.

Hydrogen may be added to copolymerize in the second step. During the ethylene/propylene gas-phase polymerization reaction in the catalyst system of the present invention, methods of elevating a reaction temperature, adding an organoaluminum constituent, increasing a monomer pressure, determining different polymerization times for the first and second steps, and adding another donor constituent are generally known to improve polymarization reaction rate. In addition, coexistence of hydrogen can greatly improve polymarization reaction rate compared to the conventional catalyst system while maintaining high stereoregularity and high melt fluidity. As a result, an α-olefin polymer with high solidity and excellent melt fluidity can be produced at a higher productivity.

The polymerization pattern of the invention may include a first step of bulk polymerization, in which a monomer in liquid state is employed as a solvent for polymerization therein; and a second step of gas-phase polymerization, in which a monomer in gas state is contact with a catalyst.

Preferably, the bulk polymerization may be performed under such condition of temperature and pressure that can maintain the propylene monomer in liquid state. A polymerization temperature is generally 30 to 90° C., preferably 50 to 80° C. A polymerization time generally ranges from 5 minutes to 5 hours.

The gas-phase polymerization may be performed under such condition of temperature and pressure that can maintain gaseous state after introduction of a mixed monomer of propylene and another α-olefin. The α-olefin includes non-cyclic mono-olefins, such as ethylene, butene-1,3-methylbutene-1,3-methylpentene-1, 4-methylpentene-1, hexyene-1,4-methylhexyene-1, octene-1, styrene, 2-methystyrene, 3-methylstyrene, 4-methylstyrene, vinylcyclohexane, vinylcyclopentane, 2-vinylnaphthalene, and 9-vinylanthracene; cyclicmono-olefins, such as cyclopentene, cyclohexene, and norbornene; and diolefins, such as dicyclopentadiene, 5-ethylidenenorbornene-2,4-vinylcyclohexene, and 1,5-hexadiene.

A copolymerization pressure generally ranges from atmospheric pressure to 3 MPa, preferably from atmospheric pressure to 1.5 MPa. A polymerization temperature generally ranges between 30 to 95° C., preferably between 40 to 80° C. A polymerization time generally ranges from 30 minutes to 10 hours, preferably between 1 to 5 hours.

A catalyst solid consisting essentially of magnesium, titanium, a halogen element and an electron donor can be employed as the solid catalyst constituent [A]. In such the case, a limited amount of propylene may be prepolymerized prior to polymerization in the first step using the solid catalyst constituent [A] in the presence of the organoaluminum compound constituent [B] and the organosilicon compound constituent [C]. The prepolymerized solid or the prepolymerized and then cleansed solid may be employed in the main polymerization to improve polymerization reaction rate per solid catalyst and stereoregularity of the polymer.

In the present invention, if the prepolymerized solid is employed as the solid catalyst constituent in the main polymerization, the constituent [C] can be omitted from the main polymerization. The method and time of prepolymerization are same as those described above.

The gas-phase polymerization of propylene with the α-olefin other than propylene performed subsequent to the homopolymerization of propylene produces a rubber constituent or a copolymer of propylene with the α-olefin other than propylene. The copolymer can be obtained as a copolymer that has a high α-olefin content, a high molecular weight, and good randomness. This block copolymer has an excellent low-temperature characteristic, solidity and impact resistance.

α-Olefin Propylene Random Copolymerization

The α-olefin polymerization or copolymerization catalyst according to the present invention can be employed in random copolymerization of a mixed monomer of propylene with an α-olefin other than propylene.

The random copolymerization of the mixed monomer of propylene with the α-olefin other than propylene includes a slurry polymerization method, in which a nonpolar solvent is employed, such as propane, butane, hexane, heptane and octane. It also includes a gas-phase polymerization method, in which a monomer in gaseous state is employed for polymerization; and a bulk polymerization method, in which a monomer in liquid state is employed as a solvent. These polymerization methods may be performed by continuous polymerization or batch polymerization.

In the present invention, propylene and at least one α-olefin are copolymerized to produce a copolymer. Alternatively, propylene and one α-olefin other than propylene may be copolymerized or propylene and two or more kinds of α-olefins other than propylene may be copolymerized. The α-olefin other than propylene includes ethylene, 1-butene, 3-methyl-1-butene, 3-methyl-1-pentene, 1-hexyene, vinyl cyclohexane, cyclopentene, cycloheptene, norbornene, and 5-ethyl-2-norbornene. Among those, ethylene, 1-butene, 3-methyl-1-butene, 3-methyl-1-pentene, 1-hexyene and others are preferable. When propylene and one α-olefin other than propylene are copolymerized, the other α-olefin is employed by preferably 0.005 to 0.17 mole, and more preferably 0.01 to 0.1 mole per one mole of propylene.

A copolymerization pressure ranges between 0.1 to 20 MPa, preferably 1 to 6 MPa. A polymerization temperature ranges between 10 to 150° C., preferably 30 to 100° C., and more preferably 60 to 90° C. Polymerization time generally ranges between 0.1 to 10 hours, preferably 0.5 to 7 hours. Hydrogen may be added as a chain transfer agent to adjust a molecular weight of the produced polymer, if required. An amount of hydrogen to produce an α-olefin polymer with a desired stereoregularity and molecular weight can be determined appropriately based on a polymerization method and a polymerization condition. In the present invention, after propylene or other α-olefins are prepolymerized in accordance with the above various polymerization methods, the prepolymerization catalyst may be employed for main polymerization. Preferably, in the presence of the constituents [A] and [B], or the constituents [A], [B] and [C], propylene or other α-olefins can be prepolymerized. A prepolymerization ratio ranges between 0.1 to 300, preferably 0.5 to 100 in weight ratio of Prepolymer/Constituent [A]. The prepolymerization can be performed in gas-phase, slurry and bulk methods. The solid constituent produced in prepolymerization may be separated and then employed in main polymerization or may be employed without separation in main polymerization. If the prepolymer is employed as a catalyst constituent in main polymerization, the constituent [C] may be omitted from main polymerization.

The catalyst system of the invention provides good hydrogen response, high polymerization reaction rate, high stereoregularity of the produced α-olefin polymer, good randomness, and high melt fluidity. In particular, as hydrogen response is greatly improved compared to the conventional catalyst system, an α-olefin with high solidity and excellent melt fluidity can be produced without sacrifice of productivity. A highly transparent film can be produced because of good randomness. A film with no atactic constituent-originated stickiness can be produced because of high stereoregularity of the polypropylene part. The use of the catalyst system of the invention can provide production of an ethylene-propylene block copolymer with a block ratio of 10 to 50 wt. %, and production of a reactor-made TPO. The α-olefin polymer produced in the invention may be employed solely. In addition, it may be employed as a compound material, in blend with other plastics or elastomers, and in combination with reinforcements for inorganic and organic fillers such as glass fibers and talc, and other crystal nucleus agents. It can provide excellent performance, not particularly limited, to automobile and household electric structural materials.

Effects of the Invention

As described above, the catalyst system of the invention provides good hydrogen response, high polymerization reaction rate, high stereoregularity of the produced α-olefin polymer, and high melt fluidity.

As the α-olefin polymer produced in the invention has high stereoregularity, it provides excellent mechanical physical properties such as solidity, heat resistance and tensile strength of injected moldings. This is beneficial to thin the injected moldings. The good melt fluidity thereof can shorten an injected molding cycle and eliminate appearance deficits of moldings typified by flow marks of injected moldings. A block copolymer with other α-olefins can impart an impact resistance and produce an α-olefin polymer with good melt fluidity and excellently balanced solidity and impact resistance. The α-olefin polymer produced in the invention may be employed solely. In addition, it may be employed as a compound material, in blend with other plastics or elastomers, and in combination with reinforcements for inorganic and organic fillers such as glass fibers and talc, and other crystal nucleus agents. It can provide excellent performance, not particularly limited, to automobile and household electric structural materials.

The use of the catalyst of the invention on α-olefin polymerization allows production of an α-olefin polymer with high hydrogen response, high polymarization reaction rate, high stereoregularity, and good melt fluidity. In particular, as hydrogen response is greatly improved compared to the conventional catalyst system, an α-olefin with high solidity and excellent melt fluidity can be produced without sacrifice of productivity. The use of the catalyst system of the invention can provide production of an ethylene-propylene block copolymer with a block ratio of 10 to 50 wt. %, and production of a reactor-made TPO.

THE BEST MODE FOR CARRYING OUR THE INVENTION

Figure 1:
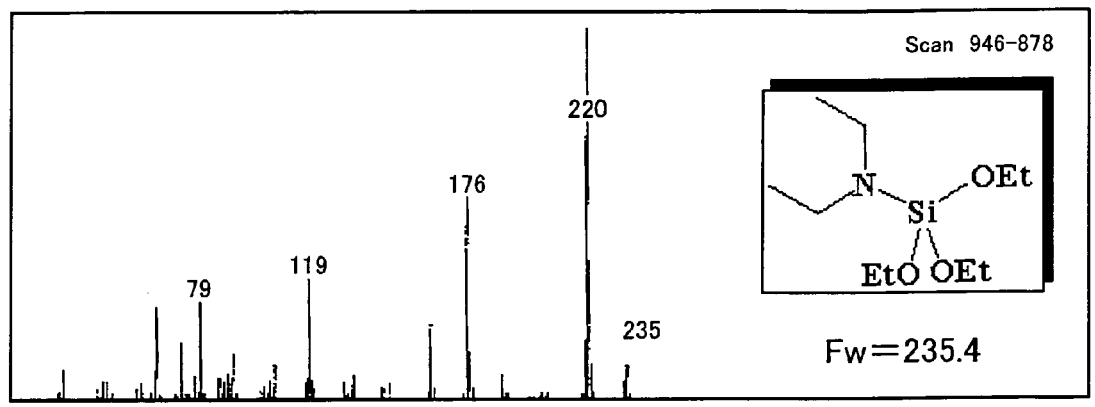
FIG. 1 shows a mass spectrum of a synthesized constituent [C] or diethylamino triethoxy silane.

Examples of the present invention shown in Tables 1-4 will now be described below. The present invention is not limited to the description of below-described Examples.

TABLE 1

| | Compound | Formula |
|---|---|---|
| Example 1 | Diethylaminotriethoxysilane | |
| Example 2 | Diethylaminotri-n-propoxysilane | |
| Example 3 | Dimethylaminotriethoxysilane | |
| Example 4 | Di-n-propylaminotriethoxysilane | |
| Example 5 | Methylethylaminotriethoxysilane | |
| Example 6 | Methyl-n-propylaminotriethoxysilane | |

TABLE 2

| | Compound | Formula |
|---|---|---|
| Example 7 | Ethyl-n-propylaminotriethoxysilane | |
| Example 8 | Ethylisopropylaminotriethoxysilane | |
| Example 9 | t-butylaminotriethoxysilane | |
| Example 10 | Di-isopropylamintriethoxysilane | |

TABLE 2-continued

| | Compound | Formula |
|---|---|---|
| Example 11 | (Perhydro-isoquinolino)triethoxysilane | [structure: perhydroisoquinoline-N-Si(OEt)₃] |
| Example 12 | (1,2,3,4-tetrahydro-isoquinolino)triethoxysilane | [structure: 1,2,3,4-tetrahydroisoquinoline-N-Si(OEt)₃] |
| Example 13 | (Perhydroquinolino)triethoxysilane | [structure: perhydroquinoline-N-Si(OEt)₃] |

TABLE 3

| | Compound | Formula |
|---|---|---|
| Example 14 | (1,2,3,4-tetrahydro-quinolino)triethoxysilane | [structure: 1,2,3,4-tetrahydroquinoline-N-Si(OEt)₃] |
| Example 15 | (Perhydro-isoquinolino)tri-n-propoxysilane | [structure: perhydroisoquinoline-N-Si(OnPr)₃] |
| Example 16 | Octamethyleneiminotriethoxysilane | [structure: octamethyleneimine-N-Si(OEt)₃] |
| Example 17 | (Perhydro-isoquinolino)tri(isopropoxy)silane | [structure: perhydroisoquinoline-N-Si(OiPr)₃] |
| Example 18 | (Perhydro-isoquinolino)tri-n-butoxysilane | [structure: perhydroisoquinoline-N-Si(OnBu)₃] |

TABLE 4

| | Compound | Formula |
|---|---|---|
| Comparative example 1 | Ethyl(diethyl-amino)dimethoxysilane | [structure: Et₂N-Si(Et)(OMe)₂] |
| Comparative example 2 | Ethyl(diethylamino)diethoxysilane | [structure: Et₂N-Si(Et)(OEt)₂] |
| Comparative example 3 | Cyclohexyl(methyl)dimethoxysilane | [structure: Cy-Si(Me)(OMe)₂] |
| Comparative example 4 | Ethyl(piperidino)dimethoxysilane | [structure: piperidino-Si(Et)(OMe)₂] |
| Comparative example 5 | Di(piperidino)dimethoxysilane | [structure: (piperidino)₂Si(OMe)₂] |
| Comparative example 6 | Di-isopropyldimethoxysilane | [structure: (iPr)₂Si(OMe)₂] |
| Comparative example 7 | Dicyclopentyldimethoxysilane | [structure: (cyclopentyl)₂Si(OMe)₂] |

TABLE 5

| | Compound | Formula |
|---|---|---|
| Comparative example 8 | Ethyl(perhydro-isoquinolino)dimethoxy Silane | [structure: perhydroisoquinoline-N-Si(Et)(OMe)₂] |
| Comparative example 9 | Bis(perhydro-isoquinolino)dimethoxy Silane | [structure: (perhydroisoquinoline-N)₂Si(OMe)₂] |

TABLE 5-continued

| Compound | | Formula |
|---|---|---|
| Comparative example 10 | Ethylazacyclononanodimethoxysilane | (structure: azacyclononane ring with N–Si(OMe)(OMe)Et) |
| Comparative example 11 | Di-n-butyldimethoxysilane | nBu–Si(OMe)(OMe)–nBu |
| Comparative example 12 | Bis(diethylamino)dimethoxysilane | (Et₂N)₂Si(OMe)₂ |
| Comparative example 13 | Dicyclopentyldimethoxysilane | (cyclopentyl)₂Si(OMe)₂ |

EXAMPLE 1

Figure 2:
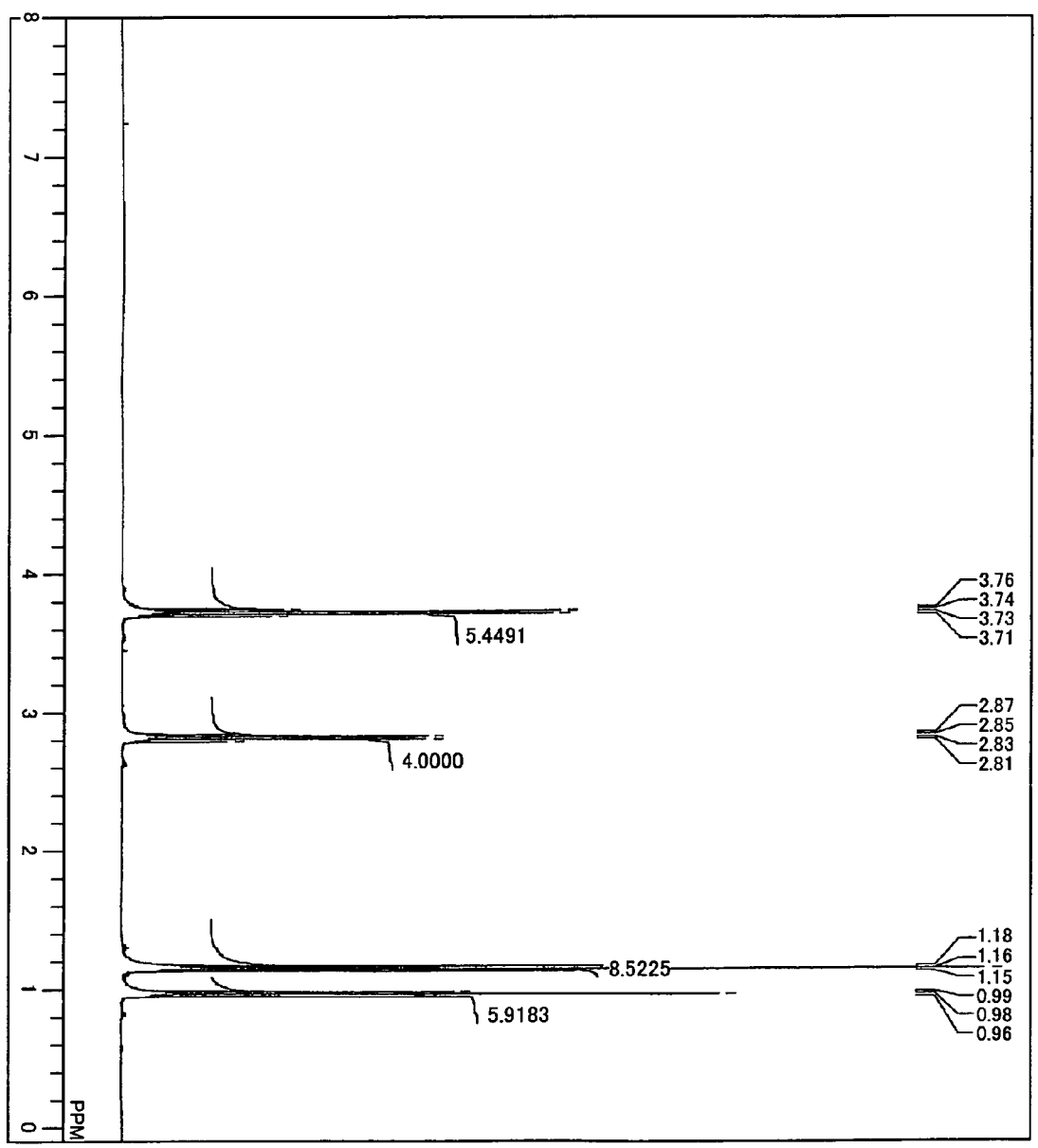
FIG. 2 shows a diagram of NMR employed for identification of a synthesized constituent [C] or diethylamino triethoxy silane.

Diethylaminotriethoxysilane was synthesized as Example 1 in the following manner. First, into a four-necked flask (volume of 1 L) equipped with a magnet seal agitator and a dropping funnel, a 100 mL of toluene, a 10 mL of tetrahydro furan, and a 14.6 g (0.2 mol) of diethylamine were introduced and then mixed and agitated. A Grignard reagent (titer=1.71 mol/L) is on the other hand supplied by 129 mL (0.22 mol) into the dropping funnel. Thereafter, while agitating, the Grignard reagent is dropped from the dropping funnel into the flask at room temperature (air-cooling), spending 30 minutes. After completion of dropping, agitating was performed at 60° C. for one hour for Grignard exchange reaction. Then, a 41.7 g (0.2 mol) of tetraethoxysilane previously introduced into the dropping funnel is dropped into the flask, spending 15 minutes. After completion of dropping, a reaction was performed at 60° C. for 2 hours. At this moment, a solid of magnesium ethoxy chloride deposited in the flask. The reacted solution was partly extracted to confirm the generation of the target product by gas chromatography. Then, in nitrogen ambient, the reacted solution in the flask was entirely transferred therefrom to a container equipped with a G4 glass filter for pressure filtration with low-pressure nitrogen (0.01 MPa). The filtered residue (magnesium ethoxy chloride) was cleansed and filtered with toluene repeatedly until the target product could not be confirmed in the filtrate. The filtrate and the mixed solution of the filtered residue and the cleanser were condensed under reduced pressure to settle and remove solvent constituents such as toluene, and subsequently distilled and purified to restore the target product. The target product is a liquid with a colorless transparent appearance, which has a boiling point of 57.5° C./5 mmHg, and a GC purity of 98.0%. The target product is identified by gas-mass chromatography, of which mass spectrum is shown in FIG. 1, and NMR is shown in FIG. 2.

EXAMPLE 2

Diethylaminotri-n-propoxysilane was synthesized as Example 2. This synthesis was performed in the same manner as the synthesizing method of Example 1 except for the use of n-propoxysilane 52.9 g instead of the tetraethoxysilane 41.7 g. The target product is a liquid with a colorless transparent appearance, which has a boiling point of 72.0° C./5 mmHg, and a GC purity of 97.0%.

EXAMPLE 3

Dimethylaminotriethoxysilane was synthesized as Example 3. This synthesis was performed in the same manner as the synthesizing method of Example 1 except for the use of dimethylamine 9.0 g instead of the diethylamine 14.6 g. The target product is a liquid with a colorless transparent appearance, which has a boiling point of 81.0° C./48 mmHg, and a GC purity of 95.0%.

EXAMPLE 4

Di-n-propylaminotriethoxysilane was synthesized as Example 4. This synthesis was performed in the same manner as the synthesizing method of Example 1 except for the use of di-n-propylamine 20.2 g instead of the diethylamine 14.6 g. The target product is a liquid with a colorless transparent appearance, which has a boiling point of 65.0° C./5 mmHg, and a GC purity of 96.1%.

EXAMPLE 5

Methylethylaminotriethoxysilane was synthesized as Example 5. This synthesis was performed in the same manner as the synthesizing method of Example 1 except for the use of methylethylamine 11.8 g instead of the diethylamine 14.6 g. The target product is a liquid with a colorless transparent appearance, which has a boiling point of 57.0° C./6 mmHg, and a GC purity of 98.2%.

EXAMPLE 6

Methyl-n-propylaminotriethoxysilane was synthesized as Example 6. This synthesis was performed in the same manner as the synthesizing method of Example 1 except for the use of methyl-n-propylamine 14.6 g instead of the diethylamine 14.6 g. The target product is a liquid with a colorless transparent appearance, which has a boiling point of 58.5° C./5 mmHg, and a GC purity of 97.6%.

EXAMPLE 7

Ethyl-n-propylaminotriethoxysilane was synthesized as Example 7. This synthesis was performed in the same manner as the synthesizing method of Example 1 except for the use of ethyl-n-propylamine 17.4 g instead of the diethylamine 14.6 g. The target product is a liquid with a colorless transparent appearance, which has a boiling point of 85.0° C./4 mmHg, and a GC purity of 99.5%.

EXAMPLE 8

Ethylisopropylaminotriethoxysilane was synthesized as Example 8. This synthesis was performed in the same manner as the synthesizing method of Example 1 except for the use of ethylisopropylamine 17.4 g instead of the diethylamine 14.6 g. The target product is a liquid with a colorless transparent appearance, which has a boiling point of 62.0° C./5 mmHg, and a GC purity of 98.0%.

EXAMPLE 9

T-butylaminotriethoxysilane was synthesized as Example 9. This synthesis was performed in the same manner as the synthesizing method of Example 1 except for the use of t-butylamine 14.6 g instead of the diethylamine 14.6 g. The target product is a liquid with a colorless transparent appearance, which has a boiling point of 31.0° C./0.4 mmHg, and a GC purity of 96.6%.

EXAMPLE 10

Di-isopropylaminotriethoxysilane was synthesized as Example 10. This synthesis was performed in the same manner as the synthesizing method of Example 1 except for the use of di-isopropylamine 20.2 g instead of the diethylamine 14.6 g. The target product is a liquid with a colorless transparent appearance, which has a boiling point of 60.0° C./0.5 mmHg, and a GC purity of 98.0%.

EXAMPLE 11

Figure 3:
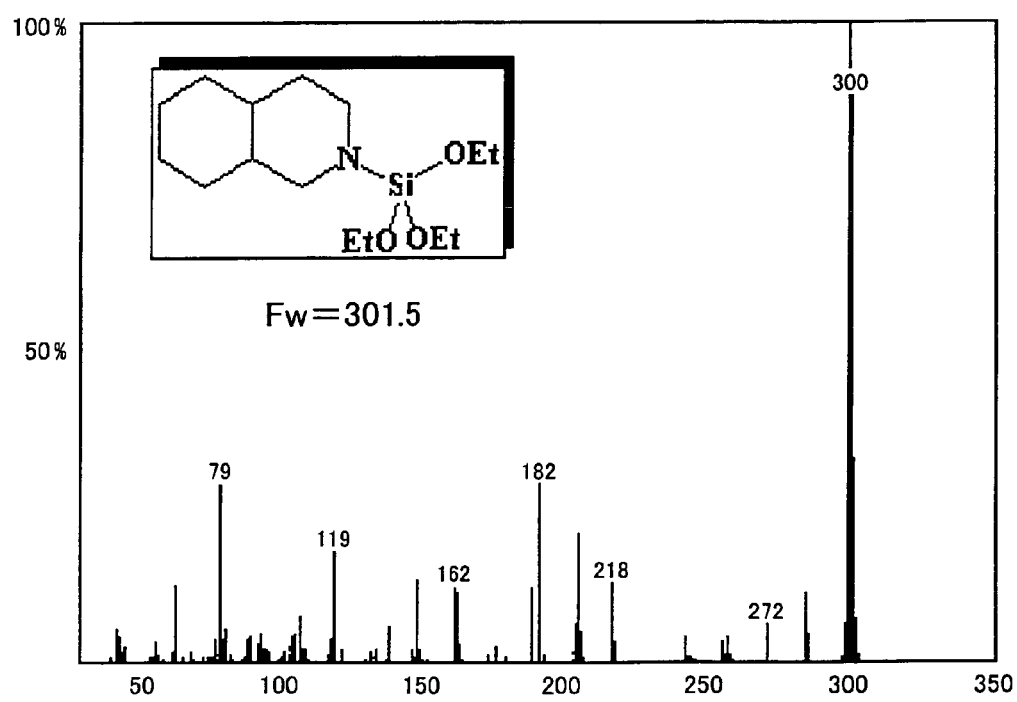
FIG. 3 shows a mass spectrum of a synthesized constituent [C] or (perhydro isoquinolino)triethoxy silane.

(Perhydro isoquinolino)triethoxysilane was synthesized as Example 11 in the following manner. In nitrogen ambient, into a four-necked flask (volume of 1 L) equipped with a magnet seal agitator and a dropping funnel, a 100 mL of toluene, 10 mL of tetrahydro furan, and 27.8 g (0.2 mol) of perhydro isoquinoline (trans=100%) were introduced and then mixed and agitated. A Grignard reagent (titer=1.71 mol/L) is on the other hand supplied by 129 mL (0.22 mol) into the dropping funnel. Thereafter, while agitating, the Grignard reagent is dropped from the dropping funnel into the flask at room temperature (air-cooling), spending 30 minutes. After completion of dropping, the temperature was elevated up to 60° C., and agitating was performed for one hour for Grignard exchange reaction. Then, 41.7 g (0.2 mol) of tetraethoxy silane previously introduced into the dropping funnel is dropped into the flask, spending 15 minutes. After completion of dropping, a reaction was further performed at 60° C. for 2 hours. At this moment, a solid of magnesium ethoxy chloride deposited in the flask. The reacted solution was partly extracted to confirm the generation of the target product by gas chromatography. Then, in nitrogen ambient, the reacted solution in the flask was entirely transferred therefrom to a container equipped with a G4 glass filter for pressure filtration with low-pressure nitrogen (0.01 MPa). The filtered residue (magnesium ethoxy chloride) was cleansed and filtered with toluene repeatedly until the target product could not be confirmed in the filtrate. The filtrate and the mixed solution of the filtered residue and the cleanser were condensed under reduced pressure to settle and remove solvent constituents such as toluene, and subsequently distilled and purified to restore the target product. The target product is a liquid with a colorless transparent appearance, which has a boiling point of 127° C./0.5 mmHg, and a GC purity of 99.6%. The target product is identified by gas-mass chromatography, of which mass spectrum is shown in FIG. 3.

EXAMPLE 12

Figure 4:
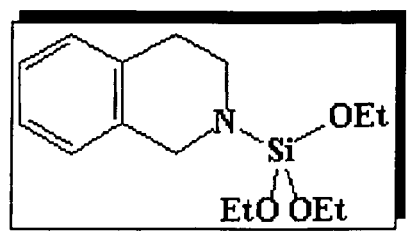
FIG. 4 shows a mass spectrum of a synthesized constituent [C] or (1,2,3,4-tetrahydro isoquinolino)triethoxy silane.
Figure 4:
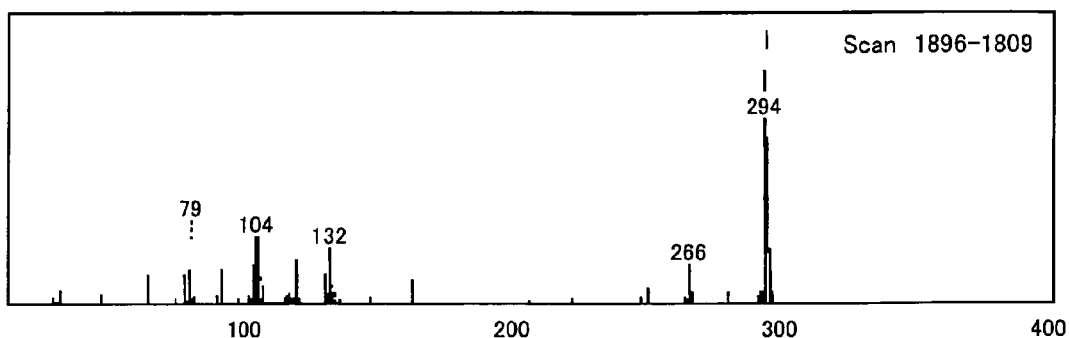

(1,2,3,4-tetrahydroisoquinolino)triethoxysilane was synthesized as Example 12. This synthesis was performed in the same manner as the synthesizing method of Example 11 except for the use of 1,2,3,4-tetrahydroisoquinoline 24 g instead of the perhydroisoquinoline 27.8 g. The target product is a liquid with a colorless transparent appearance, which has a boiling point of 152° C./1 mmHg, and a GC purity of 97.9%. The target product is identified by gas-mass chromatography, of which mass spectrum is shown in FIG. 4.

EXAMPLE 13

(Perhydroquinolino)triethoxysilane was synthesized as Example 13. This synthesis was performed in the same manner as the synthesizing method of Example 11 except for the use of perhydroquinoline 27.8 g instead of the perhydroisoquinoline 27.8 g. The target product is a liquid with a colorless transparent appearance, which has a boiling point of 151° C./1 mmHg, and a GC purity of 96.3%.

EXAMPLE 14

(1,2,3,4-tetrahydroquinolino)triethoxysilane was synthesized as Example 14. This synthesis was performed in the same manner as the synthesizing method of Example 11 except for the use of 1,2,3,4-tetrahydroquinoline 24.0 g instead of the perhydro isoquinoline 27.8 g. The target product is a liquid with a colorless transparent appearance, which has a boiling point of 150° C./1 mmHg, and a GC purity of 98.5%.

EXAMPLE 15

(Perhydroisoquinolino)tri-n-propoxysilane was synthesized as Example 15. This synthesis was performed in the same manner as the synthesizing method of Example 11 except for the use of tetra-n-propoxysilane 52.9 g instead of the tetraethoxysilane 41.7 g. The target product is a liquid with a colorless transparent appearance, which has a boiling point of 120° C./0.1 mmHg, and a GC purity of 96.6%.

EXAMPLE 16

Octamethyleneiminotriethoxysilane was synthesized as Example 16. This synthesis was performed in the same manner as the synthesizing method of Example 11 except for the use of octamethyleneimine 25.5 g instead of the perhydroisoquinoline 27.8 g. The target product is a liquid with a colorless transparent appearance, which has a boiling point of 132° C./1 mmHg, and a GC purity of 98.7%.

EXAMPLE 17

(Perhydroisoquinolino)triisopropoxysilane was synthesized as Example 17. This synthesis was performed in the same manner as the synthesizing method of Example 11 except for the use of tetraisopropoxysilane 52.9 g instead of the tetraethoxy silane 41.7 g. The target product is a liquid with a colorless transparent appearance, which has a boiling point of 147° C./1 mmHg, and a GC purity of 96.8%.

EXAMPLE 18

(Perhydroisoquinolino)tri-n-butoxysilane was synthesized as Example 18. This synthesis was performed in the same manner as the synthesizing method of Example 11 except for the use of tetra n-butoxy silane 64.1 g instead of the tetraethoxy silane 41.7 g. The target product is a liquid with a colorless transparent appearance, which has a boiling point of 129° C./1 mmHg, and a GC purity of 99.4%.

COMPARATIVE EXAMPLES

Comparative example 1 employs ethyl(diethylamino) dimethoxysilane, which is described in the example of JP-A 8-3215. Comparative example 2 employs ethyl(diethylamino)diethoxysilane. Comparative example 3 employs cyclohexyl(methyl)dimethoxysilane, which is industrially available. Comparative example 4 employs ethyl(piperidino) dimethoxysilane, which is described in the example of JP-A 8-120021. Comparative example 5 employs di(piperidino) dimethoxysilane, which is described in the example of JP-A 8-143621. Comparative example 6 employs di-isopropyldimethoxysilane. Comparative example 7 employs dicyclopentyldimethoxysilane. Comparative example 8 employs ethyl(perhydroisoquinolino)dimethoxysilane. Comparative example 9 employs bis(perhydroisoquinolino)dimethoxysilane. Comparative example 8 employs ethylazacyclononanodimethoxysilane. Comparative example 11 employs di-n-butyldimethoxysilane. Comparative example 12 employs bis(diethylamino)dimethoxysilane. Comparative example 13 employs dicyclopentyldimethoxysilane.

In the following Experimental examples, the term polymerization reaction rate means an yield (kg) of the polymer obtained per 1 g of the solid catalyst.

Melt flow ratio (M.F.R.) is determined by measuring an amount by weight (g) of a polymer melted at a temperature of 230.degree. C. and under load of 2.16 kg for 10 minutes in accordance with the method prescribed in ASTM-D1238. H. I means the ratio (%) of weight of insoluble polymer to prepared polymer, when extraction test of polymer is made by using boiled n-heptane for 6 hours.

Melting point (Tm) is measured by use of DSC (model: ASC-5200, manufactured by Seiko Denshi Kohgyo, Co.). As to the measuring conditions, 10 mg of propylene polymer is heated at temperature from 23.degree. C. until 230.degree. C. with a temperature gradient of 10.degree. C. per minute, thereafter the polymer was kept as it is for 5 minutes, then the temperature was dropped from 230.degree. C. until 40.degree. C. with a temperature gradient of 5.degree. C. per minute. The melting point is measured as a point that the polymer thus treated is remelted by heating from 40.degree. C. until 230.degree. C. by temperature gradient of 10.degree. C. per minute.

Stereoregularity of polymer is determined from Mesopentad fraction (mmmm) (%) obtained by the microtacticity, which means one of the indications of stereoregularity of polymer is calculated from the ratio of peak strengths of .sup. $^{13}$C-NMR spectrum in accordance with the method described in "Macromolecules, Vol 8, page 687, (1975)". The .sup.13 C-NMR spectrum is measured by an apparatus of model EX400 (manufactured by JEOL Ltd.) at temperature of 130.degree. C. and a number of scan of 800, by using TMS. as the standard substance and o-dichlorobenzene as a solvent.

H.I indicates a proportion (Insoluble polymer weight/ Prepared polymer weight×100) after testing extraction of the polymer with a boiling n-heptane for six hours.

Molecular weight distribution of a polymer is calculated from the ratio (Mw/Mn) of weight-average molecular weight (Mw) and number-average molecular weight (Mn) and the rate (Mz/Mw) of z-average molecular weight (Mz) and weight-average molecular weight (Mw) which are determined by using polystyrene as the standard substance, an instrument of GPC (model:150CV type, manufactured by waters, & Co.), o-dichlorobenzene as the solvent, column of SHODEX, temperature at 145.degree. C., and concentration of 0.05% by weight.

Rubber constituent (room temperature p-xylene soluble constituent) wt. % was measured in the following manner. 5 g of block copolymer is dissolved in a 500 ml of p-xylene at 135° C. spending one hour, then slowly cooled down, and left at room temperature over one night. Next, p-xylene soluble and insoluble constituents were centrifuged to deposit the soluble constituent with acetone, then filtered through a glass filter under reduced pressure, and the deposited product was dried under reduced pressure at 60° C. for five hours. The filtered and separated rubber constituent was weighed to calculate the rubber constituent wt. %.

The rubber constituent ethylene content and the room temperature p-xylene insoluble constituent ethylene content were measured in the following manner. A sample was heated and dissolved on a hot press heat plate, then pressurized and cooled, and quenched during water bathing to mold an approximately 30µ film. This film is measured for peaks at 974 cm$^{-1}$ and 720 cm$^{-1}$ with an infrared spectrophotometer to calculate the ethylene content based on a previously formed analytical curve.

Inherent viscosity [η] of the rubber constituent was measured in the following manner. 20 mg of sample was accurately measured and fed into a volumetric flask of 25 ml, then 20 mg of decaline that contains 0.3% BHT was added therein. The sample was completely dissolved at 135° C., and a 20 ml of the dissolved solution is transferred into a viscosimeter using a thermostatic bath set at 135° C. Then, a passage time between designated marked lines was measured to derive the inherent viscosity [η] of the rubber constituent using a viscosity equation.

Randomness (r1r2) was calculated from a peak intensity ratio of 13C-NMR spectrum ratio belonged based on K. Soga et al. POLYMER COMMUNICATIONS 32, No. 10, 310 (1991).

Ethylene content was calculated after forming a film by hot pressing a sample using a spacer with a thickness of 0.3 mm, and using an infrared spectrum technology to compensate for the thickness from a analytical curve.

EXPERIMENTAL EXAMPLE 1

Homopolymerization of Propylene

As Experimental example 1, homopolymerization of propylene was performed using α-olefin polymerization catalysts consisting of the solid catalyst constituent [A], the organoaluminum compound constituent [B], and the catalyst constituents [C] according to Examples 1-9. In Experimental example 1, as the solid catalyst constituent [A], a THC-JC type was employed, which is commercially available from Toho Catalyst. Ti content was 1.7 wt. %. As Comparative experiments, homopolymerization of propylene was performed using α-olefin polymerization catalysts consisting of the solid catalyst constituent [A], the organoaluminum compound constituent [B], and the catalyst constituents [C] according to Comparative examples 1-3.

Figure 5:
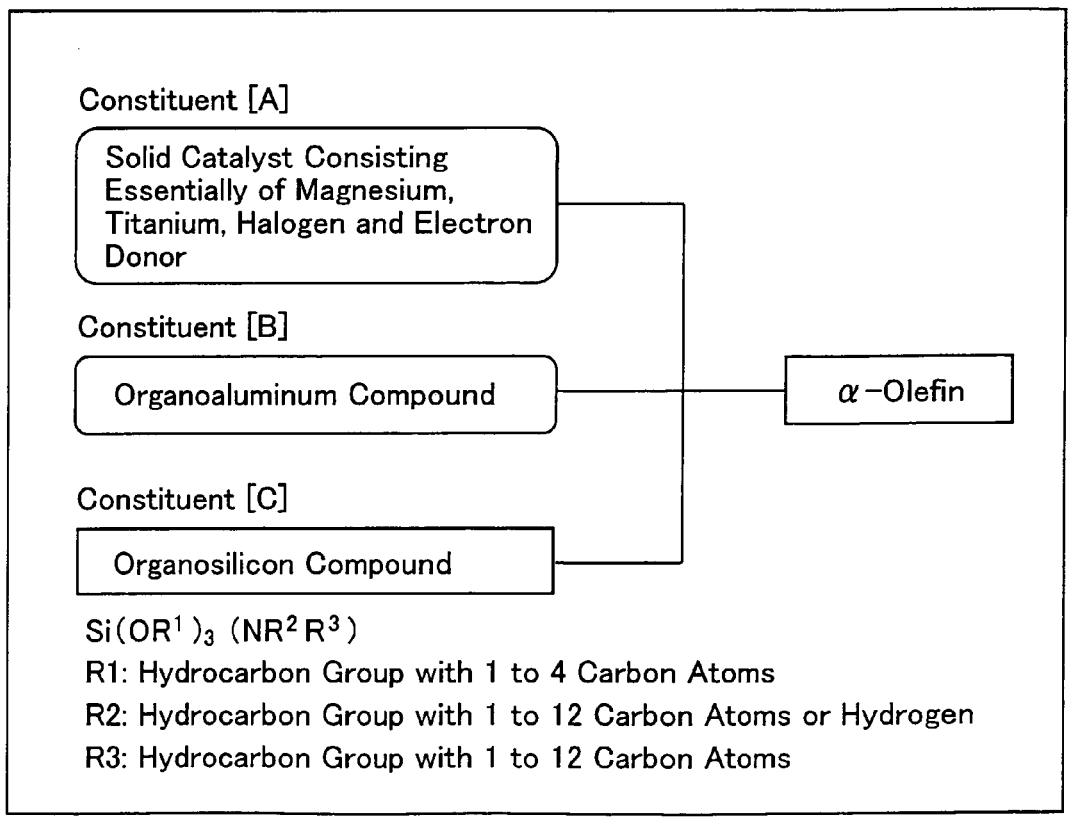
FIG. 5 is a flowchart of an adjustment method and polymerization method of a catalyst constituent for use in Experimental example 1.

A 2 L-inner volume autoclave composed of stainless steel and equipped with a magnet seal agitator is employed, of which inside is fully substituted for nitrogen. Supplied into the autoclave were: an n-heptane slurry as the solid catalyst constituent [A] by 5×10$^{-3}$ mmol on a titanium atom basis; a tri(ethyl)aluminum as the organoaluminum compound constituent [B] by 2.0 mmol; and the organosilicon compound constituents according to Examples 1-9 and the catalyst constituents according to Comparative examples 1-3 by 0.36 mmol. Then, hydrogen (0.4 MPa) and liquefied propylene (1.2 L) were introduced sequentially therein. After cooling the inside of the autoclave down to 10° C., agitating was initiated and prepolymerization was performed for 10 minutes. Subsequently, the temperature inside the autoclave was elevated up to 70° C., then polymerization was further performed at 70° C. for one hour under polymerization pressure of 3.8 MPa. After completion of polymerization, the non-reacted propylene gas was discharged, and the polymer was dried under reduced pressure at 60° C. for 20 hours to produce a white powdery polypropylene. A flowchart of an adjustment method and polymerization method of the catalyst constituents for use in Experimental example 1 is shown in FIG. 5, and experiment results are shown in Table 6.

TABLE 6

| | Polymerization Temperature (° C.) | Prepared Hydrogen Pressure (MPa) | Polymerization Reaction Rate (Kg/g-Cat. hr) | MFR (g/10 min) | Tm (° C.) | mmmm (%) |
|---|---|---|---|---|---|---|
| Example 1 | 70 | 0.4 | 43.9 | 444 | 162.7 | 98.9 |
| Example 2 | 70 | 0.4 | 32.9 | 1000 | 159.6 | 95.8 |
| Example 3 | 70 | 0.4 | 38.6 | 533 | 161.3 | 98.4 |
| Example 4 | 70 | 0.4 | 35.2 | 800 | 160.2 | 96.6 |
| Example 5 | 70 | 0.4 | 38.7 | 615 | 161.3 | 98.3 |
| Example 6 | 70 | 0.4 | 46.2 | 533 | 162.0 | 98.0 |
| Example 7 | 70 | 0.4 | 41.4 | 533 | 161.9 | 98.7 |
| Example 8 | 70 | 0.4 | 42.2 | 666 | 161.8 | 98.4 |
| Example 9 | 70 | 0.4 | 53.0 | 615 | 162.4 | 97.6 |
| Comparative example 1 | 70 | 0.4 | 37.8 | 120 | 162.3 | 98.1 |
| Comparative example 2 | 70 | 0.4 | 37.3 | 600 | 161.8 | 97.1 |
| Comparative example 3 | 70 | 0.4 | 42.6 | 76.5 | 162.2 | 98.0 |

It is found that when the catalyst constituent according to Comparative example 1 is employed, polymarization reaction rate, hydrogen response and stereoregularity are lower than when the organosilicon compound constituents according to Examples 1-9 are employed. It is found that when the catalyst constituent according to Comparative example 2 is employed, polymerization reaction rate and stereoregularity are lower than when the organosilicon compound constituents according to Examples 1-9 are employed. It is found that when the catalyst constituent according to Comparative example 3 is employed, hydrogen response and stereoregularity are lower than when the organosilicon compound constituents according to Examples 1-9 are employed.

EXPERIMENTAL EXAMPLE 2

Homopolymerization of Propylene

As Experimental example 2, homopolymerization of propylene was performed using a-olefin polymerization catalysts consisting of the solid catalyst constituent [A], the organoaluminum compound constituent [B], and the catalyst constituents [C] according to Examples 1-4. As Comparative experiments, homopolymerization of propylene was performed using α-olefin polymerization catalysts consisting of the solid catalyst constituent [A], the organoaluminum compound constituent [B], and the catalyst constituents [C] according to Comparative examples 1-3.

Experimental example 2 differs from 1 Experimental example in the following method to adjust the solid catalyst constituent [A]. Namely, 40 mL of n-decane, 7.1 g ($7.5 \times 10^{-2}$ mol) of anhydrous magnesium chloride, 35 ml ($2.2 \times 10^{-1}$ mol) of 2-ethylhexyl alcohol were added and mixed in a flask (volume of 0.2 L) equipped with a magnet seal agitator. Then, the temperature in the system is controlled at 130° C. and agitating was performed for two hours to form a uniform solution. 1.7 g ($1.2 \times 10^{-2}$ mol) of phthalic anhydride was added to the uniform solution, then a further reaction was performed for another one hour at 130° C. and thereafter the temperature was cooled down to room temperature. On the other hand, 200 ml (1.8 mmol) of tetrachloro titanium and a 0.71 g ($7.5 \times 10^{-3}$ mol) of anhydrous magnesium chloride were suspended and held at −20° C. in a flask (volume of 0.5 L) equipped with a magnet seal agitator and a G4 glass filter. The entire amount of the uniform solution was dropped into the flask, spending one hour. After dropping, the temperature in the system was elevated up to 110° C., then 5 mL ($1.8 \times 10^{-2}$ mol) of diiso-butyl orthophthalate was added, further agitating and reaction were performed for two hours. After reaction, thermal filtration was performed to extract a solid constituent. This solid constituent was resuspended in 300 mL of 2,4-dichloro toluene and a reaction was performed at 130° C. for one hour. After reaction, thermal filtration was performed to extract a solid constituent. The solid constituent was cleansed with n-decane and n-hexane until any titanium compound could not be detected in the cleansing solution. Then, the solid constituent was dried to obtain a powdery solid catalyst constituent [A]. The titanium content in the solid catalyst constituent was measured and found 1.1 wt. %. The content of di-iso-butylorthophthalate was found 10.8 wt. %. Polymerization of propylene was performed similarly in Experimental example 1. The result from Experimental example 2 is shown in Table 7.

TABLE 7

|  | Polymerization Temperature (° C.) | Prepared Hydrogen Pressure (MPa) | Polymerization Reaction Rate (Kg/g-Cat. hr) | MFR (g/10 min) | Tm (° C.) | mmmm (%) |
|---|---|---|---|---|---|---|
| Example 1 | 70 | 0.4 | 27.1 | 666 | 162.2 | 98.2 |
| Example 2 | 70 | 0.4 | 20.8 | 1800 | 158.9 | 94.9 |
| Example 3 | 70 | 0.4 | 23.1 | 330 | 161.5 | 97.2 |
| Example 4 | 70 | 0.4 | 21.6 | 1200 | 159.7 | 95.9 |
| Comparative example 1 | 70 | 0.4 | 22.5 | 180 | 162.1 | 97.5 |
| Comparative example 2 | 70 | 0.4 | 24.1 | 800 | 161.5 | 96.1 |
| Comparative example 3 | 70 | 0.4 | 21.6 | 199 | 161.8 | 97.0 |

It is found that when the catalyst constituent according to Comparative example 1 is employed, polymarization reaction rate, hydrogen response and stereoregularity are lower than when the organosilicon compound constituents according to Examples 1-4 are employed. It is found that when the catalyst constituent according to Comparative example 2 is employed, polymerization reaction rate and stereoregularity are lower than when the organosilicon compound constituents according to Examples 1-4 are employed. It is found that when the catalyst constituent according to Comparative example 3 is employed, hydrogen response and stereoregularity are lower than when the organosilicon compound constituents according to Examples 1-4 are employed.

EXPERIMENTAL EXAMPLE 3

Homopolymerization of Propylene

As Experimental example 3, homopolymerization of propylene was performed using α-olefin polymerization catalysts consisting of the solid catalyst constituent [A], the organoaluminum compound constituent [B], and the catalyst constituents [C] according to Examples 11-15. As Comparative experiments, homopolymerization of propylene was performed using α-olefin polymerization catalysts consisting of the solid catalyst constituent [A], the organoaluminum compound constituent [B], and the catalyst constituents [C] according to Comparative examples 3-5.

Solid catalyst constituent [A] that was adjusted in the following manner is employed in Experimental example 3. Namely, 400 mL of toluene and 80 g (0.7 mol) of diethoxy magnesium were added and suspended in a flask (volume of 1 L) equipped with a magnet seal agitator. Also, into another flask (volume of 1 L) equipped with a magnet seal agitator and a G4 glass filter, 200 mL of toluene and 154 ml (1.4 mol) of tetrachloro titanium were added and agitated to prepare mixed solution. The above suspension was added thereto, followed by a reaction at 5° C. for one hour. Then, 11.6 mL (0.04 mpl) of di n-butyl orthophthalate was introduced therein, followed by a reaction at 90° C. for two hours. After reaction, filtration and cleansing with a 500 mL of toluene were repeated 4 times. Then, 500 mL of toluene and 154 mL (1.4 mol) of tetrachloro titanium were added thereto, followed by agitating and reaction at 150° C. for two hours. After reaction, filtration and cleansing with 500 mL of n-heptane were repeated 5 times, followed by drying under reduced pressure to obtain a powdery solid catalyst constituent [A]. The titanium content in the solid catalyst constituent was measured and found 3.43 wt. %.

Figure 6:
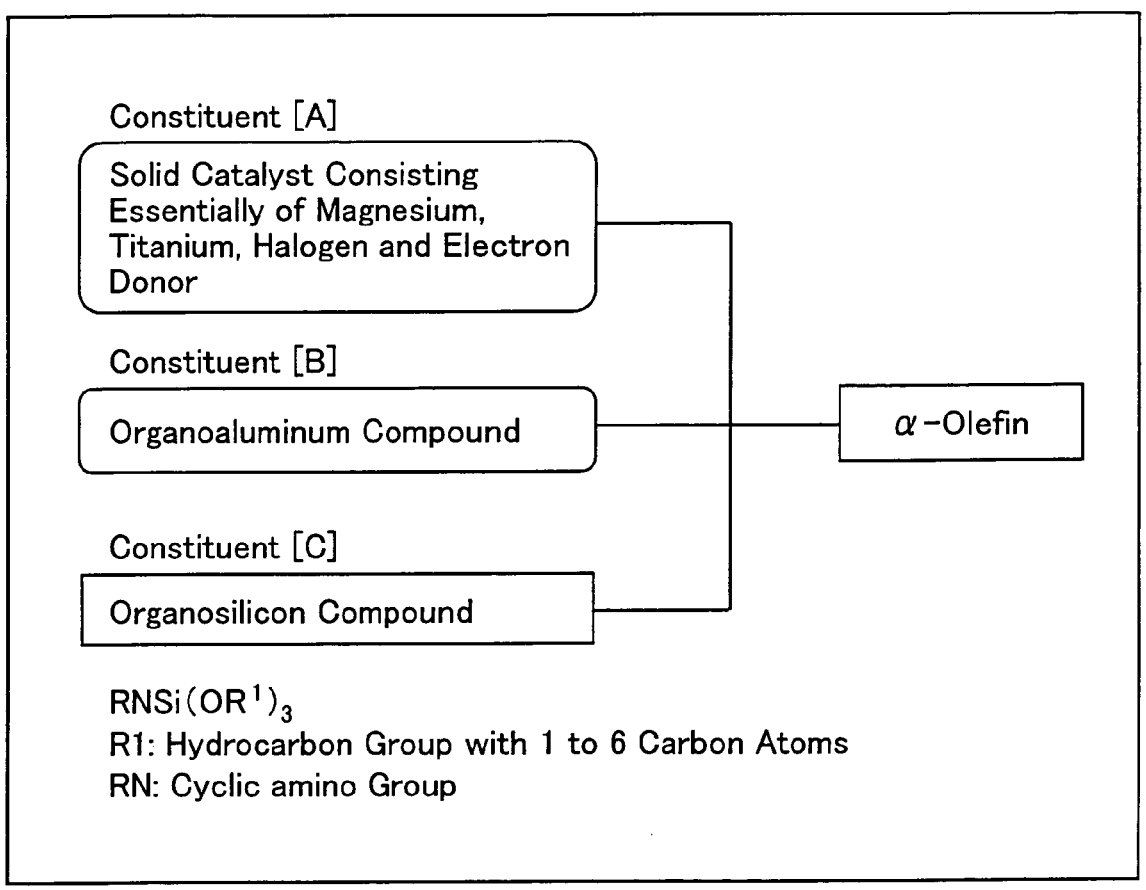
FIG. 6 is a flowchart of an adjustment method and polymerization method of a catalyst constituent for use in Experimental example 3.

Homopolymerization of propylene was performed in the following manner. A 2 L-inner volume autoclave composed of stainless steel and equipped with a magnet seal agitator is employed, of which inside is fully substituted for nitrogen. Supplied into the autoclave were: n-heptane slurry as the previously obtained solid catalyst constituent [A] by $5\times10^{-3}$ mmol on titanium atom basis; tri(ethyl)aluminum as the organoaluminum compound constituent [B] by 2.0 mmol; and the organosilicon compound constituents according to Example 11 to 17 or the catalyst constituents according to Comparative examples 3 to 5 by 0.36 mmol. Then, hydrogen (0.4 MPa) and liquefied propylene (1.2 L) were introduced sequentially therein. After cooling the inside of the autoclave down to 10° C., agitating was initiated and prepolymerization was performed for 10 minutes. Subsequently, the temperature inside the autoclave was elevated up to 70° C., then polymerization was further performed at 70° C. for one hour under polymerization pressure of 3.8 MPa. After completion of polymerization, the non-reacted propylene gas was discharged, and the polymer was dried under reduced pressure at 60° C. for 20 hours to produce white powdery polypropylene. A flowchart of an adjustment method and polymerization method of the catalyst constituents for use in Experimental example 3 is shown in FIG. 6, and experiment results are shown in Table 8.

TABLE 8

|  | Polymerization Temperature (° C.) | Prepared Hydrogen Pressure (MPa) | Polymerization Reaction Rate (Kg/g-Cat. hr) | MFR (g/10 min) | Tm (° C.) | mmmm (%) |
|---|---|---|---|---|---|---|
| Example 11 | 70 | 0.4 | 44.6 | 380 | 163.2 | 98.8 |
| Example 12 | 70 | 0.4 | 44.5 | 421 | 162.5 | 98.8 |
| Example 13 | 70 | 0.4 | 40.2 | 400 | 162.6 | 98.7 |
| Example 14 | 70 | 0.4 | 41.1 | 444 | 162.5 | 98.7 |

TABLE 8-continued

|  | Polymerization Temperature (° C.) | Prepared Hydrogen Pressure (MPa) | Polymerization Reaction Rate (Kg/g-Cat. hr) | MFR (g/10 min) | Tm (° C.) | mmmm (%) |
| --- | --- | --- | --- | --- | --- | --- |
| Example 15 | 70 | 0.4 | 32.0 | 1000 | 159.9 | 96.4 |
| Comparative example 3 | 70 | 0.4 | 42.6 | 76.5 | 162.2 | 98.0 |
| Comparative example 4 | 70 | 0.4 | 39.7 | 154 | 162.4 | 98.4 |
| Comparative example 5 | 70 | 0.4 | 40.2 | 121 | 162.4 | 98.5 |

It is found that when the catalyst constituent according to Comparative example 3 is employed, hydrogen response is particularly lower and stereoregularity is lower than when the organosilicon compound constituents according to Examples 11-15 are employed. It is found that when the catalyst constituent according to Comparative example 4 is employed, hydrogen response is particularly lower than when the organosilicon compound constituents according to Examples 11-15 are employed. It is found that when the catalyst constituent according to Comparative example 5 is employed, polymerization reaction rate is particularly lower and hydrogen response and stereoregularity are lower than when the organosilicon compound constituents according to Examples 11-15 are employed.

EXPERIMENTAL EXAMPLE 4

Homopolymerization of Propylene

As Experimental example 4, homopolymerization of propylene was performed using α-olefin polymerization catalysts consisting of the solid catalyst constituent [A], the organoaluminum compound constituent [B], the catalyst constituent [C] according to Example 1 and the organosilicon compound constituent [D]. In Experimental example 4, as the solid catalyst constituent [A], a THC-JC type was employed, which is commercially available from Toho Catalyst. A Ti content was 1.7 wt. %.

As the organosilicon compound constituent [D], a bis(perhydroisoquinolino)dimethoxysilane was employed. This bis(perhydroisoquinolino)dimethoxysilane was synthesized in the following manner. A stirrer piece was inserted into a 200 mL-volume, three-necked flask equipped with a dropping funnel. A vacuum pump was employed to substitute the inside of the flask sufficiently for nitrogen. Then, 100 mL of distilled and dehydrated n-heptane and 17.9 mL (0.12 mol) of decahydro isoquinoline were supplied into the flask. 75 mL (0.12 mol) of 1.6 M butyl lithium hexane solution was fed into the dropping funnel. While the temperature in the flask was maintained at 4° C., the butyl lithium solution in the dropping funnel was slowly dropped therefrom into the flask. After dropping, agitating was subsequently performed at room temperature for 12 hours to obtain a lithium salt of perhydro isoquinoline. A stirrer piece was inserted into a glass filter-added flask (volume of 400 mL) equipped with a dropping funnel. A vacuum pump was employed to substitute the inside of the flask sufficiently for nitrogen. Then, 60 mL of distilled and dehydrated n-heptane and 9 mL (0.06 mol) of tetramethoxysilane were supplied into the flask. The lithium salt of perhydroisoquinoline was fed into the dropping funnel. At room temperature, the lithium salt of perhydro isoquinoline in the dropping funnel was slowly dropped therefrom into the flask. After dropping, subsequently agitating was performed at 40° C. for 2 hours and at room temperature for 12 hours. After the generation of the target product was confirmed by gas chromatography, the precipitated product was filtered. The solvent in this filtrate was sufficiently settled and removed under reduced pressure, followed by primary distillation and secondary distillation of the product for purification to obtain the target product or the bis(perhydro isoquinolino)dimethoxy silane. This compound was found to have a boiling point of 180° C./1 mmHg and a GC purity of 98.5%.

Figure 7:
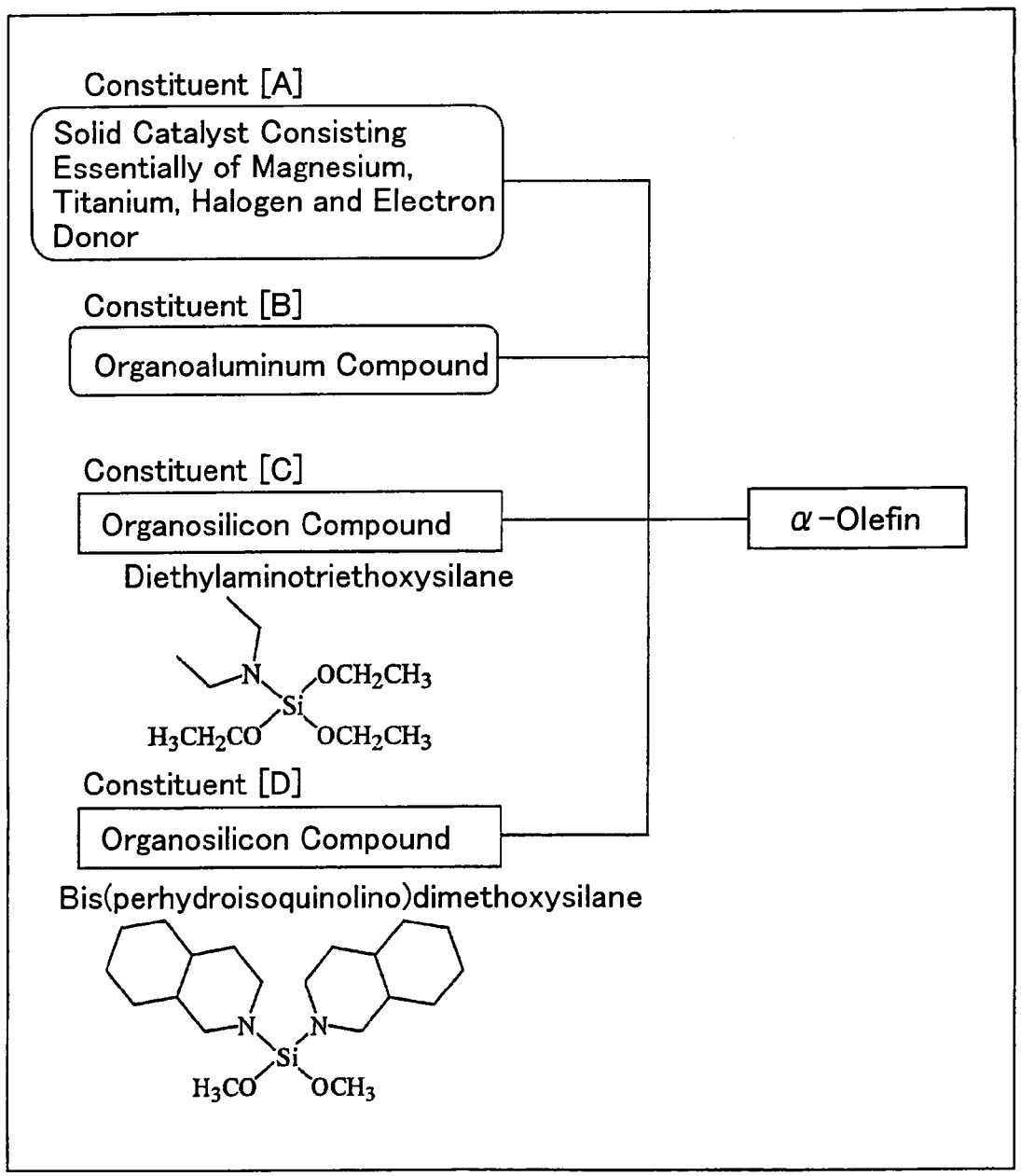
FIG. 7 is a flowchart of an adjustment method and polymerization method of a catalyst constituent for use in Experimental example 4.
Figure 8:
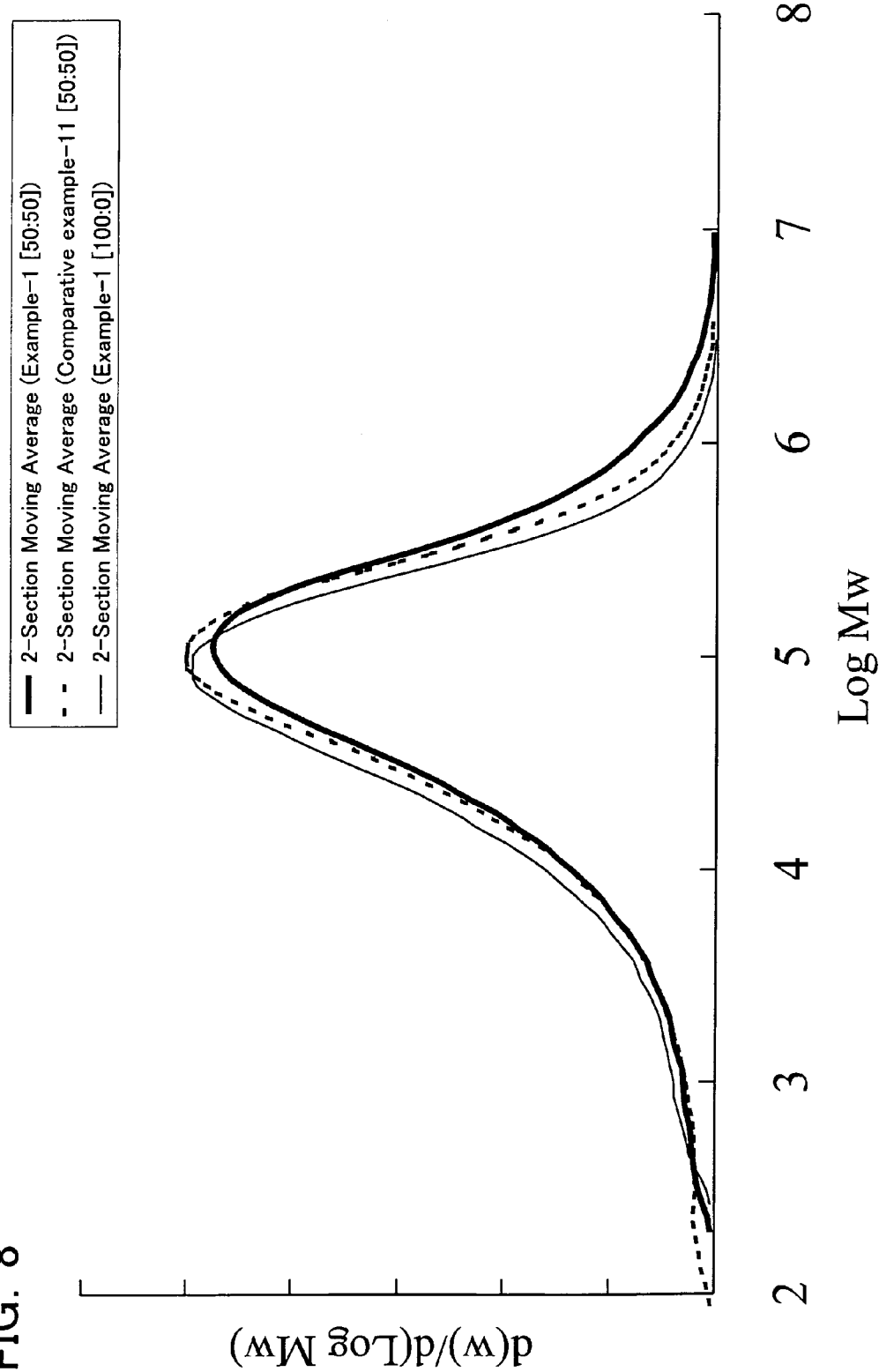
FIG. 8 is a graph showing GPC molecular weight distribution curves of Example 1 (50:50), Comparative example 11 (50:50) and Example 1 (100:0) in Experimental example 4.

Then, homopolymerization of propylene was performed in the following manner. A 2 L-inner volume autoclave composed of stainless steel and equipped with a magnet seal agitator is employed, of which inside is fully substituted for nitrogen. Supplied into the autoclave were: n-heptane slurry as the previously obtained solid catalyst constituent [A] by $2.5 \times 10^{-3}$ mmol on a titanium atom basis; tri(ethyl)aluminum as the organoaluminum compound constituent [B] by 2.0 mmol; and 0.18 mmol of the organosilicon compound constituent according to Example 1 as the constituent [C], and 0.18 mmol of bis(perhydro isoquinolino)dimethoxy silane as the constituent [D]. Then, hydrogen (0.4 MPa) and liquefied propylene (1.2 L) were introduced sequentially therein. After cooling the inside of the autoclave down to 10° C., agitating was initiated and prepolymerization was performed for 10 minutes. Subsequently, the temperature inside the autoclave was elevated up to 70° C., then polymerization was further performed at 70° C. for one hour under polymerization pressure of 3.8 MPa. After completion of polymerization, the non-reacted propylene gas was discharged, and the polymer was dried under reduced pressure at 60° C. for 20 hours to produce white powdery polypropylene. A flowchart of an adjustment method and polymerization method of the catalyst constituents for use in Experimental example 7 is shown in FIG. 7, and experiment results are shown in Table 8. FIG. 8 shows GPC molecular weight distribution curves.

Similar homopolymerization of propylene was performed to obtain the following products. In one product, 0.144 mmol of the constituent [C] and 0.216 mmol of the constituent [D] were employed (a molar ratio of the constituent [C] to the constituent [D] is 4:6). In another product, 0.108 mmol of the constituent [C] and 0.252 mmol of the constituent [D] were employed (a molar ratio of the constituent [C] to the constituent [D] is 3:7).

As Comparative experiments to the Experimental example 4, similar homopolymerization of propylene was performed to obtain the following products over the above experiments. In a product, 0.19 mmol of the catalyst constituent according to Comparative example 11 was employed as the constituent [C] instead of the organosilicon compound according to Example 1. In another product, the organosilicon compound according to Example 1 was employed as the constituent [C], and the constituent [D] was not employed. In yet another product, the organosilicon compound according to Comparative example 12 was employed as the constituent [C], and the constituent [D] was not employed. In another product, the organosilicon compound according to Comparative example 11 was employed as the constituent [C], and the constituent [D] was not employed. In yet another product, the constituent [C] was not employed, and the bis(perhydroisoquinolino)dimethoxy silane was employed as the constituent [D]. employed. As the organosilicon compound constituent [D], the bis(perhydroisoquinolino)dimethoxy silane was employed, which was similarly synthesized as Experimental example 4.

In Experimental example 5, a 2 L-inner volume autoclave composed of stainless steel and equipped with a magnet seal

TABLE 9

| Component C | Component C mol % | Component D mol % | $H_2$ MPa | Activity g-PP/g-Cat. hr | MFR g/10 min | H.I % | Tm °C. | Mw × $10^{-4}$ | Mw/Mn | mmmm % |
|---|---|---|---|---|---|---|---|---|---|---|
| Example 1 | 50 | 50 | 0.4 | 42,900 | 129 | 96.8 | 163.1 | 20.2 | 12.2 | 99.0 |
| Example 1 | 40 | 60 | 0.4 | 40,100 | 102 | 96.9 | 163.2 | 21.5 | 12.4 | 98.6 |
| Example 1 | 30 | 70 | 0.4 | 40,400 | 79.9 | 96.9 | 163.6 | 22.2 | 11.2 | 98.8 |
| Comparative example 11 | 50 | 50 | 0.4 | 43,400 | 216 | 95.9 | 161.8 | 15.2 | 10.3 | 97.8 |
| Example 1 | 100 | 0 | 0.4 | 43,900 | 444 | 96.6 | 162.7 | 12.4 | 7.1 | 98.9 |
| Comparative example 12 | 100 | 0 | 0.4 | 37,200 | 363 | 95 | 161.9 | 13.3 | 7.9 | 98.8 |
| Comparative example 11 | 100 | 0 | 0.4 | 47,400 | 307 | 95.4 | 161 | 14.1 | 7.6 | 97.4 |
| None | 0 | 100 | 0.4 | 37,100 | 33.4 | 96.8 | 163.9 | 32 | 17.3 | 98.6 |

As obvious from Table 9, the product using Example 1 as the organosilicon compound constituent [C], and the bis (perhydro isoquinolino)dimethoxy silane as the organosilicon compound constituent [D] has better hydrogen response and stereoregularity and a wider molecular weight distribution compared to other products using other constituents.

EXPERIMENTAL EXAMPLE 5

Bulk Homopolymerization of Propylene

As Experimental example 5, bulk homopolymerization of propylene was performed in the following manner using α-olefin polymerization catalysts consisting of the solid catalyst constituent [A], the organoaluminum compound constituent [B], and the catalyst constituent [C] according to Examples 1, 3-13 and 15-18; and an α-olefin polymerization catalyst consisting of the solid catalyst constituent [A], the organoaluminum compound constituent [B], the catalyst constituent [C] according to Example 1 and the organosilicon compound constituent [D]. In Experimental example 5, as the solid catalyst constituent [A], a THC-JC type was employed, which is commercially available from Toho Catalyst. Ti content was 1.7 wt. %. As the organoaluminum compound constituent [B], tri(ethyl)aluminum was employed. As the organosilicon compound constituent [D], the bis(perhydroisoquinolino)dimethoxy silane was employed, which was similarly synthesized as Experimental example 4.

In Experimental example 5, a 2 L-inner volume autoclave composed of stainless steel and equipped with a magnet seal agitator is employed, of which inside is fully substituted for nitrogen. Supplied into the autoclave were: n-heptane slurry of the previously obtained prepolymer by 2.5×$10^{-3}$ mmol on a titanium atom basis; triethyl aluminum as the organoaluminum compound constituent [B] by 2.0 mmol; and 0.36 mmol of diethylaminotriethoxy as the constituent [C]. Then, hydrogen (0.03 MPa, 0.12 MPa or 0.40 MPa) and liquefied propylene (1.2 L) were introduced sequentially therein. The temperature inside the autoclave was elevated up to and maintained at 70° C., and polymerization was performed for one hour. When hydrogen (0.40 MPa) was prepared, polymerization pressure was 3.8 MPa. After completion of polymerization, the non-reacted propylene gas was discharged, and the polymer was dried under reduced pressure at 60° C. for 20 hours to produce white powdery polypropylene.

As Comparative experiments to the Experimental example 5, similar homopolymerization of propylene was performed using α-olefin polymerization catalysts consisting of the solid catalyst constituent [A], the organoaluminum compound constituent [B], and the catalyst constituents [C] according to Comparative examples 3, 6-10. These results are shown in Tables 10-13.

TABLE 10

| | Hydrogen MPa | Polymerization Reaction Rate g-PP/g-Cat. hr | MFR g/10 min | H.I % | Tc °C. | Tm °C. | ΔH J/g |
|---|---|---|---|---|---|---|---|
| Example 1 | 0.03 | 29,600 | 9.5 | 98.7 | 115.4 | 165.3 | 110.0 |
| | 0.12 | 42,000 | 48.1 | 98.1 | 116.3 | 164.6 | 113.0 |
| | 0.40 | 43,900 | 444 | 96.6 | 116.6 | 162.7 | 117.0 |
| Example 3 | 0.03 | 31,900 | 11.9 | 98.7 | 114.1 | 164.1 | 107.0 |
| | 0.12 | 38,400 | 72.0 | 97.8 | 115.5 | 163.4 | 113.0 |
| | 0.40 | 38,600 | 533 | 95.9 | 115.6 | 161.3 | 117.0 |
| Example 4 | 0.03 | 28,900 | 13.8 | 98.5 | 114.0 | 164.3 | 106.0 |
| | 0.12 | 31,600 | 73.3 | 97.5 | 116.0 | 163.2 | 110.0 |
| | 0.40 | 31,800 | 533 | 95.8 | 117.1 | 161.6 | 117.0 |
| Example 5 | 0.03 | 28,100 | 13.0 | 98.7 | 114.5 | 164.6 | 108.0 |
| | 0.12 | 40,000 | 77.6 | 97.9 | 114.9 | 163.4 | 114.0 |
| | 0.40 | 38,700 | 615 | 95.8 | 115.5 | 161.3 | 116.0 |

TABLE 10-continued

|  | Hydrogen MPa | Polymerization Reaction Rate g-PP/g-Cat. hr | MFR g/10 min | H.I % | Tc °C. | Tm °C. | ΔH J/g |
|---|---|---|---|---|---|---|---|
| Example 6 | 0.03 | 34,400 | 14.6 | 98.4 | 114.8 | 164.6 | 105.0 |
|  | 0.12 | 45,400 | 89.8 | 97.2 | 116.4 | 163.6 | 110.0 |
|  | 0.40 | 46,200 | 533 | 95.4 | 116.5 | 162.0 | 114.0 |
| Example 7 | 0.03 | 32,800 | 11.7 | 98.4 | 114.4 | 164.9 | 108.0 |
|  | 0.12 | 40,400 | 63.4 | 97.9 | 114.4 | 163.8 | 112.0 |
|  | 0.40 | 41,400 | 533 | 95.9 | 115.3 | 161.9 | 119.0 |
| Example 8 | 0.03 | 32,900 | 10.2 | 98.5 | 113.7 | 164.9 | 106.0 |
|  | 0.12 | 40,000 | 68.9 | 97.5 | 114.5 | 163.8 | 112.0 |
|  | 0.40 | 42,200 | 666 | 95.2 | 115.8 | 161.8 | 118.0 |
| Example 9 | 0.03 | 27,200 | 25.0 | 98.0 | 115.8 | 164.1 | 103.0 |
|  | 0.12 | 50,800 | 116 | 97.1 | 115.6 | 163.5 | 108.0 |
|  | 0.40 | 53,000 | 615 | 95.7 | 117.1 | 162.4 | 114.0 |
| Example 10 | 0.03 | 24,400 | 7.0 | 98.2 | 115.5 | 165.2 | 106.0 |
|  | 0.12 | 35,200 | 29.9 | 97.4 | 115.8 | 163.7 | 110.0 |
|  | 0.40 | 39,600 | 190 | 95.7 | 119.5 | 162.8 | 115.0 |
| Example 11 | 0.03 | 38,300 | 8.5 | 98.6 | 118.8 | 165.4 | 106.0 |
|  | 0.12 | 38,900 | 43.2 | 98.1 | 116.3 | 164.3 | 109.0 |
|  | 0.40 | 44,600 | 266 | 96.9 | 119.7 | 163.2 | 115.0 |
| Example 12 | 0.03 | 34,400 | 11.2 | 98.7 | 116.1 | 165.3 | 107.0 |
|  | 0.12 | 45,200 | 61.9 | 97.7 | 118.2 | 164.7 | 112.0 |
|  | 0.40 | 44,500 | 421 | 96.6 | 117.9 | 162.2 | 118.0 |

TABLE 11

|  | Hydrogen MPa | Polymerization Reaction Rate g-PP/g-Cat. hr | MFR g/10 min | H.I % | Tc °C. | Tm °C. | ΔH J/g |
|---|---|---|---|---|---|---|---|
| Example 13 | 0.03 | 31,100 | 9.7 | 98.4 | 115.3 | 164.7 | 110.0 |
|  | 0.12 | 37,100 | 53.6 | 97.9 | 116.5 | 164.0 | 113.0 |
|  | 0.40 | 40,200 | 400 | 96.1 | 117.4 | 162.6 | 116.0 |
| Example 15 | 0.03 | 18,800 | 64.2 | 95.4 | 117.0 | 162.5 | 103.0 |
|  | 0.12 | 26,900 | 276 | 94.4 | 117.0 | 161.5 | 109.0 |
|  | 0.40 | 32,000 | — | 91.0 | 118.1 | 159.9 | 115.0 |
| Example 16 | 0.03 | 35,300 | 8.7 | 98.6 | 115.6 | 165.3 | 108.0 |
|  | 0.12 | 50,700 | 38.6 | 98.2 | 115.3 | 164.3 | 111.0 |
|  | 0.40 | 52,600 | 228 | 96.9 | 115.5 | 162.8 | 116.0 |
| Example 17 | 0.03 | 30,800 | 7.5 | 96.2 | 112.5 | 165.2 | 98.5 |
|  | 0.12 | 41,700 | 24.6 | 95.7 | 113.7 | 163.9 | 103.0 |
|  | 0.40 | 43,500 | 127 | 94.1 | 114.4 | 162.9 | 108.0 |
| Example 18 | 0.03 | 16,100 | 66.0 | 93.8 | 114.1 | 160.2 | 102.0 |
|  | 0.12 | 24,200 | 444 | 91.9 | 115.6 | 159.6 | 109.0 |
|  | 0.40 | 32,400 | — | 86.6 | 117.1 | 158.5 | 115.0 |
| Example 1 + D | 0.40 | 42,900 | 129 | 96.8 | 116.1 | 163.1 | 115.0 |
| Comparative example 3 | 0.12 | 43,200 | 14.5 | 98.0 | 113.6 | 163.7 | 110.0 |
|  | 0.40 | 42,600 | 76.5 | 97.0 | 117.0 | 162.9 | 114.0 |
| Comparative example 6 | 0.40 | 49,600 | 71.3 | 97.7 | 117.4 | 164.2 | 116.0 |
| Comparative example 7 | 0.40 | 58,600 | 23.2 | 98.2 | 116.0 | 165.0 | 111.0 |
| Comparative example 8 | 0.03 | 39,400 | 3.1 | 99.3 | 114.9 | 165.6 | 107.0 |
|  | 0.12 | 41,400 | 19.1 | 98.4 | 117.2 | 164.9 | 108.0 |
|  | 0.40 | 42,900 | 123 | 97.4 | 116.6 | 163.3 | 115.0 |
| Comparative example 9 | 0.40 | 37,100 | 33.4 | 96.8 | 116.1 | 163.9 | 113.0 |
| Comparative example 10 | 0.03 | 38,400 | 3.0 | 99.2 | 116.4 | 166.4 | 104.0 |
|  | 0.12 | 44,000 | 18.3 | 98.6 | 115.8 | 164.8 | 108.0 |
|  | 0.40 | 45,300 | 113 | 97.2 | 116.5 | 163.7 | 113.0 |

TABLE 12

|  | Hydrogen MPa | Mw × $10^{-4}$ | Mw/Mn | Mz/Mw | CXS % | mmmm % |
|---|---|---|---|---|---|---|
| Example 1 | 0.03 | 44.2 | 7.2 | 3.8 |  | 98.2 |
|  | 0.12 | 23.6 | 6.2 | 3.0 | 0.83 | 98.8 |
|  | 0.40 | 12.4 | 7.1 | 2.8 | 1.38 | 98.9 |
| Example 3 | 0.03 | 38.8 | 6.3 | 3.8 |  | 97.7 |
|  | 0.12 | 22.4 | 5.4 | 3.6 |  | 98.2 |
|  | 0.40 | 11.2 | 9.2 | 3.2 |  | 98.4 |

TABLE 12-continued

| | Hydrogen MPa | Mw × $10^{-4}$ | Mw/Mn | Mz/Mw | CXS % | mmmm % |
|---|---|---|---|---|---|---|
| Example 4 | 0.03 | 35.8 | 9.4 | 4.7 | | 97.0 |
| | 0.12 | 21.1 | 7.9 | 3.8 | | 97.4 |
| | 0.40 | 13.2 | 10.3 | 5.4 | | 98.1 |
| Example 5 | 0.03 | 36.0 | 4.5 | 3.5 | | 97.4 |
| | 0.12 | 21.9 | 5.8 | 3.3 | | 98.4 |
| | 0.40 | 12.4 | 6.5 | 3.3 | | 98.3 |
| Example 6 | 0.03 | 34.1 | 7.8 | 3.9 | | 97.1 |
| | 0.12 | 20.4 | 6.9 | 3.6 | | 97.4 |
| | 0.40 | 11.3 | 8.4 | 3.2 | | 98.0 |
| Example 7 | 0.03 | 42.3 | 7.2 | 4.2 | | 97.8 |
| | 0.12 | 24.2 | 6.0 | 3.3 | | 98.2 |
| | 0.40 | 12.1 | 6.5 | 2.8 | | 98.7 |
| Example 8 | 0.03 | 45.0 | 8.5 | 4.9 | | 97.9 |
| | 0.12 | 25.4 | 8.4 | 5.5 | | 98.4 |
| | 0.40 | 12.0 | 7.9 | 3.0 | | 98.4 |
| Example 9 | 0.03 | 29.4 | 7.3 | 3.9 | | 96.4 |
| | 0.12 | 18.0 | 7.2 | 3.2 | | 97.2 |
| | 0.40 | 11.2 | 7.8 | 3.1 | | 97.6 |
| Example 10 | 0.03 | 48.1 | 11.8 | 4.5 | | 96.4 |
| | 0.12 | 29.4 | 12.1 | 4.8 | | 97.5 |
| | 0.40 | 17.2 | 11.3 | 4.4 | | 98.3 |
| Example 11 | 0.03 | 41.5 | 6.2 | 3.4 | | 98.2 |
| | 0.12 | 24.4 | 6.7 | 3.0 | 0.94 | 98.6 |
| | 0.40 | 14.8 | 6.7 | 2.9 | 1.46 | 98.8 |
| Example 12 | 0.03 | 41.5 | 6.4 | 3.4 | | 98.1 |
| | 0.12 | 23.5 | 6.1 | 3.0 | | 98.4 |
| | 0.40 | 13.4 | 6.3 | 3.5 | 1.42 | 98.8 |

TABLE 13

| | Hydrogen MPa | Mw × $10^{-4}$ | Mw/Mn | Mz/Mw | CXS % | mmmm % |
|---|---|---|---|---|---|---|
| Example 13 | 0.03 | 41.6 | 7.2 | 3.8 | | 97.9 |
| | 0.12 | 24.0 | 7.4 | 3.5 | | 98.2 |
| | 0.40 | 13.1 | 6.7 | 3.1 | 1.68 | 98.6 |
| Example 15 | 0.03 | 25.6 | 7.6 | 4.3 | | 95.0 |
| | 0.12 | 15.9 | 6.6 | 3.7 | | 96.2 |
| | 0.40 | 10.0 | 6.9 | 4.2 | | 96.9 |
| Example 16 | 0.03 | 40.6 | 8.4 | 3.5 | | 97.8 |
| | 0.12 | 26.0 | 6.4 | 3.1 | | 98.7 |
| | 0.40 | 15.1 | 5.8 | 2.6 | | 98.9 |
| Example 17 | 0.03 | 47.8 | 11.5 | 5.0 | | 94.9 |
| | 0.12 | 32.0 | 11.3 | 4.4 | | 96.2 |
| | 0.40 | 19.4 | 13.6 | 4.8 | | 96.7 |
| Example 18 | 0.03 | 23.1 | 7.8 | 4.6 | 5.56 | 93.4 |
| | 0.12 | 13.0 | 6.9 | 3.7 | 4.54 | 95.1 |
| | 0.40 | 7.5 | 6.8 | 2.9 | | 96.4 |
| Example 1 + D | 0.40 | 20.2 | 12.2 | 5.0 | | 99.0 |
| Comparative example 3 | 0.12 | 30.4 | 7.3 | 3.3 | | 97.7 |
| | 0.40 | 22.4 | 14.4 | 4.1 | | 98.2 |
| Comparative example 6 | 0.40 | 22.5 | 9.7 | 3.8 | | 99.0 |
| Comparative example 7 | 0.40 | 31.4 | 9.3 | 3.5 | | 98.8 |
| Comparative example 8 | 0.03 | 61.4 | 7.3 | 3.7 | | 98.5 |
| | 0.12 | 33.2 | 6.3 | 3.5 | 0.67 | 98.7 |
| | 0.40 | 19.4 | 9.1 | 4.1 | 1.12 | 98.7 |
| Comparative example 9 | 0.40 | 32.0 | 17.3 | 5.5 | | 98.6 |
| Comparative example 10 | 0.03 | 54.8 | 4.9 | 3.2 | | 98.7 |
| | 0.12 | 31.8 | 7.6 | 3.3 | 0.58 | 98.6 |
| | 0.40 | 20.6 | 9.2 | 3.9 | 1.04 | 98.9 |

It is found that when the catalyst constituents according to Comparative examples 3, 6-10 are employed, hydrogen response is particularly lower and stereoregularity are lower than when the organosilicon compound constituents according to Examples 1, 3-13 and 15-18 are employed.

In Experimental example 5, the polypropylene polymerized using the organosilicon compounds according to Examples 1, 7 and 13 as the constituent [C] exhibits physical property values such as MFR=300 g/10 min and mmmm=98.5% or more at hydrogen (0.40 MPa).

EXPERIMENTAL EXAMPLE 6

(Relation Between Prepared Hydrogen Amount and MFR)

Figure 9:
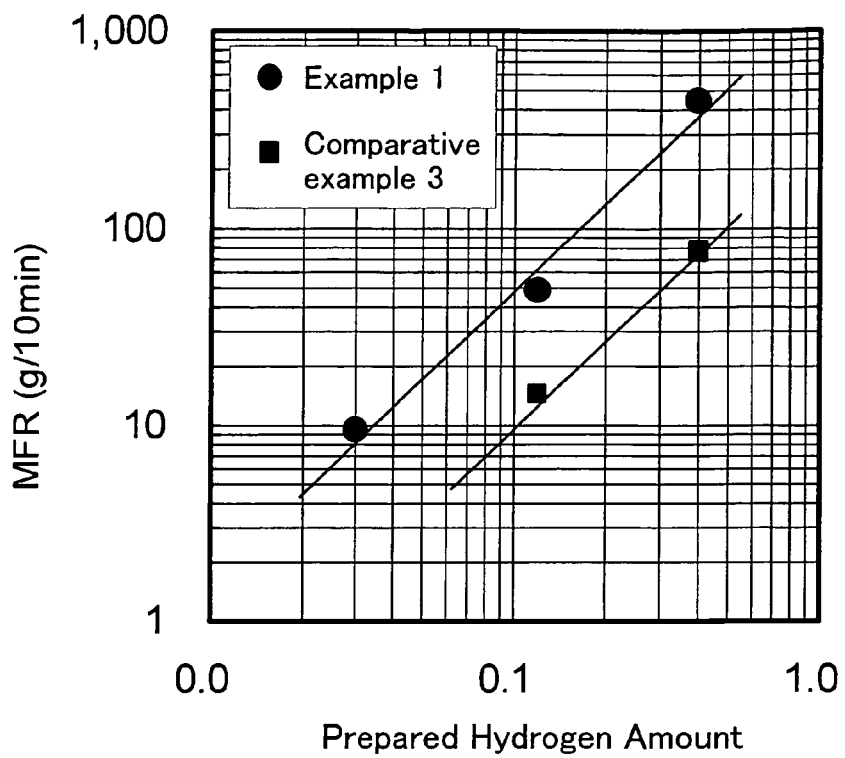
FIG. 9 is a graph showing relations between a prepared amount of hydrogen (MPa) and a MFR.

Polymerization of propylene was performed like Experimental example 5 using the organosilicon compound according to Example 1 as the constituent [C] and varying a prepared hydrogen amount (MPa) from 0.03 through 0.12 to 0.40. As Comparative experiments, polymerization of propylene was performed like Experimental example 4 using the catalyst constituent according to Comparative example 3 as the constituent [C] and varying a prepared hydrogen amount (MPa) from 0.12 to 0.40. These results are shown in FIG. 9. As can be seen from FIG. 9, when the organosilicon compound according to Example 1 is employed, hydrogen response is more excellent, because of achievement of a high MFR with a less prepared hydrogen amount, than when the catalyst constituent according to Comparative example 3 is employed.

EXPERIMENTAL EXAMPLE 7

(Relation Between Hydrogen Response and Stereoregularity)

Figure 10:
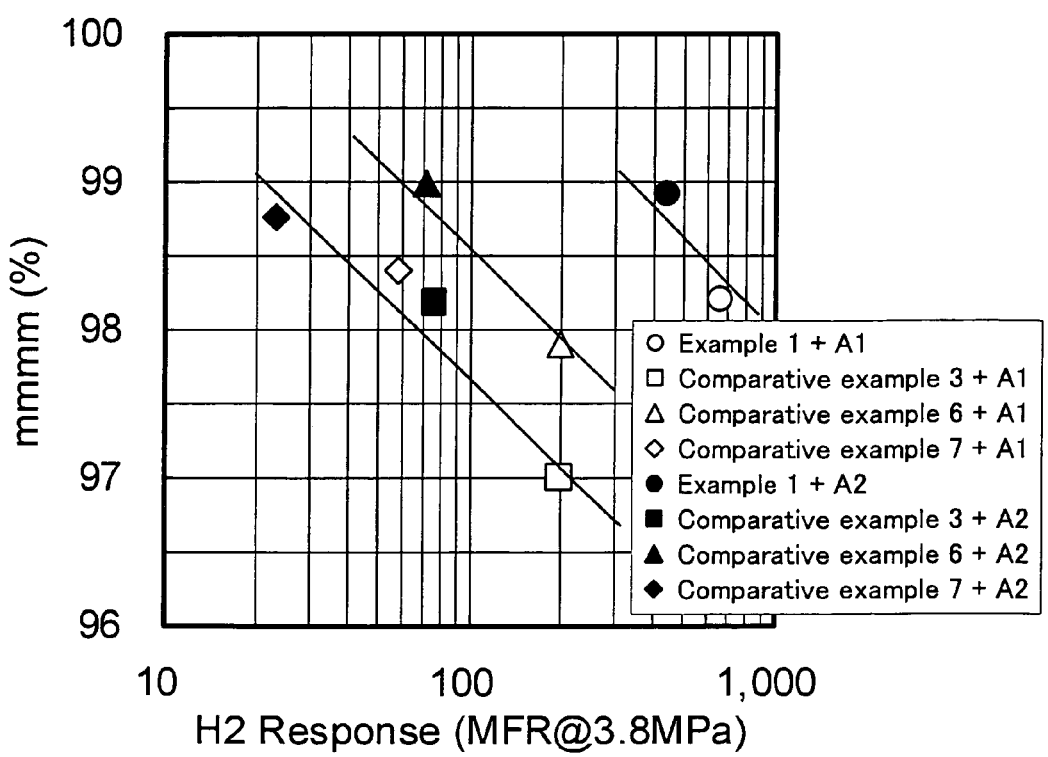
FIG. 10 is a graph showing relations between hydrogen response and stereoregularity.

Polymerization of propylene was performed like Experimental example 4 using as the constituent [C] the organosilicon compound according to Example 1, and using as the solid catalyst constituent [A] a THC-JC type commercially available from Toho Catalyst (constituent [$A_1$]) or the product synthesized in Experimental example 2 (constituent [$A_2$]). As Comparative experiments, polymerization of propylene was performed using the catalyst constituents according to Comparative examples 3, 6 and 7 as the constituent [C]. These results are shown in FIG. 10. As can be seen from FIG. 10, when the organosilicon compound according to Example 1 is employed, hydrogen response is higher and stereoregularity is more excellent, regardless of types of the solid catalyst constituents, than when the catalyst constituent according to Comparative example 3 is employed.

EXPERIMENTAL EXAMPLE 8

Homopolymerization of Propylene

As Experimental example 8, prepolymerization of propylene was performed using an α-olefin polymerization catalyst consisting of the solid catalyst constituent [A], the organoaluminum compound constituent [B], and the organosilicon compound constituent [D]. Then, main polymerization of propylene was performed using an α-olefin polymerization catalyst consisting of the solid catalyst constituent [A], the organoaluminum compound constituent [B], and the catalyst constituent [C] according to Example 1. In Experimental example 8, as the solid catalyst constituent [A], a THC-JC type was employed, which is commercially available from Toho Catalyst. Ti content was 1.7 wt. %. As the organoaluminum compound constituent [B], tri(ethyl) aluminum was employed. As the organosilicon compound constituent [D], bis(perhydroisoquinolino)dimethoxysilane synthesized like Experimental example 4 was employed.

For prepolymerization, a 200 ml-inner volume flask equipped with a magnet seal agitator is employed, of which inside is fully substituted for nitrogen. Sequentially injected into the flask were: 100 ml of distilled and dehydrated n-heptane; 1.1 mmol of triethylaluminum as the constituent [B]; and 0.18 mmol of bisperhydroisoquinolinodimethoxysilane as the constituent [D]. Thereafter, the constituent [A] was added by 0.37 mmol on a Ti atom basis (a molar ratio of Constituent [A]/Constituent [B]/Constituent [α]=1/3/0.5) followed by aging at 25° C. for 10 minutes. Then, prepolymerization was performed for 5 minutes under normal pressure, feeding a propylene gas into the flask continuously at a flow rate of 165 ml/min. The resultant prepolymer has a weight ratio of PP/Constituent [A]=1.89.

This prepolymer was employed for the following main polymerization of propylene. Namely, a 2 L-inner volume autoclave composed of stainless steel and equipped with a magnet seal agitator is employed, of which inside is fully substituted for nitrogen. Supplied into the autoclave were: n-heptane slurry of the resultant prepolymer by $2.5 \times 10^{-3}$ mmol on a titanium atom basis; triethylaluminum as the constituent [B] by 2.2 mmol; and the organosilicon compound according to Example 1 as the constituent [C] by 0.18 mmol. Then, hydrogen (0.4 MPa) and liquefied propylene (1.2 L) were introduced therein. The temperature inside the autoclave was elevated up to and held at 70° C., then polymerization was performed for one hour. After completion of polymerization, the non-reacted propylene gas was discharged, and the polymer was dried under reduced pressure at 60° C. for 20 hours to produce a white powdery polypropylene.

Figure 11:
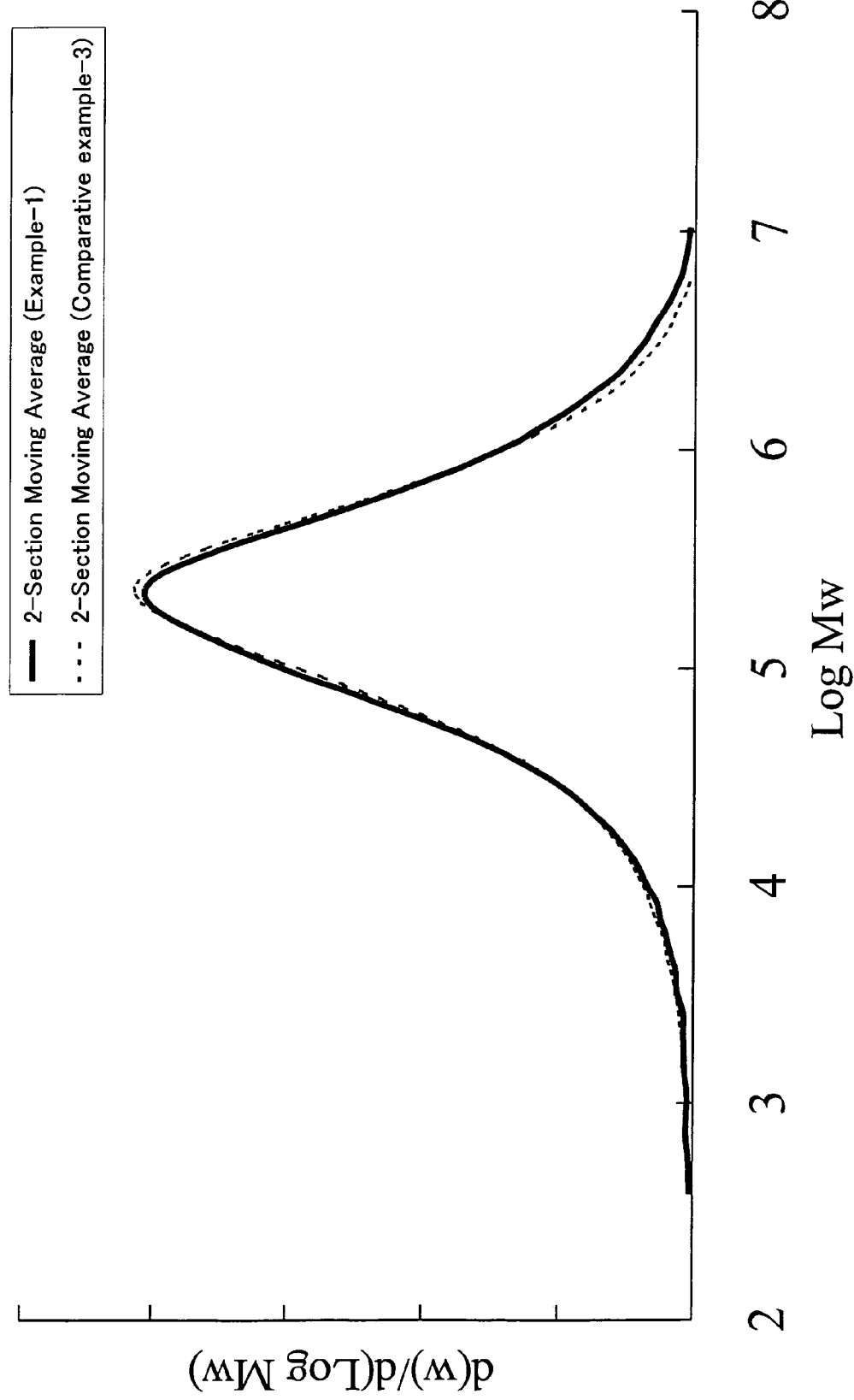
FIG. 11 is a graph showing GPC molecular weight distribution curves of Example 1 and Comparative example 3 in Experimental example 8.

As Comparative experiments to Experimental example 8, polymerization of propylene was performed using the solid catalyst constituent [A], the organoaluminum compound constituent [B], and the catalyst constituent according to Comparative example 3. These experiment results are shown in Tables 14 and 15, and GPC molecular weight distribution curves are shown in FIG. 11.

TABLE 14

| | $H_2$ MPa | Activity g-PP/g-Cat. hr | MFR g/10 min | H.I % | Tc °C. | Tm °C. |
|---|---|---|---|---|---|---|
| Example 1 | 0.07 | 33,700 | 12.5 | 98.6 | 113.9 | 165.0 |
| Comparative example 3 | 0.12 | 43,000 | 13.9 | 98.1 | 114.9 | 163.8 |

TABLE 15

| | ΔH J/g | Mw × $10^{-4}$ | Mw/Mn | Mz/Mw | mmmm % |
|---|---|---|---|---|---|
| Example 1 | 110.0 | 42.0 | 7.2 | 4.1 | 98.0 |
| Comparative example 3 | 109.0 | 36.8 | 5.9 | 3.1 | 97.4 |

The polypropylene polymerized in Experimental example 8 has high stereoregularity, high melt fluidity and wide molecular weight distributions, the α-olefin polymer has good moldability and excellent property against appearance deficits of moldings such as flow marks. Particularly, Example 1 employs the expensive bis(perhydroisoquinolino)dimethoxysilane only for prepolymerization and thus can reduce the cost of polymerization of propylene.

EXPERIMENTAL EXAMPLE 9

(Block Copolymerization of Ethylene-propylene)

As Experimental example 7, block copolymerization of ethylene/propylene was performed using an α-olefin polymerization catalyst consisting of the solid catalyst constituent [A], the organoaluminum compound constituent [B], and the catalyst constituent [C] according to Example 1; and an α-olefin polymerization catalyst consisting of the solid catalyst constituent [A], the organoaluminum compound constituent [B], the catalyst constituent [C] according to Example 1, and the organosilicon compound constituent [D]. In Experimental example 7, as the solid catalyst constituent [A], a THC-JC type was employed, which is commercially available from Toho Catalyst. Ti content was 1.7 wt. %. As the organosilicon compound constituent [D], bis(perhydroisoquinolino)dimethoxysilane synthesized like Experimental example 5 was employed.

<First Step: Propylene Bulk Homopolymerization>

A 2 L-inner volume autoclave composed of stainless steel and equipped with a magnet seal agitator is employed, of which inside is fully substituted for nitrogen. Supplied into the autoclave were: n-heptane slurry of the previously obtained solid catalyst constituent [A] by $2.5 \times 10^{-3}$ mmol on a titanium atom basis; tri(ethyl)aluminum as the organoaluminum compound constituent [B] by 1.5 mmol; and the organosilicon compound constituent according to Example 1 by 0.25 mmol. Then, hydrogen (0.4 MPa) and liquefied propylene (1.2 L) were introduced sequentially therein. After cooling the inside of the autoclave down to 10° C., agitating was initiated and prepolymerization was performed for 10 minutes. Subsequently, the temperature inside the autoclave was elevated up to 70° C., then polymerization was performed at 70° C. for one hour under polymerization pressure of 3.8 MPa. After completion of polymerization, the non-reacted propylene gas was discharged, and the inside was substituted sufficiently for nitrogen. Then, pressure in the autoclave was held at 0.02 MPa in gauge pressure. Thereafter, the weight was measured, and the yield of polypropylene was calculated from the weight of the empty autoclave and found 288 g. After measurement of the yield, 76 g of polypropylene was extracted from inside the autoclave in nitrogen ambient. Then, the extracted polymer was dried under reduced pressure at 60° C. for 20 hours to produce white powdery polypropylene.

<Second Step: Gas-phase Ethylene/Propylene Copolymerization>

Figure 12:
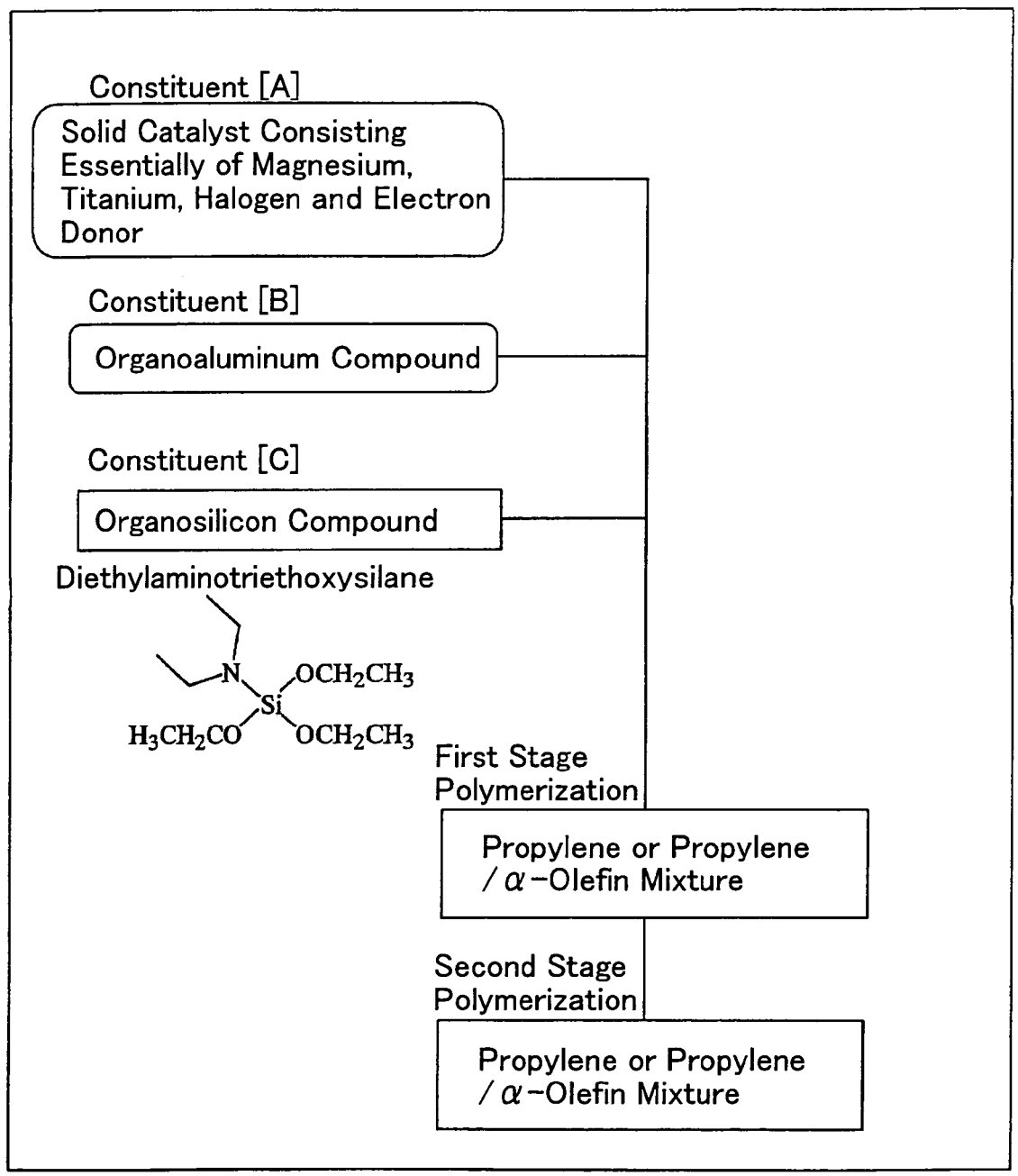
FIG. 12 is a flowchart of an adjustment method and polymerization method of a catalyst constituent for use in Experimental example 9.

After completion of bulk polymerization, in which the pressure in the system was held at 0.02 MPa in gauge pressure, the temperature in the autoclave was set at 70° C. Mixed gas of ethylene and propylene was continuously supplied to the autoclave at a proportion of 0.7:1 in volume ratio (700 Ncc/min and 1000 Ncc/min, respectively) to adjust the copolymerization pressure at 1.2 MPa in gauge pressure. For copolymerization reactions at the same temperature under the same pressure, the non-reacted gas was discharged outside the system so as to hold the copolymerization pressure at 1.2 MPa in gauge pressure, followed by copolymerization reaction at 70° C. for 3 hours. During the copolymerization reaction (after 0.5 hour, one hour and two hours), each 20 g of the polymer was extracted from inside the autoclave. The extracted copolymer was dried under reduced pressure at 60° C. for 20 hours to produce white powdery block copolymer. A proportion of the copolymer part in the total polymer (block ratio) was calculated and found 7.83 wt. % after 0.5 hour; 12.34 wt. % after one hour; 17.54 wt. % after 2 hours; and 20.65 wt. % after 3 hours. A flowchart of an adjustment method and polymerization method of the catalyst constituents for use in Experimental example 9 is shown in FIG. 12. Polymerization results and characteristics of the resultant copolymers are shown in Tables 16-18.

Similarly, propylene block copolymer was produced except for addition of a diethylamino triethoxy silane as the constituent [C] by 0.125 mmol and a bis(perhydro isoquinolino) dimethoxy silane as the constituent [D] by 0.125 mmol, as the catalyst constituent. Polymerization results and characteristics of the resultant copolymer are shown in Tables 16-18.

As Comparative experiments to Experimental example 7, ethylene-propylene block copolymers were similarly produced except for use of the catalyst constituents according to Comparative examples 3, 6, 8, 9 and 13 as the constituent [C] instead of the organosilicon compound according to Example 1. Polymerization results and characteristics of the resultant copolymer are shown in Tables 16-18.

TABLE 16

|  | Homo-PP | | | |
| --- | --- | --- | --- | --- |
|  | Homo Yield g-HP/g-Cat. hr | MFR g/10 min | CXS wt % | mmmm %(UBE) |
| Example 1 | 41,100 | 400 | 1 | 99.1 |
| Example 1 + D | 41,600 | 101 | 1.2 | 98.8 |
| Comparative example 3 | 42,300 | 60.1 | 1 | 98.2 |
| Comparative example 6 | 49,100 | 71.3 | 0.6 | 98.9 |
| Comparative example 8 | 38,900 | 113 | 0.9 | 98.6 |
| Comparative example 9 | 37,300 | 34.9 | 1.1 | 98.8 |
| Comparative example 13 | 59,900 | 25.5 | 0.6 | 99 |

TABLE 17

|  | Copolymerization Time Hr | Yield from Copolymerization g-CP/g-Cat | MFR g/10 min | Block Ratio wt % |
| --- | --- | --- | --- | --- |
| Example 1 | 0.5 | 3,500 | 111 | 7.8 |
|  | 1 | 5,800 | 66.3 | 12.3 |
|  | 2 | 8,800 | 39 | 17.5 |
|  | 3 | 10,700 | 34.9 | 20.7 |
| Example 1 + D | 0.5 | 3,900 | 29.3 | 8.5 |
|  | 1 | 6,400 | 18.1 | 13.3 |
|  | 2 | 9,400 | 10.2 | 18.4 |
|  | 3 | 11,300 | 8.9 | 21.4 |
| Comparative example 3 | 0.5 | 5,400 | 26.5 | 11.3 |
|  | 1 | 9,100 | 14 | 17.7 |
|  | 2 | 13,600 | 8.9 | 24.3 |
|  | 3 | 16,400 | 7.5 | 27.9 |
| Comparative example 6 | 0.5 | 7,500 | 15.8 | 13.3 |
|  | 1 | 12,900 | 7.4 | 20.8 |
|  | 2 | 19,300 | 4.9 | 28.2 |
|  | 3 | 23,400 | 4.2 | 32.2 |
| Comparative example 8 | 0.5 | 4,000 | 45.2 | 9.3 |
|  | 1 | 6,600 | 26.2 | 14.6 |
|  | 2 | 10,100 | 15.4 | 20.7 |
|  | 3 | 12,400 | 12.4 | 24.1 |
| Comparative example 9 | 0.5 | 3,100 | 15.4 | 7.7 |
|  | 1 | 5,300 | 9.2 | 12.5 |
|  | 2 | 8,500 | 4.9 | 18.5 |
|  | 3 | 11,000 | 3.9 | 22.8 |
| Comparative example 13 | 0.5 | 10,500 | 6 | 15 |
|  | 1 | 17,100 | 3.2 | 22.2 |
|  | 2 | 25,400 | 2 | 29.8 |
|  | 3 | 30,500 | 1.3 | 33.7 |

TABLE 18

|  | p-xylene Soluble Component | | | p-xylene Insoluble | |
| --- | --- | --- | --- | --- | --- |
|  | Weight wt % | Ethylene Content wt % | [η] dl/g | Component Ethylene Content wt % | Rubber Transfer Rate |
| Example 1 | 6.4 | 39.6 | 11 | 1.4 | 0.81 |
|  | 9.6 | 39.5 | 11.6 | 2.3 | 0.78 |
|  | 13.8 | 40 | 12 | 2.7 | 0.79 |
|  | 15.9 | 40.4 | 12.3 | 3.7 | 0.77 |
| Example 1 + D | 6.6 | 37.9 | 10.8 | 1.8 | 0.77 |
|  | 9.7 | 37.8 | 11.2 | 3 | 0.73 |
|  | 14.5 | 38.2 | 11.8 | 4.1 | 0.79 |
|  | 15.7 | 38.6 | 12.1 | 5.1 | 0.73 |
| Comparative example 3 | 8.8 | 31.4 | 6.3 | 2.1 | 0.77 |
|  | 13.6 | 30.9 | 6.6 | 3.5 | 0.77 |
|  | 19 | 31.2 | 7 | 4.9 | 0.78 |
|  | 21.2 | 32 | 7 | 5.2 | 0.76 |
| Comparative example 6 | 10.7 | 32.5 | 10.1 | 2 | 0.8 |
|  | 16 | 31.8 | 11.3 | 3.4 | 0.77 |
|  | 21.8 | 32.5 | 11.9 | 4.4 | 0.77 |
|  | 24.4 | 32.4 | 12.3 | 4.8 | 0.76 |
| Comparative example 8 | 6.8 | 34.5 | 7.3 | 2.2 | 0.73 |
|  | 11.5 | 33.6 | 7.5 | 3.4 | 0.79 |
|  | 16 | 34.5 | 7.8 | 4.3 | 0.77 |
|  | 18.9 | 34.3 | 8 | 5.7 | 0.78 |
| Comparative example 9 | 5.6 | 33.3 | 8.6 | 1.8 | 0.73 |
|  | 9.3 | 33.6 | 9.4 | 3 | 0.75 |
|  | 13.9 | 34.4 | 10.1 | 3.9 | 0.75 |
|  | 16.7 | 34.6 | 10.1 | 5.5 | 0.73 |
| Comparative example 13 | 12.6 | 31 | 10.8 | 1.8 | 0.84 |
|  | 18.5 | 31.8 | 11.1 | 2.9 | 0.83 |
|  | 25 | 31 | 10.9 | 4.4 | 0.84 |
|  | 28.6 | 31 | 11 | 4.6 | 0.85 |

It is found that when the catalyst constituents of Comparative examples 3, 6, 8, 9 and 13 are employed, the block copolymers have lower MFR and worse melt fluidity than when the organosilicon compound according to Example 1 is employed solely or in addition to the constituent [D]. It is further found that as the ethylene content is low in the rubber constituent, the ethylene reactivity is inferior.

It is found that when the catalyst constituent of Comparative examples 6 is employed, the block copolymer has lower MFR and worse melt fluidity than when the organosilicon compound according to Example 1 is employed solely or in addition to the constituent [D]. It is further found that as the ethylene content is low in the rubber constituent, the ethylene reactivity is inferior.

It is found from the above results that, the use of the diethylaminotriethoxysilane as the constituent [C] in the ethylene-propylene block copolymer can achieve the most excellent performance on balanced stereoregularity, hydrogen response, melt fluidity of block copolymers, and reactivity of ethylene.

EXPERIMENTAL EXAMPLE 10

(Random Copolymerization of Ethylene-propylene)

As Experimental example 10, random copolymerization of ethylene/propylene was performed using an α-olefin polymerization catalyst consisting of the solid catalyst constituent [A], the organoaluminum compound constituent [B], and the catalyst constituent [C] according to Example 1. In Experimental example 10, as the solid catalyst constituent [A], a THC-JC type was employed, which is commercially available from Toho Catalyst. Ti content was 1.7 wt. %. As the organoaluminum compound constituent [B], tri(ethyl) aluminum was employed. As Comparative example to Experimental example 10, random copolymerization of ethylene/propylene was performed using an α-olefin polymerization catalyst consisting of the solid catalyst constituent [A], the organoaluminum compound constituent [B], and the catalyst constituent [C] according to Comparative example 3.

Figure 13:
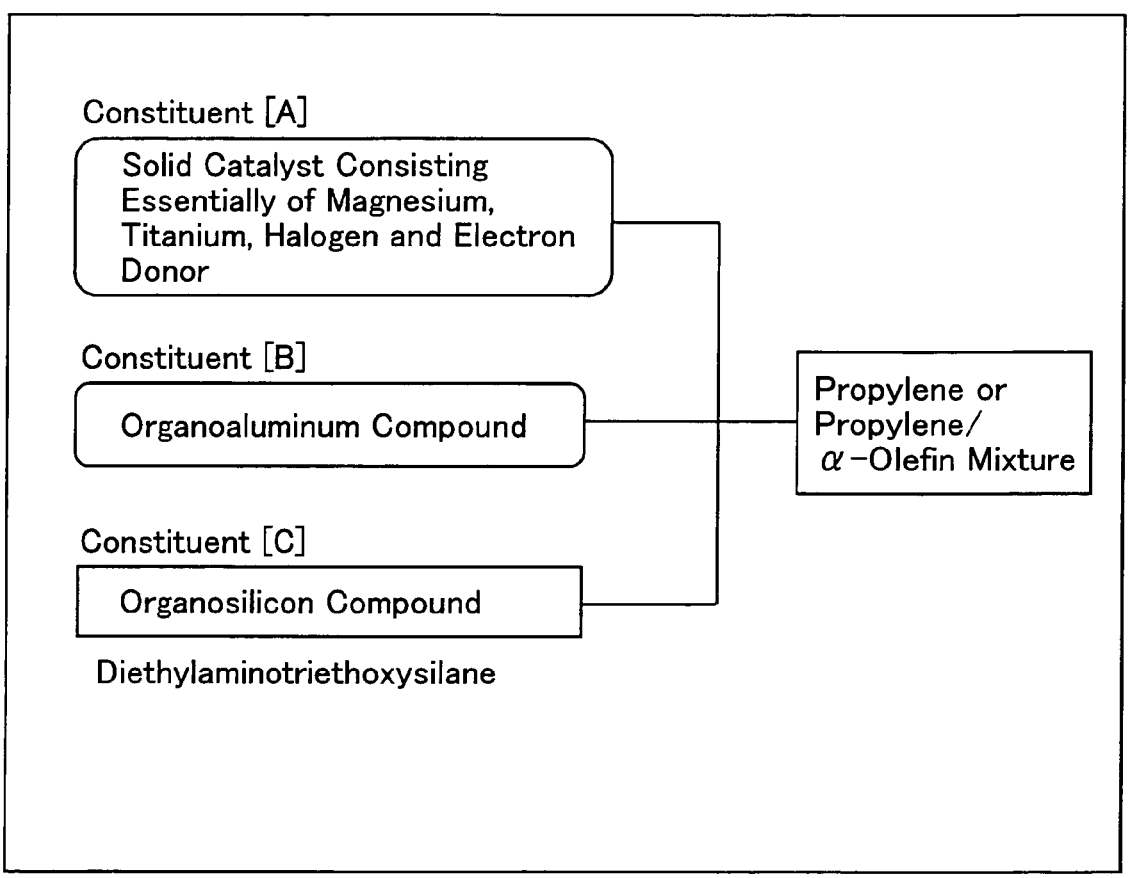
FIG. 13 is a flowchart of an adjustment method and polymerization method of a catalyst constituent for use in Experimental example 10.

A 2L-inner volume autoclave composed of stainless steel and equipped with a magnet seal agitator is employed, of which inside is fully substituted for nitrogen. Supplied into the autoclave were: n-heptane slurry of the constituent [A] by 2.5×10⁻³ mmol on a titanium atom basis; triethyl aluminum as the constituent [B] by 2.2 mmol; and the organosilicon compound according to Example 1 or the catalyst constituent according to Comparative example 3 as the constituent [C] by 0.36 mmol. Then, hydrogen (0.12 MPa), ethylene (0.2 MPa) and liquefied propylene (1.2 L) were introduced sequentially therein. After cooling the inside of the autoclave down to 10° C., agitating was initiated and prepolymerization was performed for 10 minutes. Subsequently, the temperature inside the autoclave was elevated up to 70° C., then polymerization was performed at 70° C. for twenty minutes under polymerization pressure of 3.3 MPa. After completion of polymerization, the non-reacted gas was discharged, and the polymer was dried under reduced pressure at 60° C. for 20 hours to produce white powdery polymer. A flowchart of an adjustment method and polymerization method of the catalyst constituents for use in Experimental example 10 is shown in FIG. 13, and experiment results are shown in Tables 19 and 20.

TABLE 19

| | Prepared Ethylene MPa | Yield g-PP/ g-Cat | Ethylene Content wt % | MFR g/10 min | H.I % | Tc ° C. |
|---|---|---|---|---|---|---|
| Example 1 | 0 | 20,200 | 0 | 46.3 | 98.0 | 115.3 |
| | 0.2 | 23,100 | 2.13 | 37.9 | 73.3 | 105.7 |
| Comparative example 3 | 0 | 19,400 | 0 | 10.0 | 98.6 | 113.6 |
| | 0.2 | 21,300 | 2.04 | 7.7 | 78.8 | 102.5 |

TABLE 20

| | Tm ° C. | ΔH J/g | Mw × 10−4 | Mw/Mn | Mz/Mw | mmmm % | $r_1 r_2$ |
|---|---|---|---|---|---|---|---|
| Example 1 | 164.4 | 112.0 | 23.8 | 8.1 | 3.9 | 98.4 | — |
| | 156.3 | 88.7 | 24.8 | 5.6 | 3.1 | 98.3 | 3.35 |
| Comparative example 3 | 164.3 | 116.0 | 40.1 | 7.4 | 4.2 | 97.6 | — |
| | 149.2 | 92.9 | 39.7 | 6.6 | 3.7 | 97.7 | 4.79 |

It is found that when the catalyst constituent according to Example 1 is employed, hydrogen response is better, polymarization reaction rate is higher, stereoregularity of the resultant α-olefin polymer is higher, randomness is better, and melt fluidity is higher than when the catalyst constituent according to Comparative example 3 is employed. It is defined that the smaller the value of $r_1 r_2$ the better the randomness.

EXPERIMENTAL EXAMPLE 11

(Block Copolymerization of Ethylene-propylene)

As Experimental example 11, block copolymerization of ethylene/propylene was performed using an α-olefin polymerization catalyst consisting of the solid catalyst constituent [A], the organoaluminum compound constituent [B], and the catalyst constituent [C] according to Example 1. In Experimental example 11, as the solid catalyst constituent [A], a THC-JC type was employed, which is commercially available from Toho Catalyst. Ti content was 1.7 wt. %. As the organoaluminum compound constituent [B], tri(ethyl) aluminum was employed. In Experimental example 11, hydrogen is added in the second step for copolymerization.

<First Step: Propylene Bulk Homopolymerization>

A 2L-inner volume autoclave composed of stainless steel and equipped with a magnet seal agitator is employed, of which inside is fully substituted for nitrogen. Supplied into the autoclave were: n-heptane slurry of the previously obtained solid catalyst constituent [A] by 2.5×10⁻³ mmol on titanium atom basis; tri(ethyl)aluminum as the organoaluminum compound constituent [B] by 1.5 mmol; and the organosilicon compound according to Example 1 as the constituent[C]by 0.25 mmol. Then, hydrogen (0.4 MPa) and liquefied propylene (1.2 L) were introduced sequentially therein. After cooling the inside of the autoclave down to 10° C., agitating was initiated and prepolymerization was performed for 10 minutes. Subsequently, the temperature inside the autoclave was elevated up to 70° C., then polymerization was performed at 70° C. for one hour under polymerization pressure of 3.8 MPa. After completion of polymerization, the non-reacted propylene gas was discharged, and the inside was substituted sufficiently for nitrogen. Then, pressure in the autoclave was held at 0.02 MPa in gauge pressure. Thereafter, the weight was measured, and the yield of polypropylene was calculated from the weight of the empty autoclave and found 300 g. After measurement of the yield, 102 g of polypropylene was extracted from inside the autoclave in nitrogen ambient. Then, the extracted polymer was dried under reduced pressure at 60° C. for 20 hours to produce white powdery polypropylene.

<Second Step: Gas-phase Ethylene/Propylene Copolymerization>

After completion of bulk polymerization, in which the pressure in the system was held at 0.02 MPa in gauge pressure, the temperature in the autoclave was set at 70° C. Mixed gas of ethylene, propylene and hydrogen was continuously supplied to the autoclave at a proportion of 0.7:1:0.026 in volume ratio (700 Ncc/min, 1000 Ncc/min and 26 Ncc/min, respectively) to adjust the copolymerization pressure at 1.22 MPa in gauge pressure. For copolymerization reactions at the same temperature under the same pressure, the non-reacted gas was discharged outside the system so as to hold the copolymerization pressure at 1.2 MPa in gauge pressure, followed by copolymerization reaction at 70° C. for 3 hours. During the copolymerization reaction (after 0.5 hour, one hour and two hours), each 20 g of. the polymer was extracted from inside the autoclave. The extracted copolymer was dried under reduced pressure at 60° C. for 20 hours to produce white powdery block copolymer. A proportion of the copolymer part in the total polymer (block ratio) was calculated and found 12.00 wt. % after 0.5 hour; 18.43 wt. % after one hour; 25.20 wt. % after 2 hours; and 29.19 wt. % after 3 hours.

As Comparative experiments to Experimental example 11, ethylene-propylene block copolymerization was performed like Experimental example 11 to obtain a product using the catalyst constituent according to Example 1, in which hydrogen was not added in the second step; and products using the catalyst constituent according to Comparative example 3, in which hydrogen was added and not added in the second step. These results are shown in Tables 21 and 22.

TABLE 21

| | Homo-PP | | | | Hydrogen |
|---|---|---|---|---|---|
| | Homo Yield g-HP/g-Cat. hr | MFR g/10 min | mmmm % | E/P Molar Ratio | Partial Pressure MPa |
| Example 1 | 42,900 | 470 | — | 0.7 | 0.02 |
| | 41,100 | 400 | 99.1 | 0.7 | 0 |
| Comparative example 3 | 43,100 | 76.1 | — | 0.7 | 0.02 |
| | 42,300 | 60.1 | 98.2 | 0.7 | 0 |

TABLE 22

| | Copolymer-ization Time hr | Copolymer-ization Yield g-CP/g-Cat | M F R g/10 min | Block Ratio wt % | p-xylene Soluble Component | | | p-xylene Insoluble Component |
|---|---|---|---|---|---|---|---|---|
| | | | | | Weight wt % | Ethylene Content wt % | [η] dl/g | Ethylene Content wt % |
| Example 1 (Hydrogen partial pressure: 0.02 MPa) | 0.5 | 5,800 | 242 | 12.0 | 11.0 | 37.5 | 3.0 | 1.3 |
| | 1 | 9,700 | 145 | 18.4 | 15.8 | 39.1 | 3.2 | 2.5 |
| | 2 | 14,400 | 86.8 | 25.2 | 21.7 | 39.8 | 3.3 | 3.7 |
| | 3 | 17,700 | 67.1 | 29.2 | 24.3 | 39.8 | 3.4 | 5.5 |
| Example 1 (Hydrogen partial pressure: 0 MPa) | 0.5 | 3,500 | 111 | 7.8 | 6.4 | 39.6 | 11.0 | 1.4 |
| | 1 | 5,800 | 66.3 | 12.3 | 9.6 | 39.5 | 11.6 | 2.3 |
| | 2 | 8,800 | 39.0 | 17.5 | 13.8 | 40.0 | 12.0 | 2.7 |
| | 3 | 10,700 | 34.9 | 20.7 | 15.9 | 40.4 | 12.3 | 3.7 |
| Comparative example 3 (Hydrogen partial pressure: 0.02 MPa) | 0.5 | 6,300 | 40.6 | 12.7 | 11.3 | 31.4 | 2.8 | 1.8 |
| | 1 | 9,800 | 30.0 | 18.5 | 16.5 | 32.4 | 2.8 | 2.8 |
| | 2 | 14,000 | 21.1 | 24.5 | 21.6 | 32.1 | 2.9 | 3.9 |
| | 3 | 16,600 | 17.0 | 27.8 | 21.9 | 32.5 | 3.0 | 5.5 |
| Comparative example 3 (Hydrogen partial pressure: 0 MPa) | 0.5 | 5,400 | 26.5 | 11.3 | 8.8 | 31.4 | 6.3 | 2.1 |
| | 1 | 9,100 | 14.0 | 17.7 | 13.6 | 30.9 | 6.6 | 3.5 |
| | 2 | 13,600 | 8.9 | 24.3 | 19.0 | 31.2 | 7.0 | 4.9 |
| | 3 | 16,400 | 7.5 | 27.9 | 21.2 | 32.0 | 7.0 | 5.2 |

As obvious from Tables 21 and 22, in the product using the catalyst constituent according to Example 1, addition of hydrogen can particularly improve copolymarization reaction rate compared to that for use in Comparative example 3.

EXPERIMENTAL EXAMPLE 12

(Melting and Kneading of Ethylene-propylene Block Copolymer)

In Experimental example 11, to ethylene-propylene block copolymer with hydrogen partial pressure of 0.02 MPa and copolymerization time of 3 hours, additives (BHT, hydrotalcite, calcium stearate, Irganox 1010, and distearyl thiopropionate each 1000 ppm) were added. A biaxial extruder with an inner volume of 30 cm³ and a screw diameter of 15 mm was employed to produce extrusions on such a condition that achieves a resin temperature of 220° C. and a revolution speed of 20-30 rpm.

Figure 14:
FIG. 14 shows a microphotograph (4000 times) of extrusions of an ethylene-propylene block copolymer produced in Experimental example 12 using a catalyst constituent according to Example 1.
Figure 15:
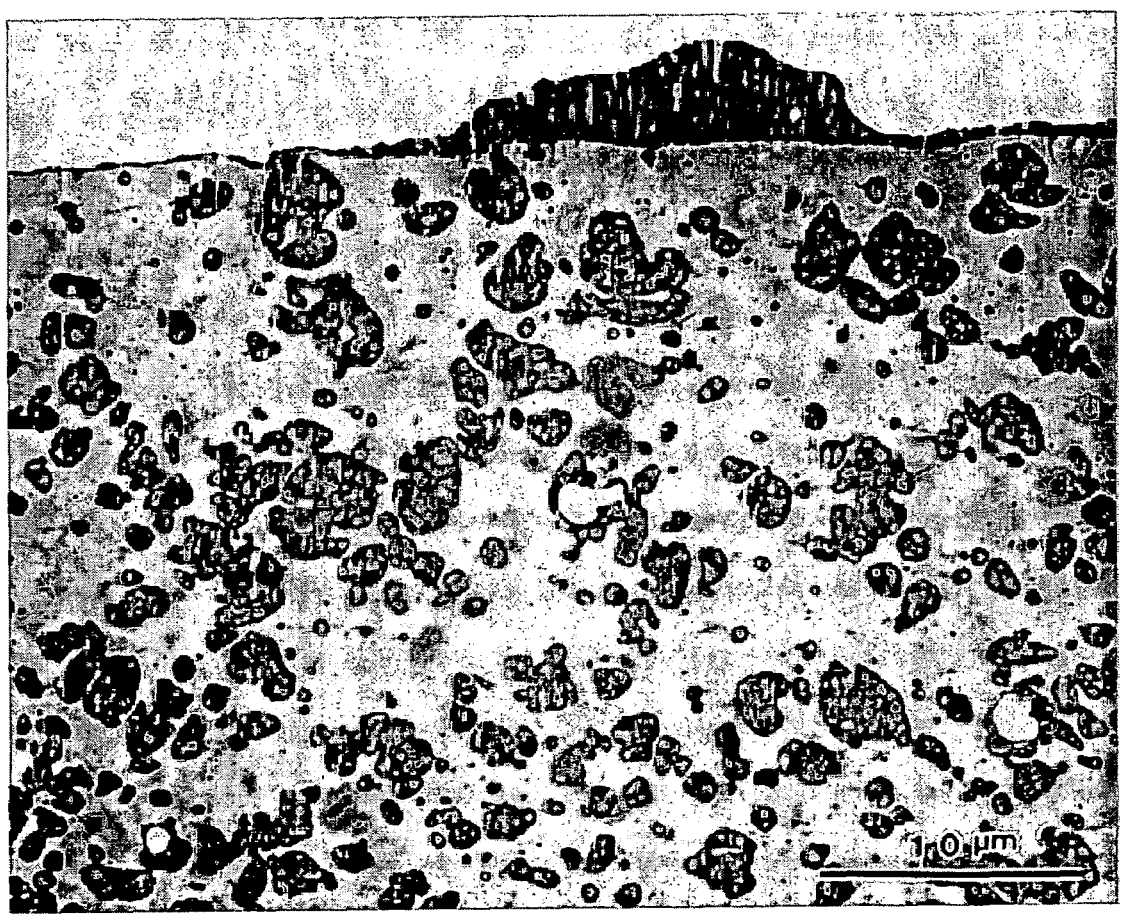
FIG. 15 shows a microphotograph (4000 times) of extrusions of an ethylene-propylene block copolymer produced in Experimental example 12 using a catalyst constituent according to Comparative example 3.

This produced sample was embedded in an epoxy resin, then facetted with an ultra microtome equipped with a diamond knife (EM-REICHERT ULTRACUT J available from Leica), and pigmented. Thereafter, ultra thin pieces were formed for observation under a transmissive electron microscope (H-7100FA available from Hitachi). The result on the product according to Example 1 is shown in FIG. 14 and the result on the product according to Comparative example 3 is shown in FIG. 15. As obvious from FIGS. 14 and 15, the ethylene-propylene block copolymer produced using the product according to Example 1 has such a structure that exhibits no bleed-out in the surface thereof. In contrast, the ethylene-propylene block copolymer produced using the product according to Comparative example 3 has such a structure that exhibits bleed-out in the surface thereof.

EXPERIMENTAL EXAMPLE 13

(Synthesis of Diethylaminotriethoxysilane)

A 300 mL-volume flask equipped with an agitating blade and dropping funnel was employed, of which inside was substituted for nitrogen using a vacuum pump. Then, 8.5 g (0.050 mol) of tetrachlorosilane; 100 mL of dehydrated n-heptane; and 0.48 g (0.0025 mol) of p-toluene sulfonic acid monohydrate were supplied into the flask and agitated igood bath. Solution of 22.2 g (0.15 mol)ethyl orthoformate dissolved in 25 mL dehydrated n-heptane is supplied into the dropping funnel. While being agitated igood bath, the ethyl orthoformate solution was dropped slowly from the dropping funnel, followed by ice cooling and agitating for 5 hours, and left for 3 nights at room temperature. From gas chromatography at this moment, it was confirmed that chlorotriethoxysilane was generated by 78%. After another ice cooling, 10.1 g (0.10 mol) of triethylamine was added to the reacted solution, then solution of 3.7 g (0.050 mol) diethylamine dissolved in 5 mL dehydrated n-heptane was dropped slowly from the dropping funnel. After ice cooling and agitating for 2 hours, it was left for one night at room temperature. Analysis of the resultant reacted solution by gas chromatography found production of 1% chlorotriethoxysilane and 78% triethoxy(diethylamino)silane, and by-production of 8% tetraethoxysilane.

Instead of the p-toluene sulfonic acid monohydrate, 0.43 g (0.0025 mol) of p-toluene sulfonic acid was employed to perform the same reaction as Example 1 except for leaving one night instead of 3 nights. From analysis by gas chromatography at a stage before addition of diethylamine, production of 61% chlorotriethoxysilane was confirmed. After the addition of diethyl amine, production of 1% chlorotriethoxysilane and 59% triethoxy(diethylamino)silane, and by-production of 13% tetraethoxy silane were confirmed.

Instead of ethyl orthoformate, ethanol was added to perform Comparative experiment 1 to Experimental example 13. Namely, a 300 mL-volume flask equipped with an agitating blade and dropping funnel was employed, of which inside was substituted for nitrogen using a vacuum pump. Then, 8.5 g (0.050 mol) of tetrachlorosilane; 100 mL of dehydrated n-heptane; and 30.4 g (0.30 mol) of triethylamine were supplied into the flask and agitated igood bath. A solution of 6.9 g (0.15 mol) ethanol dissolved in 20 mL dehydrated n-heptane is supplied into the dropping funnel. While being agitated igood bath, the ethanol solution was dropped slowly from the dropping funnel, followed by ice cooling and agitating for 4 hours, and left for 2 nights at room temperature. Analysis of the resultant reacted solution by gas chromatography found production of 7% target chlorotriethoxysilane, and by-production of 60% tetraethoxysilane.

Instead of ethyl orthoformate, sodium ethoxide was added to perform Comparative experiment 2 to Experimental example 13. Namely, a 300 mL-volume flask equipped with an agitating blade and dropping funnel was employed, of which inside was substituted for nitrogen using a vacuum pump. Then, 5.1 g (0.030 mol) of tetrachlorosilane and 100 mL of dehydrated n-heptane were supplied into the flask and agitated igood bath. Solution of 6.1 g (0.090 mol) sodium ethoxide sufficiently uniformly suspended in 90 mL dehydrated THF is supplied into the dropping funnel. While being agitated igood bath, the suspension was dropped slowly from the dropping funnel, followed by ice cooling and agitating for one hour, and left for 3 nights at room temperature. Analysis of the resultant reacted solution by gas chromatography found production of 14% chlorotriethoxysilane. After another ice cooling, 6.1 g (0.060 mol) of triethylamine was added into the reacted solution. Then, solution of 2.2 g (0.030 mol) diethylamine dissolved in 6 mL dehydrated n-heptane was slowly dropped from the dropping funnel. It was agitated for 2 hours igood bath, and then agitated for 2 hours at room temperature. Analysis of the resultant reacted solution by gas chromatography found no production of chlorotriethoxysilane and triethoxy(diethylamino)silane, and by-production of 22% tetraethoxysilane.

Comparative experiment 3 to Experimental example 13 was performed by first adding diethylamine to tetrachlorosilane, and then ethoxidizing it using ethylorthoformate. Namely, a 200 mL-volume flask equipped with an agitating blade and dropping funnel was employed, of which inside was substituted for nitrogen using a vacuum pump. Thereafter, 5.1 g (0.030 mol) of tetrachlorosilane and 70 mL of dehydrated n-heptane were supplied into the flask, then 18.2 g (0.18 mol) of triethylamine was added, and agitated igood bath. Solution of 2.2 g (0.030 mol) diethylamine dissolved in 20 mL dehydrated n-heptane is supplied into the dropping funnel. While being agitated igood bath, the diethylamine solution was dropped slowly from the dropping funnel, followed by ice cooling and agitating for two hours. Triethylamine hydrochloride of the reacted product was remove by filtration in nitrogen gas ambient. The resultant reacted solution was ice cooled again. Then, 23.8 g (0.16 mol) of triethylorthoformate was dropped into the reacted solution. It was agitated for one hour igood bath, then agitated for 4 hours at room temperature, and heated until it revolved. Analysis of the resultant reacted solution by gas chromatography confirmed 35% triethoxy(diethylamino)silane.

Comparative experiment 4 to Experimental example 13 was performed by first adding diethylamine to tetrachlorosilane, and then ethoxidizing it using ethanol. Namely, like Comparative experiment 3, tetrachlorosilane was reacted with diethylamine. The resultant reacted solution was ice cooled again. Then, ethanol was dropped into the reacted solution instead of triethylorthoformate. It was agitated for 3 hours igood bath, then agitated for 2 hours at room temperature. Analysis of the resultant reacted solution by gas chromatography confirmed 22% triethoxy(diethylamino)silane and by-production of 37% tetraethoxysilane.

Comparative experiment 5 to Experimental example 13 was performed by first adding diethylamine to tetrachlorosilane, and then ethoxidizing it using sodium ethoxide. Namely, 500 mL-volume flask equipped with an agitating blade and dropping funnel was employed, of which inside was substituted for nitrogen using a vacuum pump. Thereafter, 8.5 g (0.050 mol) of tetrachlorosilane and 50 mL of dehydrated n-heptane were supplied into the flask, then 20.2 g (0.20 mol) of triethylamine was added, and agitated igood bath. Solution of 3.7 g (0.050 mol) diethylamine dissolved in 5.2 mL dehydrated n-heptane is supplied into the dropping funnel. While being agitated igood bath, the diethylamine solution was dropped slowly from the dropping funnel, followed by ice cooling and agitating for two hours. Triethyl amine hydrochloride of the reacted product was remove by filtration in nitrogen gas ambient. The resultant reacted solution was ice cooled again. Then, 61.2 g (0.18 mol) solution of 20 wt. % sodium ethoxide in ethanol was dropped into the reacted solution. It was agitated for 3 hours igood bath. Analysis of the resultant reacted solution by gas chromatography confirmed 39% triethoxy(diethylamino)silane and by-production of 40% tetraethoxysilane.

Comparative experiment 6 to The reacted product 13 was performed by direct amino group substitution of tetraethoxy silane not via Grignard reagent. Namely, a 200 mL-volume flask, equipped with an agitating blade and a soxhlet extractor loaded with a monocular shive 4A-stuffed cylindrical paper filter, was employed, of which inside was substituted for nitrogen using a vacuum pump. Then, 83.3 g (0.40 mol) of tetraethoxysilane and 73.1 g (1.0 mol) of diethylamine were fed into the flask, and heated and revolved for 8 hours. Analysis of the resultant reacted solution by gas chromatography confirmed no target amino-substituted product but tetraethoxysilane of the starting substance only.

EXPERIMENTAL EXAMPLE 14

(Tensile Elastic Modulus of Polypropylene)

Tensile elastic moduli were measured in the following manner on polypropylene with MFR of 12.8 produced like The reacted product 1 and polypropylene with MFR of 13.6 produced like The reacted product 4, using the catalyst constituent [C] according to Example 1. A method of making tensile test samples is performed for 4 minutes at 230° C. (3 minutes for heating, and one minute for press (80 kg/cm$^2$)), and one minute at 30° C. A test piece is formed 40 mm×5 mm×0.2 mm with a cross head speed of 5 mm/min, 23° C., 50%. A tester for use in the tensile test was a Tensilon universal tester RTA-500 available from Orientech Inc. As a result of the test, the one produced like The reacted product 1 had a tensile elastic modulus of 733 MPa, and the one produced like The reacted product 4 had a tensile elastic modulus of 757 MPa.

EXPERIMENTAL EXAMPLE 15

(Electron Density of Compound)

Specific compounds having the constituent represented by the above Formula 14 were structurally optimized using a PM3 approximation to calculate electron densities on nitrogen (N) and oxygen (O), which are shown in Table 23. The calculation was performed using MOPAC7.

TABLE 23

| | Electron Density | | | | |
|---|---|---|---|---|---|
| | $O_1$ | $O_2$ | $O_3$ | $O_{av}$ | N |
| Dimethylamino triethoxy silane | 6.4510 | 6.4266 | 6.4555 | 6.4444 | 5.2262 |
| Diethylamino triethoxy silane | 6.4460 | 6.4533 | 6.4396 | 6.4463 | 5.2020 |
| n-propylmethylamino triethoxy silane | 6.4363 | 6.4509 | 6.4537 | 6.4470 | 5.2109 |
| n-propylethylamino triethoxy silane | 6.4203 | 6.4718 | 6.4476 | 6.4466 | 5.2002 |
| Di n-propylamino triethoxy silane | 6.4460 | 6.4438 | 6.4516 | 6.4471 | 5.1978 |
| n-butylamino triethoxy silane | 6.4499 | 6.4562 | 6.4562 | 6.4541 | 5.1950 |

The invention claimed is:

1. A catalyst constituent of catalyst for polymerizing or copolymerizing an α-olefin, represented by Formula 1:

$$Si(OR^1)_3(NR^2R^3) \quad \text{Formula 1}$$

wherein in Formula 1, $R^1$ is an ethyl group; $R^2$ is a hydrocarbon group with 1 to 12 carbon atoms or hydrogen; and $R^3$ is a hydrocarbon group with 1 to 12 carbon atoms.

2. The catalyst constituent of catalyst for polymerizing or copolymerizing an α-olefin according to claim 1, wherein the compound represented by Formula 1 comprises one or more of: dimethylaminotriethoxysilane; diethylaminotriethoxysilane; di-n-propylaminotriethyloxysilane; methyl-n-propylaminotriethoxysilane; t-butylaminotriethoxysilane; ethyl-n-propylaminotriethoxysilane; ethylisopropylaminotriethoxysilane; and methylethylaminotriethoxysilane.

3. A catalyst for polymerizing or copolymerizing an α-olefin, including the catalyst constituent according to claim 1.

4. A catalyst for polymerizing or copolymerizing an α-olefin, including [A] a solid catalyst constituent consisting essentially of magnesium, titanium, a halogen element and an electron donor; [B] an organoaluminum compound constituent; and [C] the catalyst constituent according to claim 1.

5. An α-olefin polymerization method of polymerizing or copolymerizing an α-olefin in the presence of the catalyst for polymerizing or copolymerizing an α-olefin, including the catalyst constituent of catalyst for polymerizing or copolymerizing an α-olefin, represented by Formula 1:

$$Si(OR^1)_3(NR^2R^3) \quad \text{Formula 1}$$

wherein in Formula 1, $R^1$ is an ethyl group; $R^2$ is a hydrocarbon group with 1 to 12 carbon atoms or hydrogen; and $R^3$ is a hydrocarbon group with 1 to 12 carbon atoms.

6. A method of manufacturing α-olefin propylene block copolymers, comprising a first step of homopolymerizing propylene in the presence of the catalyst for polymerizing or copolymerizing an α-olefin, including the catalyst constituent of catalyst for polymerizing or copolymerizing an α-olefin, represented by Formula 1:

$$Si(OR^1)_3(NR^2R^3) \quad \text{Formula 1}$$

(wherein in Formula 1, $R^1$ is an ethyl group; $R^2$ is a hydrocarbon group with 1 to 12 carbon atoms or hydrogen; and $R^3$ is a hydrocarbon group with 1 to 12 carbon atoms);

and a second step of block copolymerizing a combined monomer of propylene with an α-olefin other than propylene in the presence of the same catalyst after the first step.

7. The method of manufacturing α-olefin propylene block copolymers according to claim 6, wherein the second step includes gas-phase copolymerizing the combined monomer of propylene with the α-olefin other than propylene without inactivation of the catalyst used in the first step.

8. The method of manufacturing α-olefin propylene block copolymers according to claim 6, wherein the α-olefin is ethylene.

9. The method of manufacturing α-olefin propylene block copolymers according to claim 6, wherein the second step includes adding hydrogen in copolymerization.

10. A method of manufacturing α-olefin propylene random copolymers, comprising random copolymerizing a combined monomer of propylene with an α-olefin other than propylene in the presence of the catalyst for polymerizing or copolymerizing an α-olefin, including the catalyst constituent of catalyst for polymerizing or copolymerizing an α-olefin, represented by Formula 1:

$$Si(OR^1)_3(NR^2R^3) \quad \text{Formula 1}$$

wherein in Formula 1, $R^1$ is an ethyl group; $R^2$ is a hydrocarbon group with 1 to 12 carbon atoms or hydrogen; and $R^3$ is a hydrocarbon group with 1 to 12 carbon atoms.

11. The method of manufacturing α-olefin propylene random copolymers according to claim 10, wherein the α-olefin is ethylene.

* * * * *

UNITED STATES PATENT AND TRADEMARK OFFICE
CERTIFICATE OF CORRECTION

| | |
|---|---|
| PATENT NO. | : 7,238,758 B2 |
| APPLICATION NO. | : 10/503414 |
| DATED | : July 3, 2007 |
| INVENTOR(S) | : Motozo Yoshikiyo et al. |

It is certified that error appears in the above-identified patent and that said Letters Patent is hereby corrected as shown below:

COLUMN 18, LINES 48 and 50
"bis(2,3,8-trimethyll, 2,3,4-tetrahydroquinolino)dimethoxysilane,
bis(2,3,9-trimethyl,-l,2,3,4l-tetrahydroquinolino)dimethoxysilane,"
should be
-- bis(2,3,8-trimethyl-1,2,3,4-tetrahydroquinolino)dimethoxysilane,
bis(2,3,9-trimethyl-l,2,3,4 -tetrahydroquinolino)dimethoxysilane,--

Signed and Sealed this

Eighteenth Day of December, 2007

JON W. DUDAS
*Director of the United States Patent and Trademark Office*